US009931387B2

(12) United States Patent
Langlade Demoyen et al.

(10) Patent No.: US 9,931,387 B2
(45) Date of Patent: *Apr. 3, 2018

(54) CANCER VACCINE FOR CATS

(71) Applicant: INVECTYS, Paris (FR)

(72) Inventors: Pierre Langlade Demoyen, Neuilly sur Seine (FR); Simon Wain-Hobson, Montigny-le-Bretonneux (FR); Christelle Liard, Chatillon (FR)

(73) Assignee: INVECTYS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/780,613

(22) PCT Filed: Mar. 28, 2014

(86) PCT No.: PCT/EP2014/056380
§ 371 (c)(1),
(2) Date: Sep. 28, 2015

(87) PCT Pub. No.: WO2014/154904
PCT Pub. Date: Oct. 2, 2014

(65) Prior Publication Data
US 2016/0051650 A1 Feb. 25, 2016

(30) Foreign Application Priority Data
Mar. 28, 2013 (EP) .................... 13305404

(51) Int. Cl.
A61K 39/00 (2006.01)
C07H 21/04 (2006.01)
C12N 15/00 (2006.01)
C12N 9/12 (2006.01)
A61K 41/00 (2006.01)
C12N 15/79 (2006.01)

(52) U.S. Cl.
CPC .......... A61K 39/0011 (2013.01); A61K 41/00 (2013.01); C12N 9/1241 (2013.01); C12N 9/1276 (2013.01); C12Y 207/07049 (2013.01); A61K 2039/53 (2013.01); A61K 2039/552 (2013.01); C07H 21/04 (2013.01); C12N 15/79 (2013.01); C12N 2800/10 (2013.01)

(58) Field of Classification Search
CPC .. A61K 2039/53; C07H 21/04; C12N 9/1276; C12N 15/79; C12N 2800/10
USPC ..................... 536/23.2; 435/320.1; 424/185.1
See application file for complete search history.

(56) References Cited

U.S. PATENT DOCUMENTS

| | | | |
|---|---|---|---|
| 5,539,084 A | 7/1996 | Geysen et al. | |
| 5,840,839 A | 11/1998 | Wang et al. | |
| 8,003,773 B2 | 8/2011 | Langlade-Demoyen et al. | |
| 8,222,392 B2 | 7/2012 | Cech et al. | |
| 2003/0143228 A1 | 7/2003 | Chen et al. | |
| 2004/0106128 A1 | 6/2004 | Majumdar | |
| 2008/0090778 A1 | 4/2008 | Scarselli et al. | |
| 2009/0175892 A1 | 7/2009 | Langlade-Demoyen et al. | |
| 2009/0269739 A1 | 10/2009 | Cech et al. | |
| 2011/0318380 A1 | 12/2011 | Brix et al. | |
| 2016/0347798 A1 | 12/2016 | Poma et al. | |

FOREIGN PATENT DOCUMENTS

| | | |
|---|---|---|
| WO | 98/14593 A2 | 4/1998 |
| WO | 2003038047 A2 | 5/2003 |
| WO | 2008043760 A2 | 4/2008 |

OTHER PUBLICATIONS

NCBI reference sequence XP_019669508.1, pp. 1-2.*
Adotevi, Olivier et al., "Immunogenic HLA-B *0702-Restricted Epitopes Derived from Human Telomerase Reverse Transcriptase that Elicit Antitumor Cytotoxic T-Cell Responses" Clin Cancer Res (2006), vol. 12, No. 10, pp. 3158-3167.
Adotevi, Olivier et al., "Targeting human telomerase reverse transcriptase with recombinant lentivector is highly effective to stimulate antitumor CD8 T-cell immunity in vivo" Blood (2010), vol. 115, No. 15, pp. 3025-3032.
Artandi, Steven E. et al. "Telomeres and telomerase in cancer", Carcinogenesis (2010), vol. 31, No. 1, pp. 9-18.
Bevan, Michael J., "Helping the CD8+ T-Cell Response", Nature Reviews Immunology (2004), vol. 4, pp. 595-602.
Godet, Yann et al. "Analysis of Spontaneous Tumor-Specific CD4 T-cell Immunity in Lung Cancer Using Promiscuous HLA-DR Telomerase-Derived Epitopes: Potential Synergistic Effect with Chemotherapy Response", Clinical Cancer Research: An Official Journal of the American Association for Cancer Research (2012), vol. 18No. 10, pp. 2943-2953.
European Search Report and Opinion dated Sep. 24, 2012, which issued during prosecution of European Application No. 12305319.1, 7 pages.
Hanahan, Douglas et al., "Hallmarks of Cancer: The Next Generation" Cell (2011), vol. 144, pp. 646-674.
International Search Report and Written Opinion of the International Searching Authority dated Apr. 12, 2013, which issued during prosecution of International Application No. PCT/EP2013/054592, 10 pages.
International Preliminary Report on Patentability Issued in International Application No. PCT/EP2013/054592 dated Sep. 16, 2014; 5 pages.
International Search Report and Written Opinion of the International Searching Authority dated Jul. 2, 2014 which issued during prosecution of International Patent Application No. PCT/EP2014/056381.

(Continued)

Primary Examiner — Shin Lin Chen
(74) Attorney, Agent, or Firm — Troutman Sanders LLP

(57) ABSTRACT

The present invention provides a nucleic acid, or an immunogenic composition thereof, that comprises a sequence encoding a cat telomerase deprived of telomerase catalytic activity, or a fragment thereof. The present invention also provides methods for triggering an immune response in a cat and methods for treating or preventing a tumor in a cat using the immunogenic composition of the invention.

16 Claims, 13 Drawing Sheets

(56) References Cited

OTHER PUBLICATIONS

Kiecker, Felix et al., "Analysis of Antigen-Specific T-Cell Responses With Synthetic Peptides—What Kind of Peptide for Which Purpose?", Human Immunology (2004), vol. 65, pp. 523-536.
Klebanoff, Christopher A. et al., "Therapeutic cancer vaccines: are we there yet?", Immunology Reviews (2011), vol. 239, pp. 27-44.
Kyte, Jon Amund et al. "Telomerase Peptide Vaccination Combined with Temozolomide: A Clinical Trial in Stage IV Melanoma Patients", Clinical Cancer Research (2011), vol. 7, No. 13, pp. 4568-4580.
Martinez, Paula et al., "Telomeric and extra-telomeric roles for telomerase and the telomere-binding proteins" Nature Reviews Cancer (2011), vol. 11, pp. 161-176.
Osen, Wolfram et al. "Screening of Human Tumor Antigens for CD4+ T Cell Epitopes by Combination of HLA-Transgenic Mice, Recombinant Adenovirus and Antigen Peptide Libraries", PLoS ONE (2010), vol. 5, Issue 11, p. e14137.
Scardino, Antonio et al., "HER-2/neu and hTERT Cryptic Epitopes as Novel Targets for Broad Spectrum Tumor Immunotherapy", The Journal of Immunology (2002), vol. 168, pp. 5900-5906.
Schlapbach, Christoph et al. "Telomerase-specific GV1001 peptide vaccination fails to induce objective tumor response in patients with cutaneous T cell lymphoma" Journal of Dermatological Science (2011), vol. 62, No. 2, pp. 75-83.
Schroers, Roland et al., "Human Telomerase Reverse Transcriptase-Specific T-Helper Responses Induced by Promiscuous Major Histocompatibility Complex Class II-Restricted Epitopes" Clinical Cancer Research: An Official Journal of the American Association for Cancer Research (2003), vol. 9, No. 13, pp. 4743-4755.
Schroers, Roland et al. "Identification of HLA DR7-restricted Epitopes from Human Telomerase Reverse Transcriptase Recognized by CD4+ T-Helper Cells" Cancer Research, American Association for Cancer Research (2002), vol. 62, No. 9, pp. 2600-2605.
Reay, Philip et al., "Use of Global Amino Replacements to Define the Requirements for MHC Binding and T Cell Recognition of Moth Cytochrome c (93-103)", Journal of Immunology (1994), vol. 152, pp. 3946-3957.
Bolonaki, Irini et al. "Vaccination of Patients with Advanced Non-Small-Cell Lung Cancer With an Optimized Cryptic Human Telomerase Reverse Transcriptase Peptide" Journal of Clinical Oncology: Official Journal of the American Society of Clinical Oncology (2007) vol. 25:19, pp. 2727-2734.
Ruden, Maria et al. "Novel anticancer therapeutics targeting telomerase" Cancer Treatment Reviews (2013), vol. 39, No. 5, pp. 444-456.
Yang, Yinhua et al. "Nucleolar Localization of hTERT Protein is Associated with Telomerase Function" Experimental Cell Research (2002), vol. 277, No. 2, pp. 201-209.
International Search Report and Written Opinion of the International Searching Authority dated Feb. 4, 2015, which issued during prosecution of International Application No. PCT/EP2014/073164, 10 pages.
International Preliminary Report on Patentability Issued in International Application No. PCT/EP2014/073164 Issued May 3, 2016, 6 pages.
Peruzzi, D., et al: "Telomerase and HER-2/neu as targets of genetic cancer vaccines in dogs", Vaccine, 2010, vol. 28, No. 5, pp. 1201-1208.
Peruzzi, Daniela, et al: "A Vaccine Targeting Telomerase Enhances Survival of Dogs Affected by B-cell Lymphoma", Molecular Therapy, 2010, vol. 18, No. 8, pp. 1559-1567.

International Search Report and Written Opinion of the International Searching Authority issued in PCT/EP2014/056380 (dated Jul. 23, 2014).
Muller, S., "Ubiquitin", Manual of Biological Markers of Disease (1994), B2, 3, pp. 1-11.
NCBI Sequence AAC51724.1, Telomerase catalytic subunit [*Homo sapiens*], dated Aug. 28, 1997, 2 pages.
Delogu, G. et al., "DNA Vaccine Combinations Expressing Either Tissue Plasminogen Activator Signal Sequence Fusion Proteins or Ubiquitin-Conjugated Antigens Induce Sustained Protective Immunity in a Mouse Model of Pulmonary Tuberculosis", Infection and Immunity (2002), vol. 70, No. 1, pp. 292-302.
Andersson, H. A. et al., "Maximizing Antigen Targeting to the Proteasome for Gene-Based Vaccines", Molecular Therapy (2004), vol. 10, No. 3, pp. 432-446.
Drosopoulos, W. C. et al., "The active site residue Valine 867 in human telomerase reverse transcriptase influences nucleotide incorporation and fidelity", Nucleic Acids Research (2007), vol. 35, No. 4, pp. 1155-1168.
European Communication Pursuant to Article 94(3) EPC issued in EP14716530.2 and dated Jan. 17, 2017, 5 pages.
European Communication Pursuant to Article 94(3) EPC issued in EP14790592.1 and dated May 30, 2017, 4 pages.
International Search Report and Written Opinion of the International Searching Authority dated Apr. 12, 2013, which issued during prosecution of International Application No. PCT/EP2013/054592 which corresponds to the present application.
International Preliminary Report on Patentability dated Sep. 29, 2015 during prosecution of International Patent Application No. PCT/EP2014/056381, 8 pages.
NCBI Reference Sequence NM_198253.2, *Homo sapiens* telomerase reverse transcriptase (TERT), transcript variant 1, mRNA, 8 pages.
Velders, M. P. et al., "Defined Flanking Spacers and Enhanced Proteolysis Is Essential for Eradication of Established Tumors by an Epitope String DNA Vaccine", Journal Immunology (2001), vol. 166, pp. 5366-5373.
Wang, Qingmin et al., "Improved Cellular Immune Response Elicited by a Ubiquitin-Fused DNA Vaccine Against *Mycobacterium tuberculosis*", DNA and Cell Biology (2012), vol. 31, No. 4, pp. 489-495.
English Translation of Japanese Office Action Issed in JP2016-504709, dated Oct. 10, 2017, 5 pages.
English Translation of Japanese Office Action Issed in JP2016-504710, dated Oct. 10, 2017, 6 pages.
Cadile, C. D. et al., "Telomerase activity as a marker for malignancy in feline tissues", American Journal of Veterinary Research (2001), vol. 62, No. 10, pp. 1578-1581.
Huang, J. J. et al., "Ectopic Expression of a COOH-terminal Fragment of the Human Telomerase Reverse Transcriptase Leads to Telomere Dysfunction and Reduction of Growth and Tumorigenicity in HeLa Cells", Cancer Research (2002), vol. 62, pp. 3226-3232.
Huo, L. et al., "Cancer Immunotherapy Targeting the Telomerase Reverse Transcriptase" Cellular and Molecular Immunology (2006), vol. 3, No. 1, pp. 1-9.
Impellizeri, J. A. et al., "Electro-gene-transfer as a new tool for cancer immunotherapy in animals", Veterinary and Comparative Oncology, Short Communication, (Oct. 24, 2012), vol. 12, issue 4, pp. 1-9; DOI: 10.1111/vco.12006.
Ng, SSM et al., "A novel glioblastoma cancer gene therapy using AAV-mediated long-term expression of human TERT C-terminal polypeptide", Cancer Gene Therapy (2007), vol. 14, pp. 561-572.

* cited by examiner

```
HindIII        > Ubiquitin initiator methionine
  1 AAGCTTGCCGCCATGCAGATTTTCGTCAAAACCCTCACCGGCAAGACCATCACATTGGAAGTGGAACCCAGTGATACTATCGAAAATGTT   90
  1               M  Q  I  F  V  K  T  L  T  G  K  T  I  T  L  E  V  E  P  S  D  T  I  E  N  V    30

91 AAAGCCAAAATCCAGGATAAGGAGGGCATTCCTCCTGACCAGCAGAGACTTATTTTCGCAGGCAAACAGCTGGAGGACGGCAGAACATTG  180
 31 K  A  K  I  Q  D  K  E  G  I  P  P  D  Q  Q  R  L  I  F  A  G  K  Q  L  E  D  G  R  T  L    60
                                                         Ubiquitin >< dog telomerase
181 TCTGACTACAACATCCAGAAAGAGAGCACACTTCACTTGGTTCTCCGCCTTCGCGGAGGACGGGCCCTTCGTGGCTCAGTGTCTGGTGTGT  270
 61 S  D  Y  N  I  Q  K  E  S  T  L  H  L  V  L  R  L  R  G  G  R  A  L  V  A  Q  C  L  V  C    90

271 GTCCCATGGGGAGCACGGCCTCCACCAGCGCCCCTGCTTTAGACAGGTCAGTTGCCTCAAGGAGCTCGTGGCCAGGGTGGTTCAGAGA    360
 91 V  P  W  G  A  R  P  P  A  A  P  C  F  R  Q  V  S  C  L  K  E  L  V  A  R  V  V  Q  R      120
                                       dog telomerase >< cat telomerase
361 CTCTGCGAGCGGGGTGCCCGGaatgtgctggcctttggattcgctctgcttgacggtgcaggggaggcccaccagtggtgttcaccaca   450
121 L  C  E  R  G  A  R  N  V  L  A  F  G  F  A  L  L  D  G  A  R  G  P  P  V  V  F  T  T      150
```

FIGURE 1A

```
451  tctgtgcgcagttatctgccaaacacagttaccgagactctgcgcgggatcaggagcctgcttgctgctcaggcgcgtcggtgacgac  540
151   S   V   R   S   Y   L   P   N   T   V   T   E   T   L   R   G   S   G   A   W   G   L   L   R   R   V   G   D   D    180

541  gtgcttgccacttgctcaccggtgcgcccttttacgtcctcgtcctgtagttgcgctccctagtcctggttgtgtggacccccctgtatgat  630
181   V   L   A   H   L   T   R   C   A   L   Y   V   L   V   A   P   S   C   A   Y   Q   V   C   G   P   P   L   Y   D    210

631  ctctgtgctccagcagccactaggcccctgctacttccggctacctggcccatagggcccggcaccagaatggatctgcggccacaggcaggcaggcacgc  720
211   L   C   A   P   A   A   T   R   P   L   A   T   S   G   H   R   P   G   T   R   M   D   L   R   P   T   R   Q   A   R    240

721  aacgcggcggcacggcgagaagaggtgctgccgcagctcctctttggcaaagacatgatgttaaaacccagagcca  810
241   N   A   G   A   R   R   R   R   G   A   G   G   S   S   P   P   L   A   K   R   P   R   H   D   V   K   T   P   E   P    270

811  gaaagaggacccgcatcccccagctcacggcgcgtcatggagggcgaacctgcaggaggggaacctgcggcgcgtcacctcagcc  900
271   E   R   G   P   A   S   P   S   S   R   H   P   P   G   R   A   H   G   L   S   G   G   E   P   G   A   V   T   S   A    300

901  cggcgccctgccgaggcaaatagcggcgaggggcgaggacccctgactgacttctgcgcgcacagctgtcccgcccacaggga  990
301   R   A   A   A   E   A   N   S   G   E   G   G   P   P   G   T   R   L   T   S   A   G   A   Q   L   S   R   P   Q   G    330

991  gtgccctgagtcatctgagcatcccgaaacaaagcactttctttactgcccgggtggaaagaacggctggagaccatccttcttgctc  1080
331   V   P   L   S   H   L   S   H   P   E   T   K   H   F   L   Y   C   P   G   G   K   E   R   L   R   P   S   F   L   L    360

1081 agcgctttgcgcccttcctgacagggccagaaccctctccttggaagctatctcccctggatctaaatcccctaggccgggtgcagctagg  1170
361   S   A   L   R   P   S   L   T   G   A   R   T   L   L   E   A   I   F   L   G   S   K   S   P   R   P   G   A   A   R    390

1171 cggactaggaggctcactgtccctgccagatatttggagaatgccgccctgttcaggagctccttgctaaccacgccgcctgccctacgacgcc  1260
391   R   T   R   R   L   P   A   R   Y   W   R   M   R   P   L   F   R   E   L   L   A   N   H   A   R   C   P   Y   D   A    420

1261 cttctgcgcactcactgtcccctgccactcctccgccgagggatctagtagaggcgtggtggcggtgctgcggttgtgccctc  1350
421   L   L   R   T   H   C   P   L   R   A   P   A   E   G   S   S   R   G   V   G   G   A   G   G   C   A   L    450

1351 ggccggcctccaggtgcccaCAGGAACAGACCGATTCAACCCGCCTGTGCGAGCTCCTGAGCACAGTAGCCATGGCAGTGTAT  1440
451   G   R   P   P   G   A   P   Q   E   Q   T   D   S   T   R   L   V   Q   L   R   Q   H   S   S   P   W   Q   V   Y    480

1441 GCTTTCTTCGGCCTTGTCTGTCCCTCGTGCCGCGCCACAGAAGACGCTTTTGCGGAATGTGAAA  1530
481   A   F   L   R   A   C   L   C   R   L   V   P   A   G   L   W   G   S   H   N   R   R   F   L   R   N   V   K    510

1531 AAGTTCGTGTCCCTGGGAAAGCACGCTAAACTGTCATTGCAGGAGCTGACCTGGAAGATGCGGGTGCAGGATTGTGCATGGCTGAGGGGC  1620
511   K   F   V   S   L   G   K   H   A   K   L   S   L   Q   E   L   T   W   K   M   R   V   Q   D   C   A   W   L   R   G    540
```

FIGURE 1A cont.

```
1621 TCTCCCGGAGCCCGCTGCGTCCCAGCCGCCGAACACAGAGCGGGCGGAGGAGGTGCTGGCAAAGCTCTTGTGCTGGCTGATGGGAACCTAC 1710
 541  S  P  G  A  R  C  V  P  A  A  E  H  R  R  R  E  E  V  L  A  K  L  L  C  W  L  M  G  T  Y   570

1711 GTGGTCGAACTGCTGAAATCTTTTTTCTATGTCACTGAGACTACATTCCAGAAGAATCGCCTGTTCTTTTACCGGAAAAGATCTGGTCC 1800
 571  V  V  E  L  L  K  S  F  F  Y  V  T  E  T  F  Q  K  N  R  L  F  F  Y  R  K  R  I  W  S   600

1801 CAGCTTCAGAGCATTGGCATCCGGCAGCATTTTAACTCTGTTCACCTGAGGGAGCTGAGCGAGGCAGAAGTGAGGCGCCATCAGGAGGCC 1890
 601  Q  L  Q  S  I  G  I  R  Q  H  F  N  S  V  H  L  R  E  L  S  E  A  E  V  R  R  H  Q  E  A   630

1891 CGCCCCACTCTGCTTACCTCCAAGCTGCGGTTCCTGCCTAAACCATCAGGTCTGAGACCCATTGTCAACATGGATTACGTGGTGGGCGCC 1980
 631  R  P  T  L  L  T  S  K  L  R  F  L  P  K  P  S  G  L  R  P  I  V  N  M  D  Y  V  V  G  A   660

1981 AGAACATTCAGAAGACAAAAGGTTCGGCATCCACAGGTTAAAAACCTGTTTTCTGTTTCTGAACTACGAAAGGCCAGGAGG 2070
 661  R  T  F  F  R  R  D  K  K  V  R  H  L  T  S  Q  V  K  N  L  F  S  V  L  N  Y  E  R  A  R  R   690

2071 CCATCACTGCTGGGTGCCAGTGTGCTGGGAATGGACGATATTCACAGAGTCTGGCGGAGCTTCGTGCTTCGGGTGAGAGCTCAGGACCCC 2160
 691  P  S  L  L  G  A  S  V  L  G  M  D  D  I  H  R  V  W  R  S  F  V  L  R  V  R  A  Q  D  P   720

2161 GCCCCACAGTTGTCTATTTTGTCAAGGTCGATGTGACTGGCGCATTACGCTGTGGTGCAGCGCACCGCACAGGCCACGTGAGGAAATCCTTCAAGCGG 2250
 721  A  P  Q  L  Y  F  V  K  V  D  V  T  G  A  Y  D  A  L  P  Q  D  K  L  V  E  V  I  A  N  V   750

2251 ATCCGCCCCCAGGAAAATACATACTGCGTCGTGCGGCATTACGCTGTGGTGGTCCAGCGCACCGCACAGGGCCACGTGAGGAAGAACTTCAAGCGG 2340
 751  I  R  P  Q  E  N  T  Y  C  V  R  H  Y  A  V  V  Q  R  T  A  Q  G  H  V  R  K  S  F  K  R   780

2341 CATGTGTCCACCTTCGTCGACCTCCAGCCCTATATGCGACAGTTCGTGGAGCACCTGCAGGAAACTTCAAGCCTTAGGGATGCCGTTGTT 2430
 781  H  V  S  T  F  V  D  L  Q  P  Y  M  R  Q  F  V  E  H  L  Q  E  T  S  S  L  R  D  A  V  V   810

2431 ATCGAGCAGAGTTCTAGTCTCAACGAGACCGGACAGTCTCTTTTCCACCTCTTTCTGAGGCTCGTGCATAATCATGTCATCCGCATTGGA 2520
 811  I  E  Q  S  S  L  N  E  T  G  H  S  L  F  H  L  F  L  R  L  V  H  N  H  V  I  R  I  G   840

2521 GGAAAATCTTATGTTCAGTGCCAGGGCATCCCTCAGGGTTCTATCCTGTCAACTCTGCTCTGTTACGGCGATATGGAAAGT 2610
 841  G  K  S  Y  V  Q  C  Q  G  I  P  Q  G  S  I  L  S  T  L  L  C  Y  G  D  M  E  S   870

2611 AGGCTTTTCTCAGGAATCCAGCAGGACGGCGTCCTGCTGCGTCTTCTTCTGGTGACACCTCACCTGGCACAGGCCCAGGCCTTCCTG 2700
 871  R  L  F  S  G  I  Q  Q  D  G  V  L  L  R  L  F  L  L  V  T  P  H  L  A  Q  A  F  L   900

ΔVDD >< (deleted catalytic aspartic acid (D) residues)
```

FIGURE 1A cont.

```
2701 CGCACACTGGTGAGCGGAGTGCCTGAGTACGGCCCAACCTGCAGAAGACAGCCGTGAATTTTCCAGTGGACACCGGTGCTCCA 2790
 901  R  T  L  V  S  G  V  P  E  Y  G  C  T  A  N  L  Q  K  T  A  V  N  F  P  V  D  T  G  A  P   930

2791 GGCTCCGCCGCACCTCTGCAGTTGCCCGCACATTGTCTCTTTCCTTGGTGTGGCCGACTTTGGAAGTCTTTTGC 2880
 931  G  S  A  A  P  L  Q  L  P  A  H  C  L  F  P  W  C  G  L  L  D  T  R  T  L  E  V  F  C   960

2881 GATTACTCCAGCTATGCACAGACTATCAGGAGCCATTAGGAGGCCTGACATTCAGCAGGCACACGGCCCGCAATATGAGGAGAAAGTTG 2970
 961  D  Y  S  S  Y  A  Q  T  S  I  R  S  S  L  T  F  S  Q  G  T  R  P  G  R  N  M  R  R  K  L   990

2971 CTCGCCGTTATGAGACTCAAGTGCTGTGCAGTCTTTCTTGATCTGCAGGTCAATTCTATTCATACCGTTTACACCAACATCTATAAAATT 3060
 991  L  A  V  M  R  L  K  C  C  A  V  F  L  D  L  Q  V  N  S  I  H  T  V  Y  T  N  I  Y  K  I  1020

3061 TTCCTGCTCCAGGCATATAGATTCACGCTGTTGCAGTTCCCATTCAATCAGCCCGTTCGGAAGAACCCAGTTCTTTCTTCTCAGG 3150
1021  F  L  Q  A  Y  R  F  H  A  C  V  L  Q  F  P  F  N  Q  P  V  R  K  N  P  S  F  F  L  R  1050

3151 GTTATTGCTGATACCGCTAGTCGCTGTTACTCCCCGTTAAGGCCAAGAACACAGGACTTTCATTGGGTGCTAAAGGCGCCAGTGGACCT 3240
1051  V  I  A  D  T  A  S  R  C  Y  S  L  L  K  A  K  N  T  G  L  S  L  G  A  K  G  A  S  G  P  1080

3241 TTCCCCTTCTGAAGCCGCTCGGTGGCTCTGTTTGCACGCATTCCTTTCTGAAGTTGGCTAGACACAGCTCTACTTACAGATGCCTTCTGGGC 3330
1081  F  P  S  E  A  A  R  W  L  C  L  H  A  F  L  L  K  L  A  R  H  S  S  T  Y  R  C  L  L  G  1110

3331 CCCCTTAGAGccgcaaagccagctcaggagacagcccagtgccacggggtaccctgaccgggtacccctgaggcagcaagccctgcctgcca 3420
1111  P  L  R  A  A  K  A  Q  L  R  R  Q  L  P  R  A  T  L  D  A  L  E  A  A  A  S  P  G  L  P  1140 cat telomeras                                                          XhoI     XbaI
3421 GcagatttcggaccattctggataAAGGGTCAAGACAATTCTGCAGATATCCAGATATCCAGATACACAGTGGGCGCGCTCGAGTCTAGAGGGCCCCGCGG 3510
1141  A  D  F  R  T  I  L  D  K  G  Q  D  N  S  A  D  I  Q  H  S  G  G  R  S  S  L  E  G  P  R  1170

V5 tag                     >   <    His6x tag      >
3511 TTCGAAGGTAAGCCTATCCCTAACCCTCTCCTCGGTCTCGATTCTACGCGTCATCATCACCATCACCATTGA 3588
1171  F  E  G  K  P  I  P  N  P  L  L  G  L  D  S  T  R  T  G  H  H  H  H  H  H  *  1195
```

FIGURE 1A cont.

```
HindIII     > Ubiquitin initiator methionine
AAGCTTGCCGCCATGCAGATTTTCGTCAAGACCCTCACCGGCAAGACCATCACATTGGAAGTGGAACCCAGTGATACTATCGAAAATGTT     90
            M  Q  I  F  V  K  T  L  T  G  K  T  I  T  L  E  V  E  P  S  D  T  I  E  N  V        30

AAAGCCAAAATCCAGGATAAGGAGGGCATTCCTCCTGACCAGCAGAGACTTATTTTCGCAGGCAAACAGCTGGAGGACGGCAGAACATTG    180
 K  A  K  I  Q  D  K  E  G  I  P  P  D  Q  Q  R  L  I  F  A  G  K  Q  L  E  D  G  R  T  L      60
                                                ubiquitin >< dog telomerase
TCTGACTACAACATCCAGAAAGAGAGCACACTTCACTTGGTTCTCCGCCTTGTTCTCCGTGGTGGCCTCAGTGTCTGGTGTGT            270
 S  D  Y  N  I  Q  K  E  S  T  L  H  L  V  L  R  G  G  R  A  L  V  A  Q  C  L  V  C             90

GTCCCATGGGGAGCACGGCCTGCCCCGGAGCCCTCCAAGAGCTCAGTTGCCTCAAGGAGCTCGTGGCCAGGGTGGTTCAGAGA            360
 V  P  W  G  A  R  P  P  A  A  P  C  F  R  Q  V  S  C  L  K  E  L  V  A  R  V  V  Q  R         120

CTCTGCGAGCGGGGTGCCCGGAACGTCCTCGCTTTTGGATTCGCACTGCTGGACGGCGCTCGCGGAGGCCCACCCGTGGCCTTTACAACC    450
 L  C  E  R  G  A  R  N  V  L  A  F  G  F  A  L  L  D  G  A  R  G  G  P  P  V  A  F  T  T     150

AGCGTGCGGTCATACCTGCCCAACACTGTGACAGAGACACTGAGAGGCTCCGGCGCTTGGGGCTTGTTGAGGCGCGTTGGCGACGAT       540
 S  V  R  S  Y  L  P  N  T  V  T  E  T  L  R  G  S  G  A  W  G  L  L  R  R  V  G  D  D        180

GTGTTGACACACTTGCTCGCCAGGTGCGCACTTTACCTGCTGGTCGCCCCAAGTTGCGCTGCCTACCAGGTGTGCGGACCTCCTTTGTACGAC    630
 V  L  T  H  L  L  A  R  C  A  L  Y  L  L  V  A  P  S  C  A  Y  Q  V  C  G  P  P  L  Y  D     210

CTCTGTGCCCCACTCTTTGCCACTGCCTGAGCCTGCAGCCCCTGGAGCTGGCGCCTCC                                   720
 L  C  A  P  A  S  L  P  L  P  A  P  G  L  P  G  L  P  G  L  G  A  G  A  S                   240

GCAGATCTCAGGCCTACCCGCCAGGCACAGAATAGCGGAGCCCGGTAGCGCCGGGTCTCCCCTGGCTAAAAGA                    810
 A  D  L  R  P  T  R  Q  A  Q  N  S  G  A  R  R  R  G  S  P  G  S  G  V  P  L  A  K  R      270
```

FIGURE 1B

```
CCACGGAGGTCAGTTGCTTCCGAACCCGAGCTCCTTCCCAGAGCAGCCCAGCCACCTGTGTCTGAGGCTCCAGCA      900
 P  R  R  S  V  A  S  E  P  E  R  G  A  H  R  S  F  P  R  A  Q  Q  P  P  V  S  E  A  P  A        300

GTCACACCCCGCTGTGGCCGCCAGCCCCTGCCGCTCCATGGAAGGAGGACCCCCACTACCCCGCTTGCCACCCCTAC      990
 V  T  P  A  V  A  A  S  P  A  A  S  W  E  G  G  P  P  G  T  R  P  T  T  P  A  W  H  P  Y       330

CCTGGACCCCAGGGCGGTCCCCTCATGATCCTCACCCAAGCCGGTTCCTGTACTGCAGCGGAGGTAGAGAACGCTTGCGCCCA     1080
 P  G  P  Q  G  V  P  H  D  P  A  H  P  E  T  K  R  F  L  Y  C  S  G  G  R  E  R  L  R  P       360

AGTTTTCTGCTCAGCGCCCTGCCTCCAACTCTTTCCGGAGCCCGGAARKLVETIFLGSAPQKP     1170
 S  F  L  L  S  A  L  P  P  T  L  S  G  A  R  K  L  V  E  T  I  F  L  G  S  A  P  Q  K  P       390

GGAGCCGCTAGGCGGATGCGGATCGCTGCCTGCAGACTGCCTGCGCATGCGCCCACTCTTTCAGGAGCTGCTGGGAAATCATGCAAGGTGC     1260
 G  A  A  R  R  M  R  R  L  P  A  R  Y  W  R  M  R  P  L  F  Q  E  L  L  G  N  H  A  R  C       420

CCCTATCGGGCTCTGCTTCGGATCCACTGTCCACTGAGAGCTATGGCAGCAAAGGAAGTGGAAACCAGGCCCATAGAGGAGTCGGT     1350
 P  Y  R  A  L  L  R  T  H  C  P  L  R  A  M  A  A  K  E  G  S  N  Q  A  H  R  G  V  G       450 dog TERT >< cat TERT
ATCTGTCCACTGGAGCGCCCCCCGTTGCTGCCCCAGGAACACGATTCAACCCGCTCTGTGCAGCTCCTGAGGCAGCACAGTAGCCCA     1440
 I  C  P  L  E  R  P  V  A  A  P  Q  E  Q  T  D  S  T  R  L  V  Q  L  L  R  Q  H  S  S  P       480

TGGCAGGTGTATGCTTTTCTTCGCGCCTTGTGTCCGCTTGTGCCCGCAGGCCACAACAGAAGACGCTTTTTG     1530
 W  Q  V  Y  A  F  L  R  A  C  L  C  R  L  V  P  A  G  L  W  G  S  G  H  N  R  R  R  F  L       510

CGGAATGTGAAAAAGTTCGTGTCCCTGGGAAAGCACGCTAAACTGTCATTGCAGGAGCTGACCTGGAAGATGCGGGTGCAGGATTGTGCA     1620
 R  N  V  K  K  F  V  S  L  G  K  H  A  K  L  S  L  Q  E  L  T  W  K  M  R  V  Q  D  C  A       540

TGGCTGAGGGCTCTCCCGGAGCCGCTCCGTCCCAGCCGCCGAACACGACGGCGCGAGGAGGTGCTCGCAAAGCTCTTGTGCTGGCTG     1710
 W  L  R  G  S  P  G  A  R  C  V  P  A  A  E  H  R  R  R  E  E  V  L  A  K  L  L  C  W  L       570

ATGGGAACCTACGTGGTCGAAATCTTTTTCTATGTCACTGAGACTACATTCCAGAAGAATGCCTGTTCTTTTACCGGAAA     1800
```

FIGURE 1B cont.

```
M   G   T   Y   V   E   L   L   K   S   F   F   Y   V   T   E   T   T   F   Q   K   N   R   L   F   F   Y   R   K                                600
AGGATCTGGTCTCCAGCTTCAGAGCATTGGCATCCGGCAGCATTTAACTCTGTCACCTGAGGAGCTGAGCGAGGAGCAGAAGTGAGGCGC                                                     1890
R   I   W   S   Q   L   Q   S   I   G   I   R   Q   H   F   N   S   V   H   L   R   E   L   S   E   A   E   V   R   R                            630
CATCAGGAGGCCAGGCCCCGCCACTCTGCTTACCTCCAAGCTCTGCCTAAACCATCAGGTCTGAGACCATTGTCAACATGGATTAC                                                         1980
H   Q   E   A   R   P   T   L   L   T   S   K   L   R   F   L   P   K   P   S   G   L   R   P   I   V   N   M   D   Y                            660
GTGGTGGGCGCCAGAACATTCAGAAGAGACAAAAAGGTTCGGCATCTCACCTCACAGGTTAAAAACCTGTTTTCTGTTCTGAACTACGAA                                                     2070
V   V   G   A   R   T   F   R   R   D   K   K   V   R   H   L   T   S   Q   V   K   N   L   F   S   V   L   N   Y   E                            690
AGGGCCAGGAGGCCATCACTGCTGGGTGCCAGTGTGTGCTGGGAATGACGATATTCACAGAGTCTGGCGGAGCTTCGTGCTTCGGGTGAGA                                                    2160
R   A   R   R   P   S   L   L   G   A   S   V   L   G   M   D   D   I   H   R   V   W   R   S   F   V   L   R   V   R                            720
GCTCAGGACCCGCCCCCACAGTTGTATTTTGTCAAGGTCGATGTGACTGGCGCTTATGACGCTCTCCCTCAGGACAAATTGGTGGAGGTG                                                     2250
A   Q   D   P   A   P   Q   L   Y   F   V   K   V   D   V   T   G   A   Y   D   A   L   P   Q   D   K   L   V   E   V                            750
ATCGCTAATGTCATCCGCCCCCAGGAAAATACATACTGCGTGCGCCATTACGCTGTGGTGCAGCGCACCGCACAGGGCCACGTGAGGAAA                                                     2340
I   A   N   V   I   R   P   Q   E   N   T   Y   C   V   R   H   Y   A   V   V   Q   R   T   A   Q   G   H   V   R   K                            780
TCCTTCAAGCGGCATGTGTCCAGAGTTCTAGCTCAACGAGACCCAGTTTGTGGAGCACCTCTTTCTGAGGCTCGTGCATAATCATGTC                                                       2430
S   F   K   R   H   V   S   T   F   V   D   L   Q   P   Y   M   R   Q   F   V   E   H   L   Q   E   T   S   S   L   R                            810
GATGCCGTTGTTATCGAGCAGTTCTAGCTCCAACGAGACCGGCCATCCCCTTCTATCCTGTCAACTTCAGGGTTCTATCCTGTCATAATCATGTC                                                2520
D   A   V   V   I   E   Q   S   S   L   N   E   T   G   H   S   L   F   H   L   F   L   R   L   V   H   N   H   V                                840
ATCCGCATTGGAGGAAAATCTTATGTTCAGTGCCAGGGCATCCCTCAGGGTTCATCCTGTCTTCTGCTCCTTGTGTTACGGC                                                              2610
I   R   I   G   G   K   S   Y   V   Q   C   Q   G   I   P   Q   G   S   I   L   S   T   L   L   C   S   L   C   Y   G                            870
                                (deleted catalytic aspartic acid (D) residues) >< ΔVDD
GATATGGAAAGTAGGCTTTTCTCAGGAATCCAGGATGGTGTTCTGCGGCTGTTTCTTGACACCTCACCTGGTGACACCTGGCACAGGCC                                                      2700
D   M   E   S   R   L   F   S   G   I   Q   Q   D   G   V   L   R   L   F   L   L   V   T   P   H   L   A   Q   A                                900
```

FIGURE 1B cont.

```
CAGGCCTTCCTGCGCCACACTGGTGAGCGGAGTGCCTGAGTACGGCTGTACCGCCAACCTGCAGAAGACAGCCGTGAATTTTCCAGTGGAC  2790
 Q  A  F  L  R  T  L  V  S  G  V  P  E  Y  G  C  T  A  N  L  Q  K  T  A  V  N  F  P  V  D   930
ACCGGTGCTCCAGGCTCCGCGCCAGTGCAGTTGCCCGCACCTCTGCAGTGTCTCTTCCTTGGTGTGGCCTGCTCCTGGACACCCGGACTTTG  2880
 T  G  A  P  G  S  A  A  P  L  Q  L  P  A  H  C  L  F  P  W  C  G  L  L  D  T  R  T  L     960
GAAGTCTTTTGCGATTACTCCAGCTATGCACAGACATCCATTAGGAGCAGCCTGACATTCAGCCAGGGCACACGGCCCGGCCGCAATATG  2970
 E  V  F  C  D  Y  S  S  Y  A  Q  T  S  I  R  S  S  L  T  F  S  Q  G  T  R  P  G  R  N  M   990
AGGAGAAAGTTGCTCGCCGTTATGAGAGACTCAAGTGCTGTGCCGTTTTCTTGATCTGCAGGTCAATTCTATTCATACCGTTTACACCAAC  3060
 R  R  K  L  A  V  M  R  L  K  C  C  A  V  F  L  D  L  Q  V  N  S  I  H  T  V  Y  T  N    1020
ATCTATAAAATTTCCTGCTCCAGGCATATAGATTCCAATCAGCCGTTCCCATTCAATCAGCCGTTCGGAAGAACCCCAGT  3150
 I  Y  K  I  F  L  Q  A  Y  R  F  H  A  C  V  L  Q  F  P  F  N  Q  P  V  R  K  N  P  S    1050
TTCTTTCTCAGGGTTATTGCTGATACCGCCTCCGATACTGCTTACTCCCGCTGTTACTCCCTGTTAAGGCCAAGAACACAGGACTTTCATTGGGTGCTAAAGGC  3240
 F  F  L  R  V  I  A  D  T  A  S  R  C  Y  S  L  L  K  A  K  N  T  G  L  S  L  G  A  K  G  1080
                                                            cat TERT ><  dog TERT
GCCAGTGGACCTTTCCCTTTCCCTTCTGAAGCCGCTCGGTGGCTCTGTTTGCACGCAGTTGGCTAGACACAGCTCTACTTACAGA  3330
 A  S  G  F  F  P  S  E  A  A  R  W  L  C  L  H  A  F  L  L  K  L  A  R  H  S  S  T  Y  R  1110
TGCCTTCTGGGCCCCCTTAGAGCTGCTAAGGCTCATCTGTCAAGACAGCTCCCAAGAGAGGCACTCTGCCGCCACTGGAGGCCGCAGCCGAC  3420
 C  L  L  G  P  L  R  A  A  K  A  H  L  S  R  Q  L  P  R  G  T  L  A  A  L  E  A  A  A  D  1140
                                                                  influenza A A2 epitope  >
CCCTCCCTCACTGCAGATTTAAGACTATTCTCGATACCGAGCTTAAGTTGCAGACTACGAGGGACGCCTGATTCAGAATAGCCTGACA  3510
 P  S  L  T  A  D  F  K  T  I  L  D  T  E  L  K  L  S  D  Y  E  G  R  L  I  Q  N  S  L  T  1170
   V5 tag       >         XbaI
GGCAAACCCATTCCTAATCCCCTGTTTGGATTCCACATGATAATCTAGA 3564
 G  K  P  I  P  N  P  L  G  L  D  S  T  *  *        1184

CANCER VACCINE FOR CATS

This application is the U.S. National Phase of International Patent Application Serial No. PCT/EP2014/056380, filed on Mar. 28, 2014, which claims priority to European Patent Application No. EP 13305404.9, filed on Mar. 28, 2013, both of which applications are herein incorporated by reference in their entirety.

BACKGROUND OF THE INVENTION

Like their human counterparts, cats that live in developed countries have seen their life expectancy consistently prolonged. Therefore, the global burden of cancers continues to increase largely because of the aging and growing of the cat population.

Cancer incidence rate is estimated to 77 per 10,000 cats. Lymphomas and tumors of the sub-cutaneous tissues, and especially the complex feline fibrosarcoma, are the most frequent of the feline cancerous diseases (Vascellari et al. 2009).

The panel of treatments available against veterinary cancer is substantially reduced compared with those available in human oncology.

Surgery remains the best way to treat animal tumors. This method presents the advantage of being accessible for many veterinarians, and, in many cases, it can be curative. However, to be curative, surgery must be bold and in some cases the tumor is too large, too dispersed or just not accessible enough to be entirely removed. If not totally curative, surgery can still be a palliative solution to improve animal's comfort and prolonged its life expectancy.

Radiotherapy is another important means to treat certain types of cancers in the veterinary field. It is of particular interest for tumors which are hardly accessible for surgery like cerebral tumors. Furthermore, recent studies in humans have demonstrated that ionizing radiation (IR) could act as an immunomodulator by inducing substantial changes in the tumor microenvironment, including triggering an inflammatory process. Furthermore, the cost and the availability of the material make access to radiation therapy complicated for companion animals.

Chemotherapy is more and more used in animal oncology (Marconato 2011). Taking advantages of medical advances in human cancer therapy, there are more and more molecules available like vincristine, cyclophosphamide, carboplatin or cisplatin, to treat companion animals. In the veterinary field, anticancer drugs are particularly used in the treatment of tumors derived from hematopoietic tissue (lymphomas, leukemias). For example the CHOP protocol, combining cyclophosphamide, doxorubicin, vincristine and prednisone is currently used in the treatment of numerous lymphomas (Chun 2009). Chemotherapeutic agents can be particularly efficient in prolonging the life span of a cancerous animal from a few weeks to several months. Interestingly, the side effects dreaded by human patients, such as vomiting, diarrhea, hair loss, are usually less frequent in companion animals. Unfortunately, most of the time chemotherapy is not curative in pets and the tumor often escapes from treatment.

Therefore, just as in human medicine, targeted therapies are in development in veterinary medicine. Other treatments, including immunotherapies, are under investigation. These immunotherapeutic treatments are all based on the fact that it is possible to activate the immune system of the host against cancer cells.

The relationship between the host immune system and cancer is dynamic and complex. Each type of tumor cells harbors a multitude of somatic mutations and epigenetically deregulated genes, the products of which are potentially recognizable as foreign antigens by immune cells (MUC-1, β-catenin, telomerase . . . ) (Fridman et al. 2012). Growing tumors contain infiltrating lymphocytes called TILs (Tumor Infiltrating Lymphocytes). These killer cells are often ineffective at tumor elimination in vivo but can exert specific functions in vitro, that is to say outside the immunosuppressive tumor microenvironment (Restifo et al. 2012). This is because the tumor stroma contains many suppressive elements including regulatory T cells (Tregs) and myeloid-derived suppressor cells (MDCs); soluble factors such as interleukin 6 (IL-6), IL-10, vascular endothelial growth factor (VEGF), and transforming growth factor beta (TGFβ that down modulate antitumor immunity (Finn 2008, Hanahan and Weinberg 2011). Consequently, the choice of a pertinent tumor associated antigen (TAA) and the bypass of cancer associated immunosuppression are two critical points for a therapeutic vaccine to succeed (Disis et al. 2009).

Recent introduction of active cancer immunotherapy (also referred to cancer vaccines) in the clinical cancer practice emphasizes the role of immune responses in cancer prognosis and has led to a growing interest to extend this approach to several human and companion animal cancers (Dillman 2011, Topalian et al. 2011) (Jourdier et al. 2003).

In this context, there is still a need for an innovative cancer vaccine strategy for cats, which would overcome the challenge of breaking tolerance and inducing an immune response in the animal.

SUMMARY OF THE INVENTION

The inventors now propose a cancer vaccine strategy for cats, based on the telomerase reverse transcriptase (TERT).

A subject of the invention is thus an immunogenic composition comprising a nucleic acid that comprises a sequence encoding (i) a cat TERT deprived of telomerase catalytic activity, or (ii) a fragment thereof. The nucleic acid is preferably DNA, preferably in form of a plasmid.

In a preferred embodiment, the nucleic acid that comprises a sequence encoding a cat telomerase reverse transcriptase (TERT) deprived of telomerase catalytic activity, wherein the sequence encoding catTERT is further deprived of a nucleolar localization signal.

In a particular embodiment, the nucleic acid further comprises a non-cat TERT antigenic fragment.

A further subject of the invention is a nucleic acid that comprises a sequence encoding (i) a cat TERT deprived of telomerase catalytic activity, or (ii) a fragment thereof, and optionally further comprises a non-cat TERT antigenic fragment.

The immunogenic composition or the nucleic acid is useful in triggering an immune response in a cat, against cells that overexpress telomerase, such as dysplasia cells, tumor cells, or cells infected by an oncovirus.

The immunogenic composition or the nucleic acid is thus particularly useful in treating a tumor in a cat, preferably by intradermal or intramuscular route.

Such treatment can be referred to as an active immunotherapy or a therapeutic vaccination, as it triggers an immune response against the tumor, especially a cytotoxic CD8 T cell response, along with a specific CD4 T cell response.

The invention makes it possible to induce dTERT specific responses in cats with neoplasias and so can be used for immunotherapeutic treatments of the neoplasias in a clinical setting.

The invention is also useful to induce dTERT specific responses in healthy cats that could be at risk for cancer, e.g. by genetic predisposition, or in healthy cats from a certain age (e.g. of 12 years or more, preferably more than 14 years old) so as to prevent the onset of cancer.

Generally speaking, the treatment of the invention may induce long term immune memory responses in healthy dogs, dogs at risk of developing a cancer and those presenting a cancer.

BRIEF DESCRIPTION OF THE FIGURES

The plasmid pUF2 encodes a cat TERT (cTERT) protein comprising about 95% from the cat TERT and about 5% from the dog TERT sequence. Exon 1 encoding the extreme amino terminus of the cat telomerase genes remains unknown. It is estimated that 47 amino acids (141 bases) are missing. The nucleotide sequence encoding 3 key amino acids in the catalytic site of the protein have been deleted (VDD). Moreover, the sequence controlling the importation into the nucleoli (Nucleolar addressing signal) has been deleted (nucleotide sequence encoding 47 first Amino Acids in the N ter sequence of cTERT protein). The DNA sequence encoding the human ubiquitin has been added upstream the cTERT sequence. The presence of the ubiquitin protein enhances the addressing of the cTERT protein to the proteasome and increases class I presentation of derived peptides. However, as the human and cat ubiquitin sequences are identical at the protein level, there is no biological incompatibility. Downstream the cTERT sequence, the sequence of the V5 peptide of the flu was inserted to facilitate the detection of the protein Nucleotides 1-6 HindIII restriction site for subcloning
Nucleotides 13-240 ubiquitin
Nucleotides 241-438 dog TERT (5.5% of TERT sequences)
Nucleotides 439-3444 cat TERT Nucleotides 3517-3558 SV5 V5 tag
Nucleotides 3586-3588 two stop codons
Nucleotides 3495-3500 Xba1 restriction site for subcloning
Nucleotides 2655-2656 inactivating deletion of 9 bp encoding VDD residues

The plasmid pCDT encode the cat/dog hybrid TERT (hyTERT) comprising 54.4% from the cat TERT and 35.9% from the dog TERT sequence. The nucleotide sequence encoding 3 key amino acids in the catalytic site of the protein have been deleted (VDD). Moreover, the sequence controlling the importation into the nucleoli (Nucleolar addressing signal) has been depleted (nucleotide sequence encoding 45 first Amino Acids in the Nterm sequence of hyTERT protein). The DNA sequence encoding the human ubiquitin has been added upstream the hyTERT sequence. The presence of the ubiquitin protein enhances the addressing of the hyTERT protein to the proteasome and increases class I presentation of the derived peptides. Downstream the hyTERT sequence, the sequence of the V5 peptide of the flu was inserted to facilitate the detection of the protein.

Figure 1C:
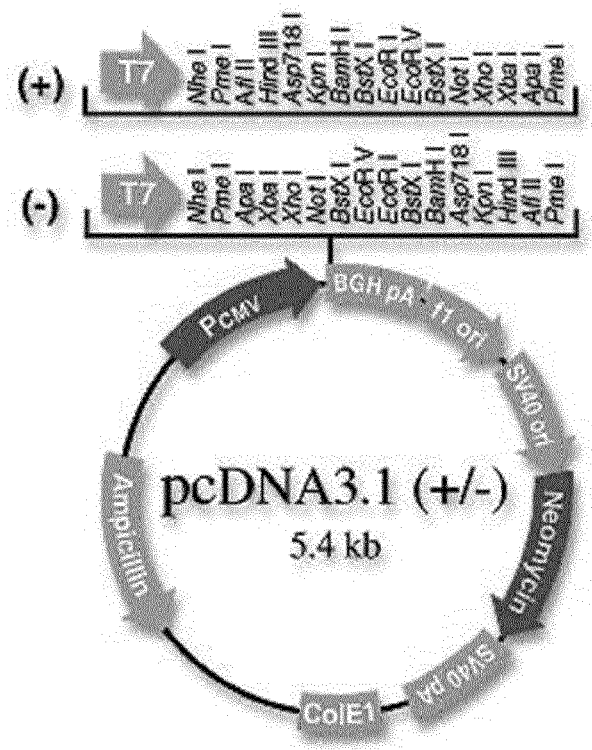
FIG. 1A shows pUF2 nucleotide sequence (SEQ ID NO: 1) and corresponding amino acid sequence comprising cat TERT amino acid sequence. (SEQ ID NO: 2).
FIG. 1B shows pCDT nucleotide sequence (SEQ ID NO: 3) and corresponding amino acid sequence containing cat/dog hybrid TERT amino acid sequence (SEQ ID NO: 4).

Nucleotides 1-6 HindIII restriction site for subcloning
Nucleotides 13-240 ubiquitin
Nucleotides 241-1413 dog TERT (35.9% of TERT sequences)
Nucleotides 1414-3297 cat TERT (54.4% of TERT sequences)
Nucleotides 3298-3456 dog TERT last exon
Nucleotides 3457-3510 influenza A2 epitope
Nucleotides 3511-3552 SV5 V5 tag
Nucleotides 2667-2668 inactivating deletion of 9 bp encoding VDD residues
Nucleotides 3553-3558 two stop codons
Nucleotides 3559-3564 Xba1 restriction site for subcloning FIG. 1C shows a simplified map of pcDNA3.1 expression plasmid into which the cat/dog hybrid TERT nucleic acid sequence was cloned.

Figure 2:
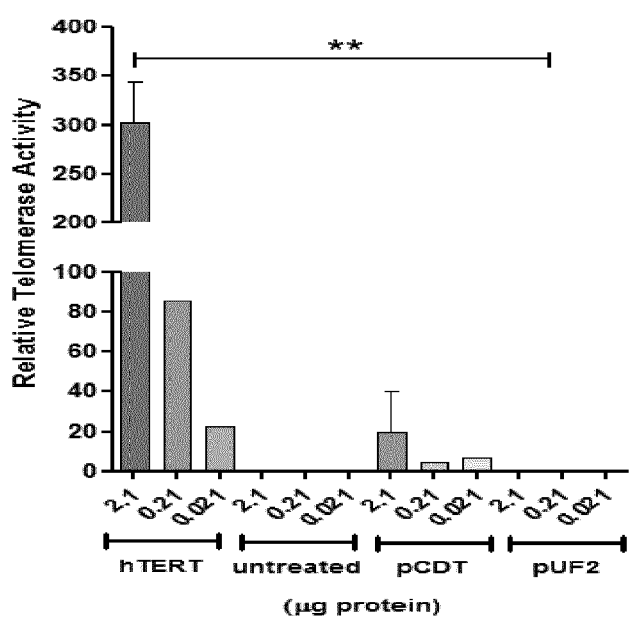

FIG. 2 shows that pDNA constructs are safe (Trapeze), (A) Lysates obtained from CrFK cells transfected with hTERT (human telomerase fully active), pCDT or pUF2 plasmids were analyzed for telomerase activity by the TRAP assay. The level of telomerase activity is shown as relative telomerase activity compared with that of control template measured in each kit. All samples at 2.1 µg protein concentration were measured in triplicate, error bars are standard error of the mean (SEM) (**P=0.0020, hTERT vs pUF2 unpaired t test)

Figure 3:
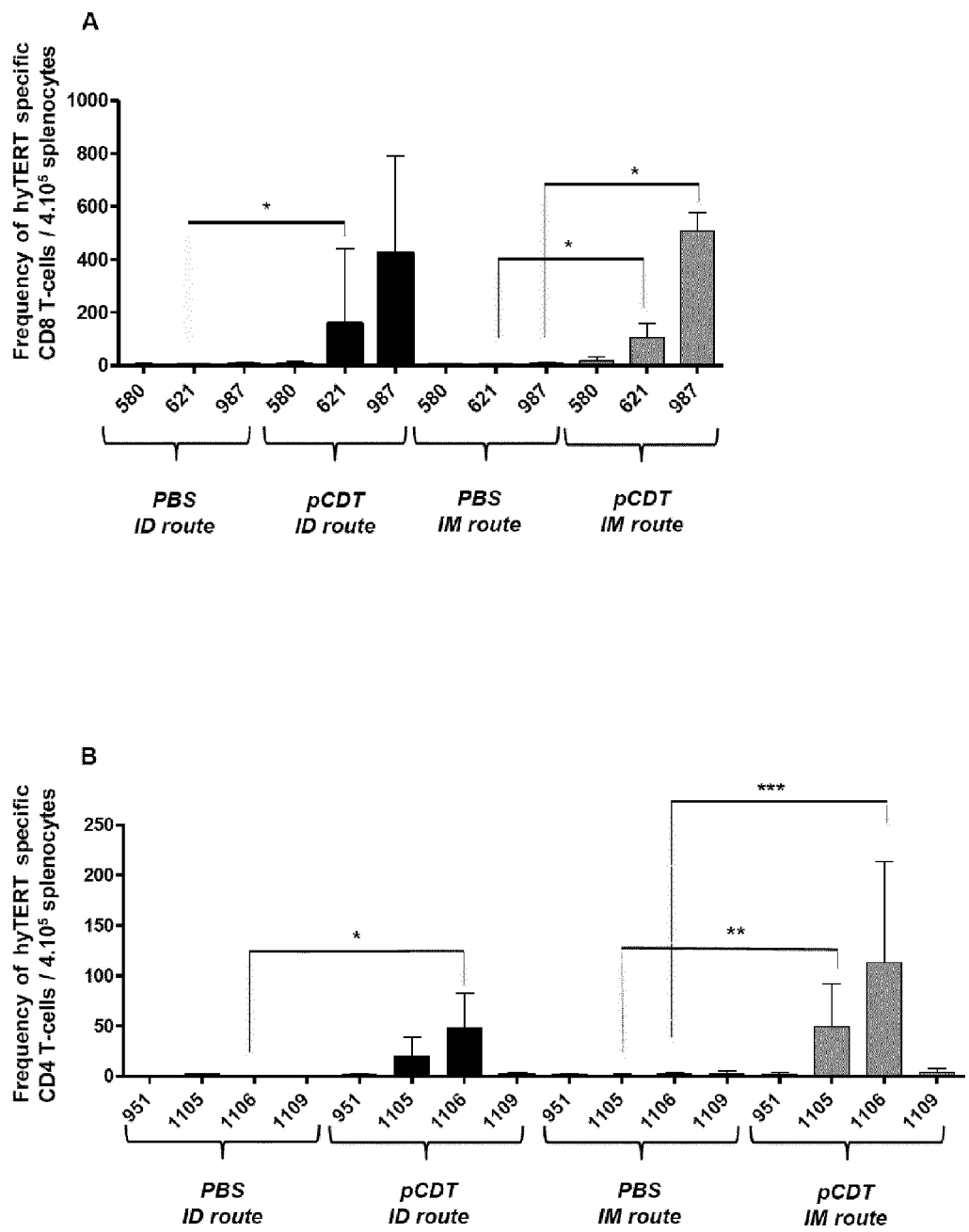

FIGS. 3A and 3B show specific IFNγ+ CD8 and CD4 T-cell responses against H2 restricted hyTERT peptides in mice immunized with pCDT.

Seven week-old female mice were immunized intradermally (ID) or intramuscularly (IM) with either 100 µg pCDT plasmid or PBS at day 0 and boost 14 days later. Ten day post-boost, spleens were harvested. Splenocytes were Ficoll-purified and stimulated in triplicates with 5 µg/mL of relevant peptides for 19 hours. Spots were revealed with a biotin-conjugated detection antibody followed by streptavidin-AP and BCIP/NBT substrate solution.

(A) Plasmid vaccinated groups were composed of five C57/Bl6 mice, and control groups, of three mice. Splenocytes were stimulated with class I peptides p580, p621 and p987. Results show the frequency of peptide specific IFN-γ producing CD8 T cells.

(B) Plasmid vaccinated groups were composed of 9 Balb/cBy mice immunized IM and 5 ID. Control groups of 8 Balb/cBy mice injected IM and 4 ID. Splenocytes were stimulated with class II peptides p951, p1105, p1106 and p1109. Results show the frequency of peptide specific IFN-γ producing CD4 T cells.

Results are the mean±standard deviation. Mann Whitney non parametric test, * p-value <0.05, **: p-value <0.01.

Figure 4:
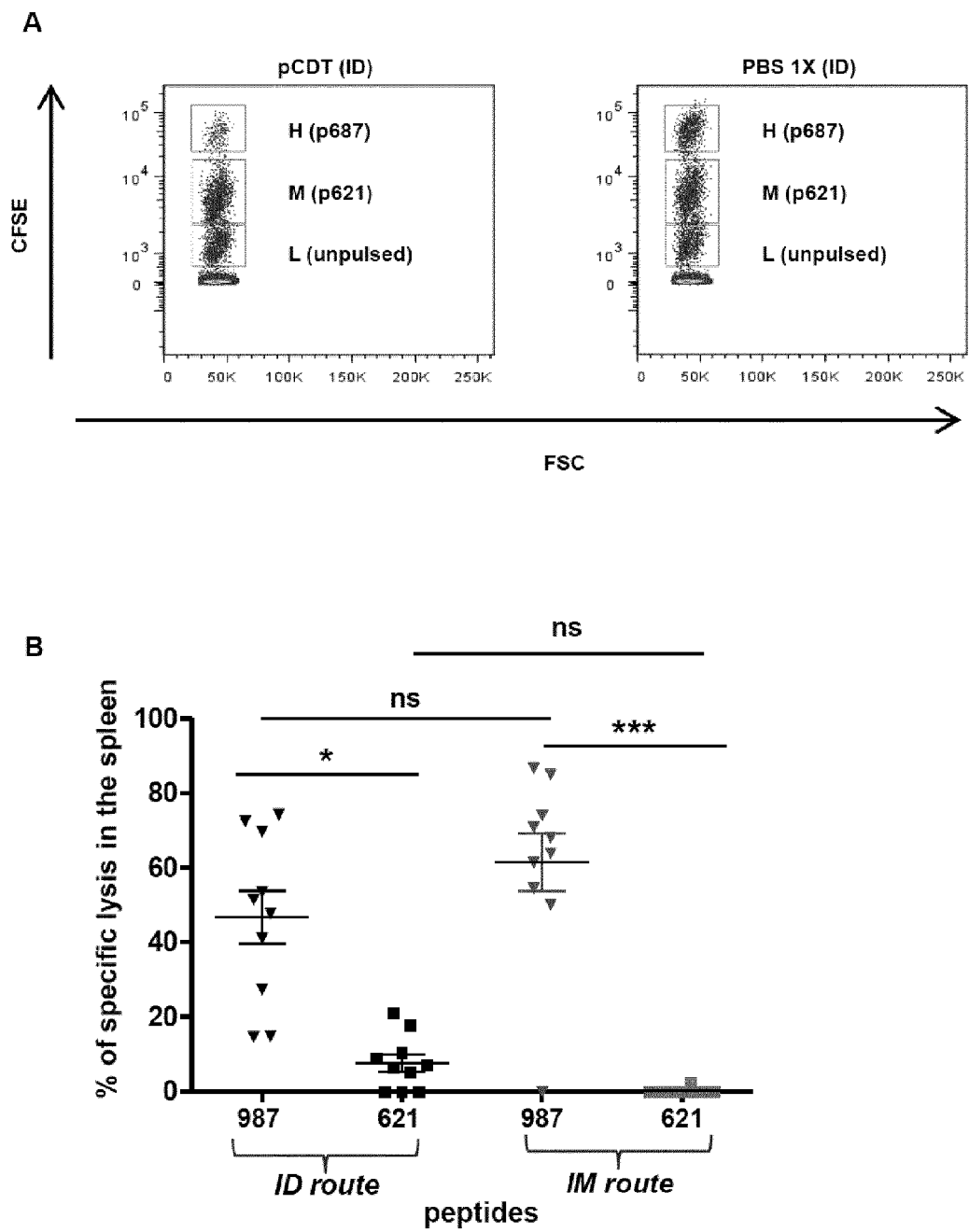

FIGS. 4A and 4B show a hyTERT specific cytotoxic T-lymphocyte (CTL) response in mice immunized with pCDT plasmid, measurable in vivo by elimination of transferred target cells pulsed with H2 restricted hybrid TERT peptides.

7 week-old C57/Bl6 female mice were immunized ID or IM with 100 µg pCDT plasmid at day 0 and day 14 post-priming. At day 9 post-boost injection, syngeneic splenocytes, pulsed with individual dTERT peptides restricted to H2 (either p987 or p621) or left unpulsed were labeled with carboxyfluorescein-diacetate succinimidyl ester (CFSE) at three different concentrations: high=1 µM (987), medium=0.5 µM (621) and low=0.1 µM (unpulsed). The same number of high, medium or low CFSE labeled cells was transferred IV to vaccinated mice. After 15-18 hours, the disappearance of peptide-pulsed cells was determined by fluorescence-activated cell-sorting analysis in the spleen.

The percentage of specific lysis was calculated by comparing the ratio of pulsed to un-pulsed cells in vaccinated versus control mice.

(A) Example of the in vivo CTL assay showing the elimination of target cells pulsed with p621 peptide (High, H) or p987 peptide (Medium, M) in the spleen of a mouse vaccinated ID (left panel) with pCDT. No such disappearing is observed in control mice injected ID with PBS 1× (right panel).

(B) Percentage of specific lysis for each mouse against each individual peptide in the spleen after IM or ID vaccination with pCDT. Horizontal bars show average percentage of lysis per peptide and per immunization route. Standard deviations are also plotted. Representative data from 2 independent experiments (n=10 individual animals/group). Kruskal-Wallis analysis with Dunn's multiple comparison test, * p<0.1, *** p<0.001, ns: not significant. Statistical significance is set at p-value <0.05.

Figure 5:
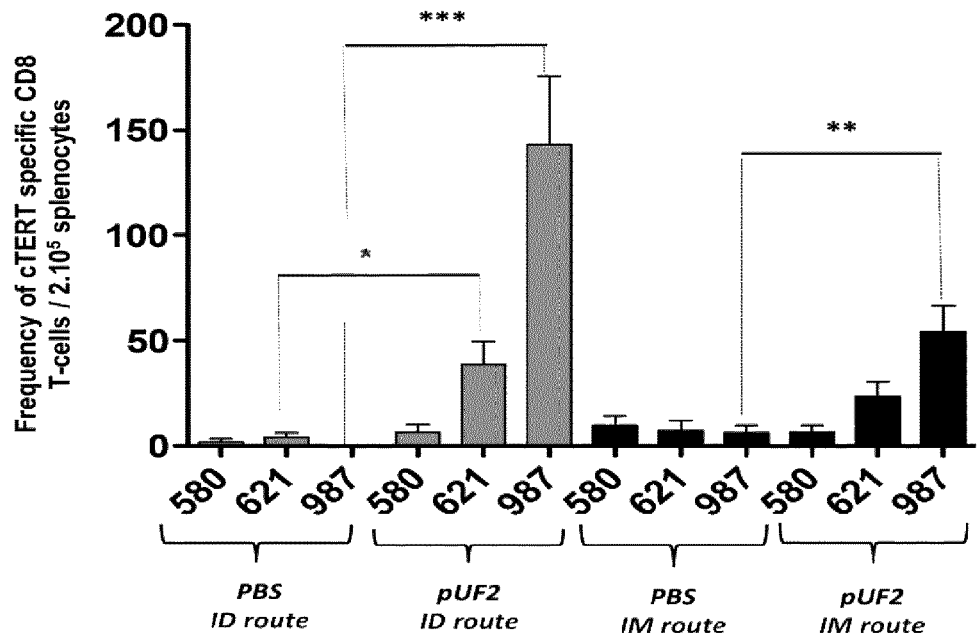
Figure 5:
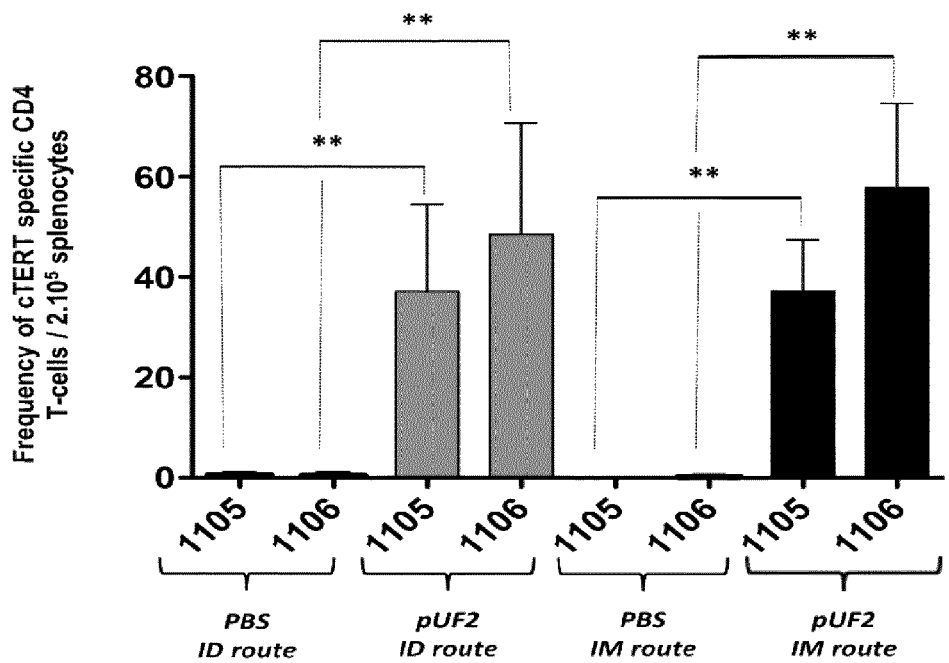

FIGS. 5A and 5B show IFNγ+ specific CD8 and CD4 T-cell responses against H2 restricted cat TERT peptides in mice immunized with pUF2.

Seven week-old female mice were immunized ID or IM with either 100 µg pUF2 plasmid or PBS at day 0 and boost 14 days later. Ten days post boost, spleens were harvested. Splenocytes were Ficoll-purified and stimulated in triplicates with 5 µg/mL of relevant peptides for 19 hours. Spots were revealed with a biotin-conjugated detection antibody followed by streptavidin-AP and BCIP/NBT substrate solution. Vaccinated groups were composed of six C57/Bl6 mice, and control groups, of three mice. Splenocytes were stimulated with class I peptides p580, p621 and p987. Results show the frequency of peptide specific IFN-γ producing CD8 T cells. Vaccinated groups were composed of six Balb/cBy mice, and control groups, of three mice. Splenocytes were stimulated with class II peptides p1105 and p1106. Results show the frequency of peptide specific IFN-γ producing CD4 T cells.

Results are the mean±standard deviation. Mann Whitney non parametric test, * p-value <0.05, **: p-value <0.01.

Figure 6:
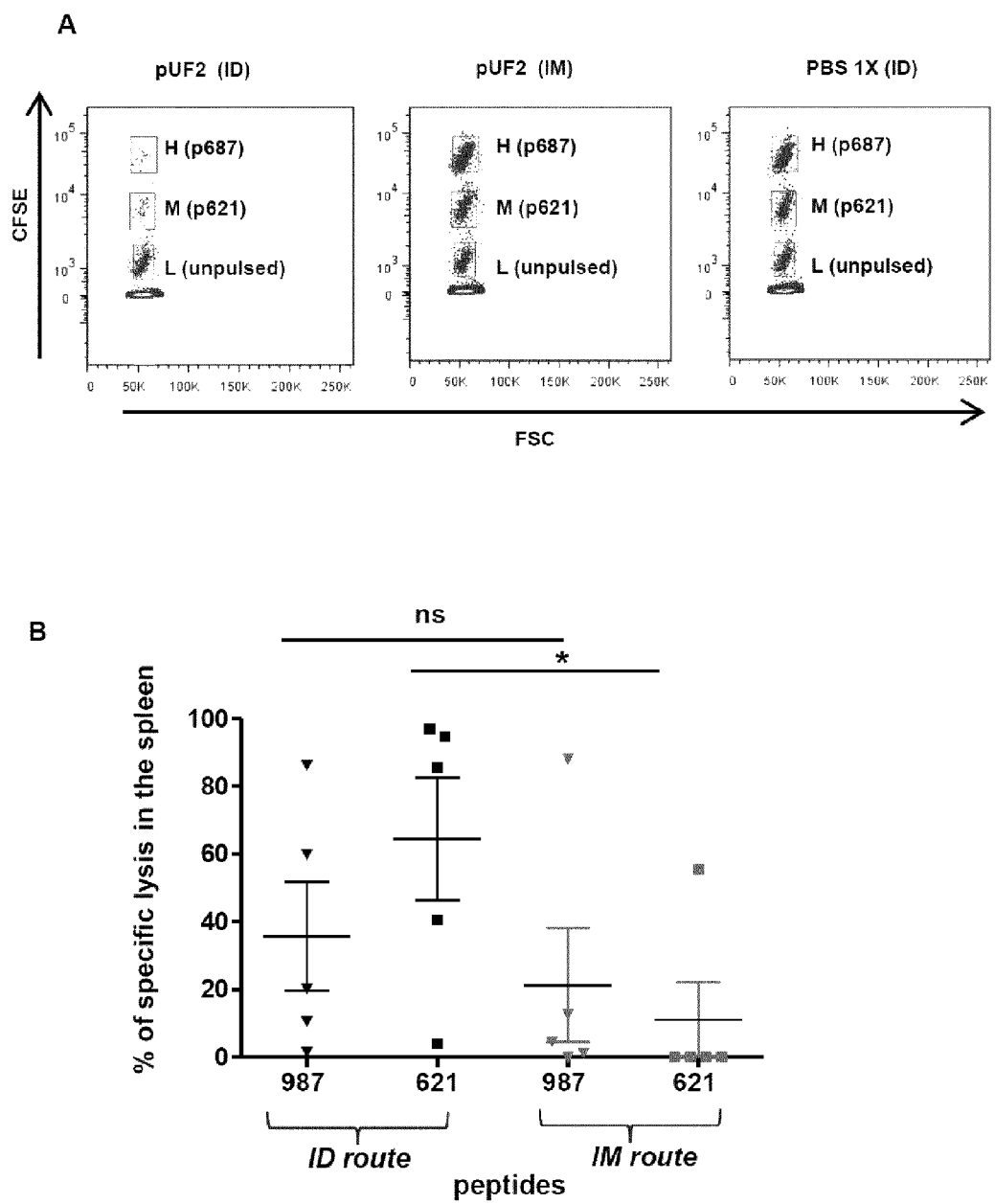

FIGS. 6 A and B show that mice immunized with pUF2 are able to lyse H2 restricted cat TERT peptide-loaded on target cells in vivo 7 week-old C57/Bl6 female mice were immunized ID or IM with 100 µg pCDT plasmid at day 0 and day 14 post-priming. At day 9 post-boost injection, syngeneic splenocytes, pulsed with individual dTERT peptides restricted to H2 (either p987 or p621) or left unpulsed were labeled with carboxyfluorescein-diacetate succinimidyl ester (CFSE) at three different concentrations: high=1 µM (987), medium=0.5 µM (621) and low=0.1 µM (unpulsed). The same number of high, medium or low CFSE labeled cells was transferred IV to vaccinated mice. After 15-18 hours, the disappearance of peptide-pulsed cells was determined by fluorescence-activated cell-sorting analysis in the spleen. The percentage of specific lysis was calculated by comparing the ratio of pulsed to un-pulsed cells in vaccinated versus control mice.

(A) Example of the in vivo CTL assay showing the elimination of target cells pulsed with either p621 or p987 peptides in the spleen of a mouse vaccinated ID (left panel). No such disappearing is observed in control mice (right panel) or in certain mice vaccinated IM (middle panel). H=high, M=Medium, L=Low.

(B) Percentage of specific lysis for each mouse against each individual peptide in the spleen after IM or ID vaccination with pUF2. Horizontal bars show average percentage of lysis per peptide and per immunization route. Standard deviations are also plotted. Representative data from n=5 animals/group. Kruskal-Wallis analysis with Dunn's multiple comparison test, ns: not significant. Statistical significance is set at p-value <0.05.

DETAILED DESCRIPTION OF THE INVENTION

Definitions

The telomerase consists of an RNA template and protein components including a reverse transcriptase, designated "Telomerase Reverse Transcriptase" (TERT), which is the major determinant of telomerase activity. Unless otherwise specified, in the present specification, the term "telomerase" refers to TERT.

In the present invention, the term "cat TERT" refers to the TERT sequence of any domestic cat (also designated as *Felis catus* or *Felis silvestris catus*). Partial molecular cloning of the cat TERT gene (237 bp of mRNA) has been reported by Yazawa et al, 2003. The inventors herein provide a longer sequence of *Felis catus* TERTPartial amino acid sequences of cat TERT are shown as SEQ ID NO:5 and SEQ ID NO:6.

The invention can also make use of non-cat telomerase (TERT) sequence, which can be from any human or non-human mammal, e.g. from dog. The term "dog TERT" refers to the TERT sequence of any domestic dog (also designated *Canis familiaris* or *Canis lupus familiaris*).

A dog TERT mRNA sequence is available with NCBI accession number NM_001031630 (XM_545191). Dog TERT amino acid sequence is shown as SEQ ID NO: 9.

The "telomerase catalytic activity" refers to the activity of TERT as a telomerase reverse transcriptase. The term "deprived of telomerase catalytic activity" means that the nucleic acid sequence encodes a mutant TERT, which is inactive.

The term "hybrid" or "chimeric" amino acid or nucleotide sequence means that part of the sequence originates from one animal species and at least another part of the sequence is xenogeneic, i.e. it originates from at least one other animal species.

When referring to a protein, the term "fragment" preferably refers to fragment of at least 10 amino acids, preferably at least 20 amino acids, still preferably at least 30, 40, 50, 60, 70, 80 amino acid fragments.

In the context of the invention, the term "antigenic fragment" refers to an amino acid sequence comprising one or several epitopes that induce T cell response in the animal, preferably cytotoxic T lymphocytes (CTLs). An epitope is a specific site which binds to a T-cell receptor or specific antibody, and typically comprises about 3 amino acid residues to about 30 amino acid residues, preferably 8 or 9 amino acids as far as class I MHC epitopes are concerned, and preferably 11 to 25 amino acids as far as class II MHC epitopes are concerned.

The term "immunogenic" means that the composition or construct to which it refers is capable of inducing an immune response upon administration (preferably in a cat). "Immune response" in a subject refers to the development of a humoral immune response, a cellular immune response, or a humoral and a cellular immune response to an antigen. A "humoral immune response" refers to one that is mediated by antibodies. A "cellular immune response" is one mediated by T-lymphocytes. It includes the production of cytokines, chemokines and similar molecules produced by activated T-cells, white blood cells, or both. Immune responses can be determined using standard immunoassays and neutralization assays for detection of the humoral immune response, which are known in the art. In the context of the invention, the immune response preferably encompasses stimulation or proliferation of cytotoxic CD8 T cells and/or CD4 T cells.

As used herein, the term "treatment" or "therapy" includes curative treatment. More particularly, curative treatment refers to any of the alleviation, amelioration and/or elimination, reduction and/or stabilization (e.g., failure to progress to more advanced stages) of a symptom, as well as delay in progression of the tumor or dysplasia, or of a symptom thereof.

As used herein, the term "prevention" or "preventing" refers to the alleviation, amelioration and/or elimination, reduction and/or stabilization (e.g., failure to progress to more advanced stages) of a prodrome, i.e. any alteration or early symptom (or set of symptoms) that might indicate the start of a disease before specific symptoms occur. A cell that "overexpresses telomerase" refers to a cell in a subject, which either expresses telomerase, e.g. upon mutation or infection, whereas it does usually not, under normal conditions, or to a cell in a subject which expresses a higher level of telomerase (e.g. upon mutation or infection), when compared to normal conditions. Preferably the cell that overexpresses telomerase shows an increase of expression of at least 5%, at least 10%, at least 20%, 30%, 40%, 50%, 60%, 70%, 80%, or more.

Nucleic Acid Constructs

It is herein provided a nucleic acid that comprises a sequence encoding (i) a cat telomerase reverse transcriptase (TERT) deprived of telomerase catalytic activity, or (ii) a fragment thereof.

The nucleic acid may be DNA or RNA, but is preferably DNA, still preferably double stranded DNA.

As a first safety key, the TERT sequence is deprived of telomerase catalytic activity. In a preferred embodiment, the sequence that encodes cat TERT contains mutations that provide inactivation of the catalytic activity. The term "mutation" include a substitution of one or several amino acids, a deletion of one or several aminoacids, and/or an insertion of one of several amino acids. Preferably the sequence shows a deletion, preferably a deletion of amino acids VDD, as shown in FIG. 1A or 1B.

As a second safety key, the sequence encoding cat TERT can further be deprived of a nucleolar localization signal. This nucleolar localization signal is correlated with the enzymatic activity of TERT. This signal corresponds to the N-terminal 47 amino acids at the N-terminus of the TERT sequence.

Preferably the sequence encoding cat TERT is deleted of N-terminal 47 amino acids. Cat TERT sequence fragments deleted of amino acids VDD and of the N-terminal nucleolar localization signal are shown as SEQ ID NO:7 and SEQ ID NO:8.

In a particular embodiment, the nucleic acid may encode cat TERT sequence or a fragment thereof only, which preferably corresponds to at least 50%, 55%, 60%, 65%, 70%, 75%, 80%, 85%, 90%, or at least 95% of the cat TERT sequence deleted of the N-terminal 47 amino acids.

Preferably, the nucleic acid encodes a cat TERT sequence comprising, or consisting of, SEQ ID NO: 5, 6, 7 or 8.

The nucleic acid may further encode a non-cat TERT antigenic fragment. This embodiment is preferred, to favor breakage of tolerance towards a self-antigen, and induce an efficient immune response along, with an immune memory response in the cat. The presence of non-cat TERT fragment(s) advantageously engages certain subtypes of CD4$^+$ T cells, providing help for anti-tumor immunity, and reversing potential regulation via the secretion of Th1 cytokines.

The cat and non-cat TERT sequences or fragments thereof are preferably fused, to be expressed as a hybrid or chimeric protein. Alternatively, the cat and non-cat TERT sequences or fragments thereof may be separated, but carried on the same vector, e.g. the same plasmid.

Preferably the non-cat TERT antigenic fragment corresponds to a fragment absent or eliminated from the cat TERT sequence, to the extent it does not complement the loss of catalytic activity or the loss of the nucleolar localization signal.

The cat TERT sequence, or fragment thereof, can represent at least 50%, 55%, 60%, 65%, 70%, 75%, 80%, 85%, 90%, or at least 95% of all TERT sequences in the nucleic acid, plasmid, or other vector.

In a preferred embodiment, the cat TERT sequence or fragment represents at least 90% of the hybrid or chimeric TERT protein.

In another embodiment, the cat TERT sequence or fragment represents at least 60% of the hybrid or chimeric TERT protein.

The non-cat TERT antigenic fragment preferably originates from a dog TERT sequence.

The non-cat TERT antigenic fragment is advantageously processed by dendritic cells, thereby generating T cell help.

In a preferred embodiment, the invention employs a nucleic acid that encodes a protein sequence selected from the group consisting of SEQ ID NO: 2, 4, 5, 6, 7, or 8.

Such nucleic acid may comprise a sequence selected from the group consisting of SEQ ID NO: 1, 3, or nucleotides 241-3444, or 382-3444 or 439-3444 of SEQ ID NO:1, or nucleotides 1408-3297 or 1414-3297 or 241-3456 of SEQ ID NO: 3.

In a particular embodiment, the nucleic acid may further encode a protein which enhances the addressing of the TERT protein to the proteasome and increases class I presentation of the derived peptides. Said protein may be preferably ubiquitin or it may be any chaperon protein, e.g. calreticulin.

Genetic Constructs, Immunogenic Compositions and Administration

Preferably, the nucleic acid is a genetic contrast comprising a polynucleotide sequence as defined herein, and regulatory sequences (such as a suitable promoter(s), enhancer(s), terminator(s), etc.) allowing the expression (e.g. transcription and translation) of the protein product in the host cell or host organism.

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises i) at least one nucleic acid of the invention; operably connected to ii) one or more regulatory elements, such as a promoter and optionally a suitable terminator; and optionally also iii) one or more further elements of genetic constructs such as 3'- or 5'-UTR sequences, leader sequences, selection markers, expression markers/reporter genes, and/or elements that may facilitate or increase (the efficiency of) transformation or integration.

In a particular embodiment, the genetic construct can be prepared by digesting the nucleic acid polymer with a restriction endonuclease and cloning into a plasmid containing a promoter such as the SV40 promoter, the cytomegalovirus (CMV) promoter or the Rous sarcoma virus (RSV) promoter. In a preferred embodiment, the TERT nucleic acid sequences are inserted into a pcDNA3.1 expression plasmid (see FIG. 1C) or pcDNA3.1 TOPO-V5. Other vectors include retroviral vectors, lentivirus vectors, adenovirus vectors, vaccinia virus vectors, pox virus vectors and adenovirus-associated vectors.

Compositions can be prepared, comprising said nucleic acid or vector. The compositions are immunogenic. They can comprise a carrier or excipients that are suitable for administration in cats (i.e. non-toxic, and, if necessary, sterile). Such excipients include liquid, semisolid, or solid diluents that serve as pharmaceutical vehicles, isotonic agents, stabilizers, or any adjuvant. Diluents can include water, saline, dextrose, ethanol, glycerol, and the like. Isotonic agents can include sodium chloride, dextrose, mannitol, sorbitol, and lactose, among others. Stabilizers include albumin, among others. Any adjuvant known in the art may be used in the vaccine composition, including oil-based adjuvants such as Freund's Complete Adjuvant and Freund's Incomplete Adjuvant, mycolate-based adjuvants, bacterial lipopolysaccharide (LPS), peptidoglycans, proteoglycans, aluminum hydroxide, saponin, DEAE-dextran, neutral oils (such as miglyol), vegetable oils (such as *arachis* oil), Pluronic® polyols.

The nucleic acid or composition can be administered directly or they can be packaged in liposomes or coated onto colloidal gold particles prior to administration. Techniques for packaging DNA vaccines into liposomes are known in the art, for example from Murray, 1991. Similarly, techniques for coating naked DNA onto gold particles are taught in Yang, 1992, and techniques for expression of proteins using viral vectors are found in Adolph, 1996.

For genetic immunization, the vaccine compositions are preferably administered intradermally, subcutaneously or intramuscularly by injection or by gas driven particle bombardment, and are delivered in an amount effective to stimulate an immune response in the host organism. In a preferred embodiment of the present invention, administration comprises an electroporation step, also designated herein by the term "electrotransfer", in addition to the injection step (as described in Mir 2008, Sardesai and Weiner 2011).

The compositions may also be administered ex vivo to blood or bone marrow-derived cells using liposomal transfection, particle bombardment or viral transduction (including co-cultivation techniques). The treated cells are then reintroduced back into the subject to be immunized.

While it will be understood that the amount of material needed will depend on the immunogenicity of each individual construct and cannot be predicted a priori, the process of determining the appropriate dosage for any given construct is straightforward. Specifically, a series of dosages of increasing size, starting at about 5 to 30 µg, or preferably 20-25 µg, up to about 500 µg for instance, is administered to the corresponding species and the resulting immune response is observed, for example by detecting the cellular immune response by an Elispot assay (as described in the experimental section), by detecting CTL response using a chromium release assay or detecting TH (helper T cell) response using a cytokine release assay.

In a preferred embodiment, the vaccination regimen comprises one to three injections, preferably repeated three or four weeks later.

In a particular embodiment, the vaccination schedule can be composed of one or two injections followed three or four weeks later by at least one cycle of three to five injections.

In another embodiment, a primer dose consists of one to three injections, followed by at least a booster dose every year, or every two or years for instance.

Prevention or Treatment of Tumors

The nucleic acid or immunogenic composition as described above is useful in a method for preventing or treating a tumor in a cat.

A method for preventing or treating a tumor in a cat is described, which method comprises administering an effective amount of said nucleic acid or immunogenic composition in a cat in need thereof. Said nucleic acid or immunogenic composition is administered in an amount sufficient to induce an immune response in the cat.

The tumor may be any undesired proliferation of cells, in particular a benign tumor or a malignant tumor, especially a cancer.

The cancer may be at any stage of development, including the metastatic stage. However preferably the cancer has not progressed to metastasis.

In particular the tumor may be selected from the group consisting of a lymphoma or lymphosarcoma (LSA), adenoma, lipoma, myeloproliferative tumor, melanoma, squamous cell carcinoma, mast cell tumor, osteosarcoma, fibrosarcoma, lung tumor, brain tumor, nasal tumor, liver tumor, and mammary tumor.

Lymphoma or lymphosarcoma (LSA) is common among cats with Feline Leukemia Virus (FeLV) infections. LSA affects the intestines and other lymphatic tissues (commonly the abdominal organs).

Adenomas are tumors that affect sebaceous glands predominantly in the limbs, the eyelids and the head. They are also commonly-found in the ears (and ear canals) of cats and may lead to the development of hyperthyroidism.

Lipomas are tumors that occur within the fatty tissues and reside as soft, fluctuant round masses that adhere tightly to surrounding tissue (typically to organs and the membrane linings of body cavities).

Myeloproliferative tumors generally are genetic disorders. It can affect the bone marrow, white blood cells, red blood cells, and platelets.

Melanomas manifest as basal cell tumors. These tumors are usually benign in nature. They are commonly found around the neck, head, ears, and shoulder regions and can be treated through chemotherapy or radiation therapy.

Squamous cell carcinomas affect areas that lack natural pigmentation (oral cavity, tonsils, lips, nose, eyelids, external ear, limbs, toes and nails), or areas that are under constant trauma and irritation. Oral squamous carcinomas are the most common.

Mast cell tumors are either sole or multiple skin nodules that may be ulcerated and pigmented. They can be located on any part of the cat's body.

Osteosarcoma are tumors that mainly affect the joints, bones and lungs.

Fibrosarcomas arise from the fibrous tissues just beneath the skin. Fibrosarcomas generally develop in muscle or in the connective tissue of the body.

Generally speaking, lung tumors, brain tumors, nasal tumors, liver tumors, mammary tumors are encompassed.

In a particular embodiment, the vaccination according to the invention may be combined with conventional therapy, including chemotherapy, radiotherapy or surgery. Combinations with adjuvant immunomodulating molecules such as GM-CSF or IL-2 could also be useful.

The Figures and Examples illustrate the invention without limiting its scope.

EXAMPLES

The inventors have constructed DNA vaccines encoding an inactivated form of cat TERT and a cat/dog hybrid TERT (Example 1), and have assessed their functionality, safety and immunogenicity.

They have demonstrated that the plasmids were correctly processed in vitro after transfection in mammalian cells and that the plasmid product of expression (TERT protein) was well expressed. Moreover, no enzymatic activity was detected and TERT proteins were found excluded for the transfected cells nucleoli, which evidences safety of the constructs (Example 2).

Then, the plasmids were found to be immunogenic and to elicit specific efficient CD8 T cells and CD4 T cells in mice (Example 3).

Example 1: Construction of the DNA Plasmids

In all constructs, the TERT sequence is preceded by a DNA sequence encoding the human-ubiquitin. The presence of the Ubiquitin will increase the addressing of the TERT protein to the proteasome and increase the class I presentation pathway of TERT derived peptides. TERT sequence is followed by the sequence of the influenza protein V5 to facilitate future purification or detection of the fusion protein by Western Blot or histochemistry for example.

The DNA sequence coding for the TERT protein has been deleted of 47 Amino-acids in the N-Term region, which encodes the nucleolar importation signal. Moreover, three amino-acids have been removed in the catalytic site of TERT (VDD), to inhibit the protein enzymatic activity. pUF2 encodes 95% of the cat TERT and 5% of the canine TERT sequence (FIG. 1A), pCDT encodes 54.4% of the cat TERT sequence and 35.9% of the dog TERT sequence (FIG. 1B).

All TERT DNA sequences were synthetized from Genecust (Dudelange, Luxembourg). Then they were cloned into the pCDNA3.1 or pcDNA3.1 TOPO-V5 expression plasmid provided by Life technologies SAS (Saint-Aubin, France) using the HindIII and XbaI restriction sites (see FIG. 1C). Plasmids were stored at −20° C., in PBS 1×, at a concentration of 2 mg/mL prior use. The backbone plasmid was used as empty vector for western blot and Trap-Assay experiments. It consists of the pcDNA3.1 backbone plasmid deprived of the transgene protein DNA sequence (TERT).

Example 2: Functionality and Safety of the Plasmids 2.1. Materials and Methods
Cell Culture The 293T cell line used for transfection assays and immune-fluorescence experiments were kindly provided by Pr Simon Wain-Hobson (Pasteur Institute). CrFK cells were kindly provided by Pr J. Richardson (Ecole Vétérinaire de Maison-Alfort). Cells were grown at 37° C., 5% $CO_2$ in Dulbecco's Modified Eagle Medium (DMEM) supplemented with 10% heat-inactivated Fetal Calf Serum (FCS), 1% sodium-pyruvate, 1% penicillin-streptomycin pyruvate and 0, 1% β-mercaptoethanol. All components of the culture medium were purchased from Life technologies SAS (Saint-Aubin, France).

Transfection Assays

Transfection of 293T cells were performed with either pCDT or pUF2 plasmids using the JetPRIME® transfection kit (Polyplus-transfection SA, Illkirch, France) according to manufacturer's instruction. In a 6-well plate, 400 000 HeLa cells or 293T cells per well were seeded in 2 mL of DMEM culture medium, and cultured 24 hours at 37° C., 5% $CO_2$ prior transfection. For each well, 2 μg of each plasmid diluted in 200 μL of jetPRIME® buffer, or 200 μL of jetPRIME® buffer only with respectively 4 μL of jetPRIME® agent were drop onto the cells. Transfection medium were removed 4 hours later and replaced by 2 mL of DMEM culture medium. Cells were put at 37° C., 5% CO2 and recovered for analysis 24 hours later.

Western Blots

Transfected 293 T cells were lysed on ice with radioimmunoprecipitation assay (RIPA) lysis buffer (RIPA Buffer, Sigma Aldrich chimie SARL, Saint-Quentin Fallavier, France) containing protease inhibitors cocktail (Complete EDTA-free, Roche Diagnostic, Indianapolis, USA) for 10-20 minutes. Then, suspension was centrifuged 15 minutes at 14000 rpm at 4° C. in order to remove cellular debris. The supernatants were harvested and the protein concentration was measured using the Bradford method. Protein samples were denatured 5 minutes at 95° C., separated on Nu-PAGE® Novex 4-12% Bis-Tris gels (Invitrogen, Carlsbad, USA) and transferred to PVDF membranes (iBlot® transfer stack, Invitrogen, Carlsbad, USA) using the iBlot® device (Invitrogen, Carlsbad, USA). The membrane was cut approximately at 60 kDa. First, the upper part membrane was probed with an anti-V5 antibody (Invitrogen, Carlsbad, USA) while the other part was probed with an anti-β-actin antibody (Sigma Aldrich chimie SARL, Saint-Quentin Fallavier, France), then samples were revealed by an ECL (Enhanced chemiluminescence) anti-mouse Horse Radish Peroxidase (HRP) linked antibody (GE Healthcare, Vélizy, France)). Immunoblot signals were reveled using 18×24 films and the corresponding cassette both products purchased from GE healthcare (Buckinghamshire, UK).

Immunofluorescence and Microscopy 293T cells were seeded on 8-well Lab-Tek® chamber slides (Sigma Aldrich chimie SARL, Saint-Quentin Fallavier, France) at $20·10^3$ cells/well in 200 μL of culture medium and incubated overnight at 37° C. The next day, culture medium was discarded. Ten μL of a mix solution containing 1 μg of either pCDT or pUF2 plasmid, 50 μL of OptiMEM (Life technologies SAS, Saint-Aubin, France) and 2.5 μL of Fugene HD (Promega France, Charbonnières-les-bains, France) were added to the corresponding chamber. As control, $20·10^3$ HeLa cells were incubated with the 10 μL of the same mix without plasmid. Chamber slides were left in the incubator for 24 hours. Transfected 293T cells were carefully washed with PBS 1× and 200 μL 2% PFA were added to each well for 10 minutes at +4° C., in order to fix and permeabilize the cells. Then wells were washed two times with PBS 1×0.05% Tween®20 and 293T cells were incubated 30 minutes at room temperature with 200 μL of Blocking solution (0.5% TritonX100; 3% BSA; 10% Goat Serum). Eventually, wells were incubated for 1.5 hours at room temperature with a primary mouse anti-V5 antibody (Life technologies SAS, Saint-Aubin, France) diluted in blocking solution at 1/200, with slight agitation. After three washes in PBS 1×0.05% Tween®20, a secondary goat anti-mouse-Alexa Fluor 488® antibody (Life technologies SAS, Saint-Aubin, France) diluted in blocking solution (1/500) was put in the wells for 45 minutes at room temperature away from light and under slight agitation. Wells were washed three times with PBS 1×0.05% Tween®20 and mounted with the Vectashield® mounting medium containing DAPI (Vector laboratories, Peterborough, UK). Slides were analyzed with a fluorescence microscope (Axio observer Z1, Carl Zeis MicroImaging GmbH, Jena, Germany) equipped with an image processing and analysis system (Axiovision, Carl Zeis MicroImaging GmbH, Jena, Germany).

Trap-Assay

Telomerase activity was measured by the photometric enzyme immunoassay for quantitative determination of telomerase activity, utilizing telomeric repeat amplification protocol (TRAP) (Yang et al. 2002).

CrFK (Crandell Rees Feline Kidney) telomerase-negative cells (Yazawa et al., 2003) were transfected with plasmids encoding pUF2 or pCDT TERT constructs. Briefly, 24 hours after transfection, CrFK cells were harvested by mechanical scraping and then washed twice with 1 mL PBS and pelleted by centrifugation 5 minutes at 3000 g, at 4° C. Telomerase activity was assessed by TRAP-ELISA assay using the TeloTAGGG Telomerase PCR ELISAPLUS kit (Roche Diagnostics, Germany) according to the manufacturer's instructions. The protein concentration in the cell extract was measured by the Bradford method (Bio-Rad Laboratories). Three microliters of the cell extract (equivalent to 2.1, 0.21, 0.021 µg) was incubated in a Polymerase Chain reaction (PCR) mixture provided in the kit. The cycling program was performed with 30 minutes primer elongation at 25° C. and then the mixture was subjected to 30 cycles of PCR consisting of denaturation at 94° C. for 30 sec, annealing at 50° C. for 30 sec, polymerization at 72° C. for 90 sec and final extension at 72° C. for 10 minutes. 2.5 µl of amplification product was used for ELISA according to the manufacturer's instructions. The absorbance at 450 nm (with a reference of 690 nm) of each well was measured using Dynex MRX Revelation and Revelation TC 96 Well Microplate Reader.

Telomerase activity was calculated as suggested in the kit's manual and compared with a control template of 0.1 amol telomeric repeats, representing a relative telomerase activity (RTA) of 100. Inactivated samples and lysis buffer served as negative controls.

2.2. Results

New TERT Encoding Plasmids are Functional In Vitro after Transfection

The functionality of the new plasmid constructs is shown by the presence of the plasmid encoded TERT protein in the total protein lysate of pCDT or pUF2 transfected cells in vitro. The inventors performed western-blot assays on the total protein lysate of 293T cells plasmids transfected with pCDT or pUF2 (24 h after transfection). As the TERT protein sequence encoded by each plasmid was tagged with the V5 protein sequence, anti-V5 antibody coupled with Horse Radish Peroxidase (HRP) was used to reveal the presence of the fusion protein of interest.

A highly positive V5 specific-signal was detected 24 h after transfection in the protein lysate of pCDT or pUF2 transfected cells. The size of the protein band detected corresponds to the different TERT protein encoded by the plasmids which molecular weight is 123 kDa. Moreover no V5 specific signal was detected in untreated or empty plasmid transfected cells. The inventors demonstrated that pUF2 and pCDT plasmids were correctly processed in vitro after transfection in mammalian cells and that the plasmid product of expression (TERT protein) was well expressed.

New TERT Encoding Plasmids Express a Non-Functional Enzyme of which Cellular Expression is Excluded from the Nucleoli after In Vitro Transfection To test the absence of enzymatic activity, a TRAPeze assay was performed. As illustrated by FIG. 2, protein lysates from pUF2 or pCDT transfected cells do not exhibit any telomerase activity. As a positive control, the protein extracts from 293T cells transfected with the native human TERT were used. Thus the inventors demonstrated that the TERT proteins encoded by either pCDT or pUF2 plasmids do not express any functional enzymatic activity after in vitro transfection.

The inventors have further investigated the intracellular location of the two plasmid products of expression. To this aim, an in vitro immunofluorescence assay was performed. Briefly, 24 h after in-vitro transfection of 293T cells with either pCDT or pUF2, an anti-V5 antibody coupled to an Alexa-Fluor labeled secondary antibody were used to detect the TERT proteins within the cells. The pCDT and pUF2 encoded TERTs were not detected inside the cell nucleoli contrary to what was observed with 293T cells transfected with the plasmid encoding the native human TERT.

To conclude, the inventors demonstrated that after in vitro transfection with either pUF2 and pCDT plasmids, first the TERT protein expression is excluded from the nucleoli and secondly, these products of expression do not exhibit any enzymatic activity. These two criteria establish the safety of the plasmids and favour their use for in vivo vaccination.

Example 3: In Vivo Immune Response 3.1. Materials and Methods

Mice

Female Balb/cBy and C57BL/6J mice (6-8 week old) were purchased from Janvier laboratories (Saint-Berthevin, France). Animals were housed at the Specific Pathogen Free animal facility of the Pasteur Institute. Mice were anesthetized prior to intradermal (ID) or intramuscular (IM) immunizations, with a mix solution of xylazine 2% (Rompun, Bayer Santé, Loos, France) and Ketamine 8% (Imalgen 1000, Merial, Lyon, France) in Phosphate Buffer Saline 1× (PBS 1×, Life technologies SAS, Saint-Aubin, France), according to individual animal weight and duration of anesthesia (intraperitoneal route). All animals were handled in strict accordance with good animal practice and complied with local animal experimentation and ethics committee guidelines of the Pasteur Institute of Paris.

H2 Restricted Peptides

TERT peptides used in mouse studies (IFNγ ELIspot) were predicted by in-silico epitope prediction in order to bind mouse class I MHC, H2K$^b$, H2D$^b$ or mouse class II H2-IA$^d$ using four algorithms available online:

Syfpeithi (http://www.syfpeithi.de/), Bimas (http://www-bimas.cit.nih.gov/), NetMHCpan and SMM (http://tools.immuneepitope.org/main/).

All synthetic peptides were purchased lyophilized (>90% purity) from Proimmune (Oxford, United Kingdom). Lyophilized peptides were dissolved in sterile water at 2 mg/mL and stored in 35 µL aliquots at −20° C. prior use. Details of peptides sequence and H2 restriction is shown in table 1.

TABLE 1

H2 restricted peptides sequences determined
by in silico prediction algorithms

H2D$^b$ restricted TERT peptides

| | | | |
|---|---|---|---|
| 621-629 | (RPIVNMDYI) | 621 | SEQ ID NO: 10 |
| 580-589 | (RQLFNSVHL) | 580 | SEQ ID NO: 11 |
| 987-996 | (TVYMNVYKI) | 987 | SEQ ID NO: 12 |

H2-IA$^d$ restricted TERT peptides

| | | | |
|---|---|---|---|
| 1106-1121 | (CLLGPLRAAKAHLSR) | 1106 | SEQ ID NO: 13 |
| 1105-1120 | (RCLLGPLRAAKAHLS) | 1105 | SEQ ID NO: 14 |
| 951-966 | (YSSYAQTSIRSSLTF) | 951 | SEQ ID NO: 15 |
| 1109-1124 | (GPLRAAKAHLSRQLP) | 1109 | SEQ ID NO: 16 |

Mice Immunization and In Vivo Electroporation

Intradermal (ID) immunization was performed on the lower part of the flank with Insulin specific needles (U-100, 29G×½"-0.33×12 mm, Terumo, Belgium) after shaving. No erythema was observed after shaving, during and after immunization procedure. Intramuscular immunization (IM) was performed in the anterior tibialis cranialis muscle, also using Insulin specific needles U-100. Each animal received a priming dose of either pCDT or pUF2, independently of vaccine route, corresponding to 100 µg of DNA. All animals were boosted at day 14 post-prime using the same amount of plasmid and the same route of immunization. Directly after ID vaccination, invasive needle electrodes (6×4×2, 47-0050, BTX, USA) are inserted into the skin so that the injection site is placed between the two needle rows (the two needle rows are 0.4 cm apart). Two pulses of different voltages were applied (HV-LV): HV=1125V/cm (2 pulses, 50 µs-0.2 µs pulse interval) and LV=250V/cm (8 pulses, 100V-10 ms-20 ms pulse interval). Immediately after IM immunization the muscle injection site was covered with ultrasonic gel (Labo FH, blue contact gel, NM Medical, France) and surrounded by tweezers electrodes (0.5 cm apart, tweezertrode 7 mm, BTXI45-0488, USA) and voltage was applied using the same parameters than for skin electroporation. The Agilepulse® in vivo system electroporator was used for all experiments (BTX, USA).

For each route of immunization (IM, ID) control mice were treated with the same procedures using the same volume of PBS 1×.

Elispot Assay

Briefly, PVDF microplates (IFN-γ Elispot kit, Diaclone, Abcyss, France, 10×96 tests, ref. 862.031.010P) were coated overnight with capture antibody (anti-mouse IFN-γ) and blocked with PBS 2% milk. Spleens from pDNA-immunized mice were mashed and cell suspensions were filtered through a 70-mm nylon mesh (Cell Strainer, BD Biosciences, France). Ficoll-purified splenocytes (Lymphocyte Separation Medium, Eurobio, France) were numerated using the Cellometer® Auto T4 Plus counter (Ozyme, France) and added to the plates in triplicates at 2×10$^5$ or 4×10$^5$ cells/well and stimulated with 5 µg/ml of cTERT or hyTERT relevant peptides or Concanavalin A (10 µg/ml), or mock stimulated with serum free culture medium. After 19 hours, spots were revealed with the biotin-conjugated detection antibody followed by streptavidin-AP and BCIP/NBT substrate solution. Spots were counted using the Immunospot ELIspot counter and software (CTL, Germany).

In Vivo Cytotoxicity Assay

Briefly, for target cell preparation, splenocytes from naïve C57/Bl6 mice were labeled in PBS 1× containing high (5 µM), medium (1 µM) or low (0.2 µM) concentrations of CFSE (Vybrant CFDA-SE cell-tracer kit; Life technologies SAS, Saint-Aubin, France). Splenocytes labeled with 5 and 1 µM CFSE were pulsed with 2 different H2 peptides at 5 µg/ml for 1 hour and 30 minutes at room temperature. Peptides 987 and 621 were used for pulsing respectively CFSE high and medium labeled naïve splenocytes. CFSE low labeled splenocytes were left unpulsed. Each mouse previously immunized with either pCDT or pUF2 received at day 10 post-boost injection 10$^7$ CFSE-labeled cells of a mix containing an equal number of cells from each fraction, through the retro-orbital vein. After 15-18 hours, single-cell suspensions from spleens were analyzed by flow cytometry MACSQUANT® cytometer (Miltenyii, Germany).

The disappearance of peptide-pulsed cells was determined by comparing the ratio of pulsed (high/medium CFSE fluorescence intensity) to unpulsed (low CFSE fluorescence intensity) populations in pDNA immunized mice versus control (PBS 1× injected) mice. The percentage of specific killing per test animal was established according to the following calculation:

$$[1-[\text{mean}(CFSE^{low}PBS/CFSE^{high/medium}PBS)/(CFSE^{low}pDNA/CFSE^{high/medium}pDNA)]]\times 100.$$

Statistical Analysis and Data Handling

Prism-5 software was used for data handling, analysis and graphic representations. Data are represented as the mean±standard deviation. For statistical analyses of ELIspot assays we used a Mann Whitney non parametric test, and a Kruskal-Wallis analysis with Dunn's multiple comparison test for in vivo cytotoxicity assay. Significance was set at p-value <0.05.

3.2. Results pCDT Induces a Strong Cytotoxic CD8 T Cell Response Along with a Specific CD4 T Cell Response after ID or IM Immunization and Electroporation in Mice In light of the importance of cytotoxic CD8 T cells in antitumor immune responses, the inventors have assessed whether plasmid pCDT was able to promote such an immune response in vivo. Thus, different groups of 9-10 C57-Bl/6 mice were immunized with pCDT by ID or IM injection of the plasmid immediately followed by electroporation. Two weeks later, mice received a boost injection with the same protocol. On day 10 post-boost, mice spleens were harvested and the induced immune response was monitored via an IFN-γ ELISPOT assay using H2 restricted peptides described in Table 1.

Hy-TERT peptides restricted to mouse MHC class I were predicted in silico as described in the material and methods section. As shown in FIG. 3A, a significant augmentation in the frequency of hyTERT specific IFN-γ secreting CD8 T-cells was observed in the spleen of ID and IM vaccinated animals in comparison with control mice. This was observed for 2 out of 3 class I restricted peptides (p621 and p987, p<0.05). No significant difference in the frequency of specific CD8 T cells was observed between IM and ID route for both peptides p921 and p987.

The inventors have further investigated the hyTERT restricted CD4 T cell response. To this aim, 9-10 Balb-C mice were immunized with pCDT by ID or IM injection immediately followed by electroporation and the CD4 specific T cell response was monitored in the spleen as described before using hyTERT IA$^d$ restricted peptides (in silico prediction). Balb-C mice were chosen because this mouse strain is known to develop good CD4 T cell responses. As shown in FIG. 3B, when performing the IFN-γ ELISPOT assay, a significant augmentation in the frequency of hyTERT specific IFN-γ secreting CD4 T-cells was observed in the spleen of ID and IM vaccinated Balb/C mice in comparison with control mice injected with PBS 1×. This was observed for 2 out of 3 class I restricted peptides (p1106 and p1105, with respectively for p1106 p<0.05 for ID route and p<0.001 for IM route and for 1105 the difference was not significant for ID route and p<0.01 for IM route). No significant difference in the frequency of specific CD4 T cells was observed between IM and ID route for both peptides p1105 and p1106.

Thus, pCDT construct is able to promote the expansion of hyTERT specific CD8 and CD4 T-cells in mice. The inventors next wanted to show that hyTERT specific CD8 T-cells exhibit a functional cytotoxic activity in vivo, which will be necessary to destroy tumor cells. In order to measure the in vivo cytolytic strength of the CD8$^+$ T-cell response elicited by pCDT immunization, the inventors performed an in vivo cytotoxicity test using carboxyfluorescein-diacetate succinimidyl ester (CFSE)-labelled, peptide-pulsed splenocytes as target cells. 7 week old C57/Bl6 mice which received a prime and boost vaccination with pCDT via the ID or IM route as described before or mock-immunized with phosphate-buffered saline (PBS) were intravenously injected with $10^7$ target cells. Target cells were splenocytes from naïve congenic mice separately labelled with three different concentrations of CFSE and pulsed with individual peptides (p621 or p987) or left un-pulsed as an internal control. After 15-18 hours, spleen cells were obtained and the disappearance of peptide-pulsed cells in control versus immunized mice was quantified by fluorescence-activated cell sorting.

Results show that mice develop CTLs against the 2 peptides p621 and p987 which were predicted in silico. Peptide 987 gives the strongest in vivo lysis. Results were consistent with the ones from the IFN-γ Elispot assays (FIG. 3A). It is worth mentioning that for p621, the mean percent lysis was slightly superior when pCDT was injected via the ID route (mean ID=7.7% vs mean IM=0.2%), however, no significant difference was observed between the two routes of immunization.

pUF2 Induces a Strong Cytotoxic CD8 T Cell Response Along with a Specific CD4 T Cell Response after ID or IM Immunization and EP in Mice The inventors have further investigated whether the pUF2 plasmid was able to stimulate the cTERT specific CD8 T cell response in mice. To this aim, different groups of 5 C57-Bl/6 mice were immunized with pUF2 by ID or IM injection immediately followed by electroporation. Two weeks later, mice received a boost injection with the same protocol. On day 10 post-boost, mice spleens were harvested and the induced immune response was monitored via an IFN-γ ELISPOT assay using H2 restricted peptides described in Table 1. cTERT peptides restricted to mouse MHC class I were predicted in silico as described in the material and methods section above. As shown in FIG. 5A, a significant increase in the frequency of cTERT specific IFN-γ secreting CD8 T-cells was observed in the spleen of ID and IM vaccinated animals in comparison with control mice. This was observed for 2 out of 3 class I restricted peptides (p621 and p987, with respectively for p621 p<0.05 for ID route and no significant difference for IM route and for p687, p<0.001 for ID route and p<0.01 for IM route). No significant difference in the frequency of specific CD8 T cells was observed between IM and ID route for both peptides p921 and p987. However, the mean frequency of p987 specific CD8 T cells was slightly higher when mice were injected via the ID route, in comparison with the IM route (mean ID=143.2 vs mean IM=54.2). The inventors have further investigated the cTERT restricted CD4 T cell response. To this aim, 9-10 Balb-C mice were immunized ID or IM with pUF2 immediately followed by electroporation and the CD4 specific T cell response was monitored in the spleen as described before using cTERT IA$^d$ restricted peptides (in silico prediction). Balb-C mice were chosen because this mouse strain is known to develop good CD4 T cell responses. As shown in FIG. 3B, when performing the IFN-γ ELISPOT assay, a significant augmentation in the frequency of hyTERT specific IFN-γ secreting CD4 T-cells was observed in the spleen of ID and IM vaccinated Balb-C mice in comparison with control mice injected with PBS 1×. This was observed for the 2 II restricted peptides tested (p1106 and p1105, p<0.01 for ID and IM route). No significant difference in the frequency of specific CD4 T cells was observed between IM and ID route for both peptides p1105 and p1106.

Thus, pUF2 construct is able to promote the expansion of cTERT specific CD8 and CD4 T-cells in mice. We next wanted to show that cTERT specific CD8 T-cells exhibit a functional cytotoxic activity in vivo, which will be necessary to destroy tumor cells. In order to measure the in vivo cytolytic strength of the CD8$^+$ T-cell response elicited by pUF2 immunization, we performed an in vivo cytotoxicity test using carboxyfluorescein-diacetate succinimidyl ester (CFSE)-labelled, peptide-pulsed splenocytes as target cells. 7 week old C57/Bl6 mice which received a prime and boost vaccination with pUF2 via the ID or IM route as described before or mock-immunized with phosphate-buffered saline (PBS) were intravenously injected with $10^7$ target cells. Target cells were splenocytes from naïve congenic mice separately labelled with three different concentrations of CFSE and pulsed with individual peptides (p621 or p987) or left un-pulsed as an internal control. After 15-18 hours, spleen cells were obtained and the disappearance of peptide-pulsed cells in control versus immunized mice was quantified by fluorescence-activated cell sorting.

The inventors observed that mice developed CTLs against the 2 peptides p621 and p987 which had been previously identified in silico. Peptide 621 gives the strongest in vivo lysis. These results were concordant with the ones from the IFN-γ Elispot assays (FIG. 5A). Interestingly, a significant difference was observed between the two routes of immunization for p621. Indeed, for p621, the mean percent lysis was superior when pUF2 was injected via the ID route (mean ID=64.5% vs mean IM=11%). A non-significant difference was observed for p987 (mean ID=35.7% vs mean IM=21.3%). This confirms that the pUF2 ID vaccination would allow generating a stronger and larger CD8 T cell response that the IM route.

REFERENCES

Adolph, K. 1996 ed. "Viral Genome Methods" CRC Press, Florida de Fornel P, Delisle F, Devauchelle P, Rosenberg D. 2007. Effects of radiotherapy on pituitary corticotroph macrotumors in dogs: a retrospective study of 12 cases. Can Vet J 48: 481-486.

Dillman R O. 2011. Cancer Immunotherapy. Cancer Biotherapy and Radiopharmaceuticals 26: 1-64.

Disis M L, Bernhard H, Jaffee E M. 2009. Use of tumour-responsive T cells as cancer treatment. Lancet 373: 673-683.

Finn O J. 2008. Cancer immunology. N Engl J Med 358: 2704-2715.

Fridman W H, Pages F, Sautes-Fridman C, Galon J. 2012. The immune contexture in human tumours: impact on clinical outcome. Nat Rev Cancer 12: 298-306.

Hanahan D, Weinberg R A. 2011. Hallmarks of cancer: the next generation. Cell 144: 646-674.

Jourdier T M, Moste C, Bonnet M C, Delisle F, Tafani J P, Devauchelle P, Tartaglia J, Moingeon P. 2003. Local immunotherapy of spontaneous feline fibrosarcomas using recombinant poxviruses expressing interleukin 2 (IL2). Gene Therapy 10: 2126-2132.

Manley C A, Leibman N F, Wolchok J D, Riviere I C, Bartido S, Craft D M, Bergman P J. 2011. Xenogeneic murine tyrosinase DNA vaccine for malignant melanoma of the digit of dogs. J Vet Intern Med 25: 94-99.

Marconato L. 2011. The staging and treatment of multicentric high-grade lymphoma in dogs: a review of recent developments and future prospects. Vet J 188: 34-38.

Martinez P, Blasco M A. 2011. Telomeric and extra-telomeric roles for telomerase and the telomere-binding proteins. Nature Reviews Cancer 11: 161-176.

Mir L M. 2008. Application of electroporation gene therapy: past, current, and future. Methods Mol Biol 423: 3-17.

Murray, 1991, ed. "Gene Transfer and Expression Protocols" Humana Press, Clifton, N.J.

Sardesai N Y, Weiner D B. 2011. Electroporation delivery of DNA vaccines: prospects for success. Curr Opin Immunol 23: 421-429.

Topalian S L, Weiner G J, Pardoll D M. 2011. Cancer Immunotherapy Comes of Age. Journal of Clinical Oncology 29: 4828-4836.

Vascellari M, Baioni E, Ru G, Carminato A, Mutinelli F. 2009. Animal tumour registry of two provinces in northern Italy: incidence of spontaneous tumours in dogs and cats. BMC Vet Res 5: 39.

Yang, 1992, "Gene transfer into mammalian somatic cells in vivo", Crit. Rev. Biotech. 12: 335-356

Yang Y, Chen Y, Zhang C, Huang H, Weissman S M. 2002. Nucleolar localization of hTERT protein is associated with telomerase function. Exp Cell Res 277: 201-209.

Yazawa M, et al, 2003, J. Vet. Med. Sci 65(5):573-577

SEQUENCE LISTING

```
<160> NUMBER OF SEQ ID NOS: 16

<210> SEQ ID NO 1
<211> LENGTH: 3588
<212> TYPE: DNA
<213> ORGANISM: Artificial
<220> FEATURE:
<223> OTHER INFORMATION: pUF2 plasmid sequence
<220> FEATURE:
<221> NAME/KEY: CDS
<222> LOCATION: (13)..(3588)

<400> SEQUENCE: 1
aagcttgccg cc atg cag att ttc gtc aaa acc ctc acc ggc aag acc atc        51
              Met Gln Ile Phe Val Lys Thr Leu Thr Gly Lys Thr Ile
                1               5                  10 aca ttg gaa gtg gaa ccc agt gat act atc gaa aat gtt aaa gcc aaa          99
Thr Leu Glu Val Glu Pro Ser Asp Thr Ile Glu Asn Val Lys Ala Lys
     15                  20                  25 atc cag gat aag gag ggc att cct cct gac cag cag aga ctt att ttc         147
Ile Gln Asp Lys Glu Gly Ile Pro Pro Asp Gln Gln Arg Leu Ile Phe
 30                  35                  40                  45 gca ggc aaa cag ctg gag gac ggc aga aca ttg tct gac tac aac atc         195
Ala Gly Lys Gln Leu Glu Asp Gly Arg Thr Leu Ser Asp Tyr Asn Ile
                 50                  55                  60 cag aaa gag agc aca ctt cac ttg gtt ctc cgc ctt cgc gga gga cgg         243
Gln Lys Glu Ser Thr Leu His Leu Val Leu Arg Leu Arg Gly Gly Arg
             65                  70                  75 gcc ctc gtg gct cag tgt ctg gtg tgt gtc cca tgg gga gca cgg cct         291
Ala Leu Val Ala Gln Cys Leu Val Cys Val Pro Trp Gly Ala Arg Pro
         80                  85                  90 cca cca gca gcc ccc tgc ttt aga cag gtc agt tgc ctc aag gag ctc         339
Pro Pro Ala Ala Pro Cys Phe Arg Gln Val Ser Cys Leu Lys Glu Leu
     95                 100                 105 gtg gcc agg gtg gtt cag aga ctc tgc gag cgg ggt gcc cgg aat gtg         387
Val Ala Arg Val Val Gln Arg Leu Cys Glu Arg Gly Ala Arg Asn Val
110                 115                 120                 125 ctg gcc ttt gga ttc gct ctg ctt gac ggt gcc agg gga ggc cca cca         435
Leu Ala Phe Gly Phe Ala Leu Leu Asp Gly Ala Arg Gly Gly Pro Pro
                130                 135                 140 gtg gtg ttc acc aca tct gtg cgc agt tat ctg cca aac aca gtt acc         483
Val Val Phe Thr Thr Ser Val Arg Ser Tyr Leu Pro Asn Thr Val Thr
            145                 150                 155
```

```
                                                        -continued gag act ctg cgg gga tca gga gcc tgg ggc ttg ctg ctc agg cgc gtc        531
Glu Thr Leu Arg Gly Ser Gly Ala Trp Gly Leu Leu Leu Arg Arg Val
        160                 165                 170 ggt gac gac gtg ctt gcc cac ttg ctc acc cgg tgc gcc ctt tac gtc        579
Gly Asp Asp Val Leu Ala His Leu Leu Thr Arg Cys Ala Leu Tyr Val
    175                 180                 185 ctc gtc gct cct agt tgc gcc tac cag gtg tgt gga ccc ccc ctg tat        627
Leu Val Ala Pro Ser Cys Ala Tyr Gln Val Cys Gly Pro Pro Leu Tyr
190                 195                 200                 205 gat ctc tgt gct cca gca gcc act agg ccc ctg gct act tcc ggc cat        675
Asp Leu Cys Ala Pro Ala Ala Thr Arg Pro Leu Ala Thr Ser Gly His
                210                 215                 220 agg ccc ggc acc aga atg gat ctg cgg ccc aca cgg cag gca cgc aac        723
Arg Pro Gly Thr Arg Met Asp Leu Arg Pro Thr Arg Gln Ala Arg Asn
            225                 230                 235 gcc ggc gca cgg cgg aga aga ggt gct ggc ggc agc tct cct cct ttg        771
Ala Gly Ala Arg Arg Arg Gly Ala Gly Gly Ser Ser Pro Pro Leu
        240                 245                 250 gca aag aga cct agg cat gat gtt aaa acc cca gag cca gaa aga gga        819
Ala Lys Arg Pro Arg His Asp Val Lys Thr Pro Glu Pro Glu Arg Gly
    255                 260                 265 ccc gca tcc ccc agc tca cgc cac ccc cct ggc cgc gct cat gga ttg        867
Pro Ala Ser Pro Ser Ser Arg His Pro Pro Gly Arg Ala His Gly Leu
270                 275                 280                 285 tca gga ggc gaa cct ggc gcc gtc acc tca gcc cgc gcc gct gcc gag        915
Ser Gly Gly Glu Pro Gly Ala Val Thr Ser Ala Arg Ala Ala Ala Glu
                290                 295                 300 gca aat agc ggc gag ggc gga ccc cct gga aca agg ttg act tct gcc        963
Ala Asn Ser Gly Glu Gly Gly Pro Pro Gly Thr Arg Leu Thr Ser Ala
            305                 310                 315 ggc gca cag ctg tcc cgc cca cag gga gtg ccc ctg agt cat ctg agc       1011
Gly Ala Gln Leu Ser Arg Pro Gln Gly Val Pro Leu Ser His Leu Ser
        320                 325                 330 cat ccc gaa aca aag cac ttt ctt tac tgc ccc ggt gga aaa gaa cgg       1059
His Pro Glu Thr Lys His Phe Leu Tyr Cys Pro Gly Gly Lys Glu Arg
    335                 340                 345 ctg aga cca tcc ttc ttg ctc agc gct ttg cgc cct tcc ctg aca ggc       1107
Leu Arg Pro Ser Phe Leu Leu Ser Ala Leu Arg Pro Ser Leu Thr Gly
350                 355                 360                 365 gcc aga acc ctc ctg gaa gct atc ttc ctt gga tct aaa tcc cct agg       1155
Ala Arg Thr Leu Leu Glu Ala Ile Phe Leu Gly Ser Lys Ser Pro Arg
                370                 375                 380 ccc ggt gca gct agg cgg act agg agg ctc cct gcc aga tat tgg aga       1203
Pro Gly Ala Ala Arg Arg Thr Arg Arg Leu Pro Ala Arg Tyr Trp Arg
            385                 390                 395 atg cgc ccc ctg ttc agg gag ctc ctt gct aac cac gcc cgc tgc ccc       1251
Met Arg Pro Leu Phe Arg Glu Leu Leu Ala Asn His Ala Arg Cys Pro
        400                 405                 410 tac gac gcc ctt ctg cgc act cac tgt ccc ctg cgg gct cca gct ccc       1299
Tyr Asp Ala Leu Leu Arg Thr His Cys Pro Leu Arg Ala Pro Ala Pro
    415                 420                 425 gcc gag gga tct agt aga ggc gtg ggt ggc ggt gct ggc ggt tgt gcc       1347
Ala Glu Gly Ser Ser Arg Gly Val Gly Gly Gly Ala Gly Gly Cys Ala
430                 435                 440                 445 ctc ggc cgg cct cca ggt gcc cca cag gaa cag acc gat tca acc cgc       1395
Leu Gly Arg Pro Pro Gly Ala Pro Gln Glu Gln Thr Asp Ser Thr Arg
                450                 455                 460 ctt gtg cag ctc ctg agg cag cac agt agc cca tgg cag gtg tat gct       1443
Leu Val Gln Leu Leu Arg Gln His Ser Ser Pro Trp Gln Val Tyr Ala
            465                 470                 475
```

| | | | | | | | | | | | | | | | | |
|---|---|---|---|---|---|---|---|---|---|---|---|---|---|---|---|---|
| ttt | ctt | cgc | gct | tgt | ctg | tgc | cgc | ctc | gtg | ccc | gcc | ggt | ctg | tgg | ggc | 1491 |
| Phe | Leu | Arg | Ala | Cys | Leu | Cys | Arg | Leu | Val | Pro | Ala | Gly | Leu | Trp | Gly | |
| | | 480 | | | | 485 | | | | 490 | | | | | | |

| | | | | | | | | | | | | | | | | |
|---|---|---|---|---|---|---|---|---|---|---|---|---|---|---|---|---|
| agc | ggc | cac | aac | aga | aga | cgc | ttt | ttg | cgg | aat | gtg | aaa | aag | ttc | gtg | 1539 |
| Ser | Gly | His | Asn | Arg | Arg | Arg | Phe | Leu | Arg | Asn | Val | Lys | Lys | Phe | Val | |
| | 495 | | | | 500 | | | | | 505 | | | | | | |

| | | | | | | | | | | | | | | | | |
|---|---|---|---|---|---|---|---|---|---|---|---|---|---|---|---|---|
| tcc | ctg | gga | aag | cac | gct | aaa | ctg | tca | ttg | cag | gag | ctg | acc | tgg | aag | 1587 |
| Ser | Leu | Gly | Lys | His | Ala | Lys | Leu | Ser | Leu | Gln | Glu | Leu | Thr | Trp | Lys | |
| 510 | | | | | 515 | | | | | 520 | | | | | 525 | |

| | | | | | | | | | | | | | | | | |
|---|---|---|---|---|---|---|---|---|---|---|---|---|---|---|---|---|
| atg | cgg | gtg | cag | gat | tgt | gca | tgg | ctg | agg | ggc | tct | ccc | gga | gcc | cgc | 1635 |
| Met | Arg | Val | Gln | Asp | Cys | Ala | Trp | Leu | Arg | Gly | Ser | Pro | Gly | Ala | Arg | |
| | | | 530 | | | | | 535 | | | | | 540 | | | |

| | | | | | | | | | | | | | | | | |
|---|---|---|---|---|---|---|---|---|---|---|---|---|---|---|---|---|
| tgc | gtc | cca | gcc | gcc | gaa | cac | aga | cgg | cgc | gag | gag | gtg | ctc | gca | aag | 1683 |
| Cys | Val | Pro | Ala | Ala | Glu | His | Arg | Arg | Arg | Glu | Glu | Val | Leu | Ala | Lys | |
| | | | | 545 | | | | | 550 | | | | | 555 | | |

| | | | | | | | | | | | | | | | | |
|---|---|---|---|---|---|---|---|---|---|---|---|---|---|---|---|---|
| ctc | ttg | tgc | tgg | ctg | atg | gga | acc | tac | gtg | gtc | gaa | ctg | ctg | aaa | tct | 1731 |
| Leu | Leu | Cys | Trp | Leu | Met | Gly | Thr | Tyr | Val | Val | Glu | Leu | Leu | Lys | Ser | |
| | | | 560 | | | | | 565 | | | | | 570 | | | |

| | | | | | | | | | | | | | | | | |
|---|---|---|---|---|---|---|---|---|---|---|---|---|---|---|---|---|
| ttt | ttc | tat | gtc | act | gag | act | aca | ttc | cag | aag | aat | cgc | ctg | ttc | ttt | 1779 |
| Phe | Phe | Tyr | Val | Thr | Glu | Thr | Thr | Phe | Gln | Lys | Asn | Arg | Leu | Phe | Phe | |
| | 575 | | | | | 580 | | | | | 585 | | | | | |

| | | | | | | | | | | | | | | | | |
|---|---|---|---|---|---|---|---|---|---|---|---|---|---|---|---|---|
| tac | cgg | aaa | agg | atc | tgg | tcc | cag | ctt | cag | agc | att | ggc | atc | cgg | cag | 1827 |
| Tyr | Arg | Lys | Arg | Ile | Trp | Ser | Gln | Leu | Gln | Ser | Ile | Gly | Ile | Arg | Gln | |
| 590 | | | | | 595 | | | | | 600 | | | | | 605 | |

| | | | | | | | | | | | | | | | | |
|---|---|---|---|---|---|---|---|---|---|---|---|---|---|---|---|---|
| cat | ttt | aac | tct | gtt | cac | ctg | agg | gag | ctg | agc | gag | gca | gaa | gtg | agg | 1875 |
| His | Phe | Asn | Ser | Val | His | Leu | Arg | Glu | Leu | Ser | Glu | Ala | Glu | Val | Arg | |
| | | | | 610 | | | | | 615 | | | | | 620 | | |

| | | | | | | | | | | | | | | | | |
|---|---|---|---|---|---|---|---|---|---|---|---|---|---|---|---|---|
| cgc | cat | cag | gag | gcc | cgc | ccc | act | ctg | ctt | acc | tcc | aag | ctg | cgg | ttc | 1923 |
| Arg | His | Gln | Glu | Ala | Arg | Pro | Thr | Leu | Leu | Thr | Ser | Lys | Leu | Arg | Phe | |
| | | | 625 | | | | | 630 | | | | | 635 | | | |

| | | | | | | | | | | | | | | | | |
|---|---|---|---|---|---|---|---|---|---|---|---|---|---|---|---|---|
| ctg | cct | aaa | cca | tca | ggt | ctg | aga | ccc | att | gtc | aac | atg | gat | tac | gtg | 1971 |
| Leu | Pro | Lys | Pro | Ser | Gly | Leu | Arg | Pro | Ile | Val | Asn | Met | Asp | Tyr | Val | |
| | | | 640 | | | | | 645 | | | | | 650 | | | |

| | | | | | | | | | | | | | | | | |
|---|---|---|---|---|---|---|---|---|---|---|---|---|---|---|---|---|
| gtg | ggc | gcc | aga | aca | ttc | aga | aga | gac | aaa | aag | gtt | cgg | cat | ctc | acc | 2019 |
| Val | Gly | Ala | Arg | Thr | Phe | Arg | Arg | Asp | Lys | Lys | Val | Arg | His | Leu | Thr | |
| | 655 | | | | | 660 | | | | | 665 | | | | | |

| | | | | | | | | | | | | | | | | |
|---|---|---|---|---|---|---|---|---|---|---|---|---|---|---|---|---|
| tca | cag | gtt | aaa | aac | ctg | ttt | tct | gtt | ctg | aac | tac | gaa | agg | gcc | agg | 2067 |
| Ser | Gln | Val | Lys | Asn | Leu | Phe | Ser | Val | Leu | Asn | Tyr | Glu | Arg | Ala | Arg | |
| 670 | | | | | 675 | | | | | 680 | | | | | 685 | |

| | | | | | | | | | | | | | | | | |
|---|---|---|---|---|---|---|---|---|---|---|---|---|---|---|---|---|
| agg | cca | tca | ctg | ctg | ggt | gcc | agt | gtg | ctg | gga | atg | gac | gat | att | cac | 2115 |
| Arg | Pro | Ser | Leu | Leu | Gly | Ala | Ser | Val | Leu | Gly | Met | Asp | Asp | Ile | His | |
| | | | | 690 | | | | | 695 | | | | | 700 | | |

| | | | | | | | | | | | | | | | | |
|---|---|---|---|---|---|---|---|---|---|---|---|---|---|---|---|---|
| aga | gtc | tgg | cgg | agc | ttc | gtg | ctt | cgg | gtg | aga | gct | cag | gac | ccc | gcc | 2163 |
| Arg | Val | Trp | Arg | Ser | Phe | Val | Leu | Arg | Val | Arg | Ala | Gln | Asp | Pro | Ala | |
| | | | 705 | | | | | 710 | | | | | 715 | | | |

| | | | | | | | | | | | | | | | | |
|---|---|---|---|---|---|---|---|---|---|---|---|---|---|---|---|---|
| cca | cag | ttg | tat | ttt | gtc | aag | gtc | gat | gtg | act | ggt | gct | tat | gac | gct | 2211 |
| Pro | Gln | Leu | Tyr | Phe | Val | Lys | Val | Asp | Val | Thr | Gly | Ala | Tyr | Asp | Ala | |
| | | | 720 | | | | | 725 | | | | | 730 | | | |

| | | | | | | | | | | | | | | | | |
|---|---|---|---|---|---|---|---|---|---|---|---|---|---|---|---|---|
| ctc | cct | cag | gac | aaa | ttg | gtg | gag | gtg | atc | gct | aat | gtc | atc | cgc | ccc | 2259 |
| Leu | Pro | Gln | Asp | Lys | Leu | Val | Glu | Val | Ile | Ala | Asn | Val | Ile | Arg | Pro | |
| | | 735 | | | | | 740 | | | | | 745 | | | | |

| | | | | | | | | | | | | | | | | |
|---|---|---|---|---|---|---|---|---|---|---|---|---|---|---|---|---|
| cag | gaa | aat | aca | tac | tgc | gtg | cgg | cat | tac | gct | gtg | gtg | cag | cgc | acc | 2307 |
| Gln | Glu | Asn | Thr | Tyr | Cys | Val | Arg | His | Tyr | Ala | Val | Val | Gln | Arg | Thr | |
| 750 | | | | | 755 | | | | | 760 | | | | | 765 | |

| | | | | | | | | | | | | | | | | |
|---|---|---|---|---|---|---|---|---|---|---|---|---|---|---|---|---|
| gca | cag | ggc | cac | gtg | agg | aaa | tcc | ttc | aag | cgg | cat | gtg | tcc | acc | ttc | 2355 |
| Ala | Gln | Gly | His | Val | Arg | Lys | Ser | Phe | Lys | Arg | His | Val | Ser | Thr | Phe | |
| | | | | 770 | | | | | 775 | | | | | 780 | | |

| | | | | | | | | | | | | | | | | |
|---|---|---|---|---|---|---|---|---|---|---|---|---|---|---|---|---|
| gtc | gac | ctc | cag | cca | tat | atg | cgc | cag | ttt | gtg | gag | cac | ctg | cag | gaa | 2403 |
| Val | Asp | Leu | Gln | Pro | Tyr | Met | Arg | Gln | Phe | Val | Glu | His | Leu | Gln | Glu | |

|     |     |
| --- | --- |
| act tca agc ctt agg gat gcc gtt gtt atc gag cag agt tct agt ctc<br>Thr Ser Ser Leu Arg Asp Ala Val Val Ile Glu Gln Ser Ser Ser Leu<br>800                  805             810 | 2451 |
| aac gag acc gga cac agt ctc ttc cac ctc ttt ctg agg ctc gtg cat<br>Asn Glu Thr Gly His Ser Leu Phe His Leu Phe Leu Arg Leu Val His<br>   815               820             825 | 2499 |
| aat cat gtc atc cgc att gga gga aaa tct tat gtt cag tgc cag ggc<br>Asn His Val Ile Arg Ile Gly Gly Lys Ser Tyr Val Gln Cys Gln Gly<br>830                  835            840             845 | 2547 |
| atc cct cag ggt tct atc ctg tca act ctg ctc tgc tcc ttg tgt tac<br>Ile Pro Gln Gly Ser Ile Leu Ser Thr Leu Leu Cys Ser Leu Cys Tyr<br>              850             855             860 | 2595 |
| ggc gat atg gaa agt agg ctt ttc tca gga atc cag cag gac ggc gtc<br>Gly Asp Met Glu Ser Arg Leu Phe Ser Gly Ile Gln Gln Asp Gly Val<br>         865              870             875 | 2643 |
| ctg ctg cgg ctg ttt ctt ctg gtg aca cct cac ctg gca cag gcc cag<br>Leu Leu Arg Leu Phe Leu Leu Val Thr Pro His Leu Ala Gln Ala Gln<br>880                  885             890 | 2691 |
| gcc ttc ctg cgc aca ctg gtg agc gga gtg cct gag tac ggc tgt acc<br>Ala Phe Leu Arg Thr Leu Val Ser Gly Val Pro Glu Tyr Gly Cys Thr<br>   895               900             905 | 2739 |
| gcc aac ctg cag aag aca gcc gtg aat ttt cca gtg gac acc ggt gct<br>Ala Asn Leu Gln Lys Thr Ala Val Asn Phe Pro Val Asp Thr Gly Ala<br>910                  915            920             925 | 2787 |
| cca ggc tcc gcc gca cct ctg cag ttg ccc gca cat tgt ctc ttt cct<br>Pro Gly Ser Ala Ala Pro Leu Gln Leu Pro Ala His Cys Leu Phe Pro<br>              930             935             940 | 2835 |
| tgg tgt ggc ctg ctc ctc gac acc cgg act ttg gaa gtc ttt tgc gat<br>Trp Cys Gly Leu Leu Leu Asp Thr Arg Thr Leu Glu Val Phe Cys Asp<br>         945            950             955 | 2883 |
| tac tcc agc tat gca cag aca tcc att agg agc agc ctg aca ttc agc<br>Tyr Ser Ser Tyr Ala Gln Thr Ser Ile Arg Ser Ser Leu Thr Phe Ser<br>960                  965            970 | 2931 |
| cag ggc aca cgg ccc ggc cgc aat atg agg aga aag ttg ctc gcc gtt<br>Gln Gly Thr Arg Pro Gly Arg Asn Met Arg Arg Lys Leu Leu Ala Val<br>   975               980            985 | 2979 |
| atg aga ctc aag tgc tgt gca gtc ttt ctt gat  ctg cag gtc aat tct<br>Met Arg Leu Lys Cys Cys Ala Val Phe Leu Asp Leu Gln Val Asn Ser<br>990                  995            1000          1005 | 3027 |
| att cat acc gtt tac  acc aac atc tat aaa  att ttc ctg ctc cag<br>Ile His Thr Val Tyr Thr Asn Ile Tyr Lys Ile Phe Leu Leu Gln<br>              1010            1015           1020 | 3072 |
| gca tat aga ttt cac  gcc tgc gtg ttg cag  ttc cca ttc aat cag<br>Ala Tyr Arg Phe His Ala Cys Val Leu Gln Phe Pro Phe Asn Gln<br>              1025            1030           1035 | 3117 |
| ccc gtt cgg aag aac  ccc agt ttc ttt ctc  agg gtt att gct gat<br>Pro Val Arg Lys Asn Pro Ser Phe Phe Leu Arg Val Ile Ala Asp<br>              1040            1045           1050 | 3162 |
| acc gcc tcc cgc tgt  tac tcc ctg ctt aag  gcc aag aac aca gga<br>Thr Ala Ser Arg Cys Tyr Ser Leu Leu Lys Ala Lys Asn Thr Gly<br>              1055            1060           1065 | 3207 |
| ctt tca ttg ggt gct  aaa ggc gcc agt gga  cct ttc cct tct gaa<br>Leu Ser Leu Gly Ala Lys Gly Ala Ser Gly Pro Phe Pro Ser Glu<br>              1070            1075           1080 | 3252 |
| gcc gct cgg tgg ctc  tgt ttg cac gca ttc  ctt ctg aag ttg gct<br>Ala Ala Arg Trp Leu Cys Leu His Ala Phe Leu Leu Lys Leu Ala<br>              1085            1090           1095 | 3297 |
| aga cac agc tct act  tac aga tgc ctt ctg  ggc ccc ctt aga gcc | 3342 |

```
Arg His Ser Ser Thr Tyr Arg Cys Leu Leu Gly Pro Leu Arg Ala
            1100                1105                1110 gca aag gcc cag ctc agg aga cag ctg cca cgg gct acc ctg gac      3387
Ala Lys Ala Gln Leu Arg Arg Gln Leu Pro Arg Ala Thr Leu Asp
            1115                1120                1125 gcc ctg gag gca gca gca agc cct ggc ctg cca gca gat ttt cgg      3432
Ala Leu Glu Ala Ala Ala Ser Pro Gly Leu Pro Ala Asp Phe Arg
            1130                1135                1140 acc att ctg gat aag ggt caa gac aat tct gca gat atc cag cac      3477
Thr Ile Leu Asp Lys Gly Gln Asp Asn Ser Ala Asp Ile Gln His
            1145                1150                1155 agt ggc ggc cgc tcg agt cta gag ggc ccg cgg ttc gaa ggt aag      3522
Ser Gly Gly Arg Ser Ser Leu Glu Gly Pro Arg Phe Glu Gly Lys
            1160                1165                1170 cct atc cct aac cct ctc ctc ggt ctc gat tct acg cgt acc ggt      3567
Pro Ile Pro Asn Pro Leu Leu Gly Leu Asp Ser Thr Arg Thr Gly
            1175                1180                1185 cat cat cac cat cac cat tga                                       3588
His His His His His His
            1190
```

```
<210> SEQ ID NO 2
<211> LENGTH: 1191
<212> TYPE: PRT
<213> ORGANISM: Artificial
<220> FEATURE:
<223> OTHER INFORMATION: Synthetic Construct

<400> SEQUENCE: 2

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Arg Ala Leu Val
65                  70                  75                  80

Ala Gln Cys Leu Val Cys Val Pro Trp Gly Ala Arg Pro Pro Ala
                85                  90                  95

Ala Pro Cys Phe Arg Gln Val Ser Cys Leu Lys Glu Leu Val Ala Arg
            100                 105                 110

Val Val Gln Arg Leu Cys Glu Arg Gly Ala Arg Asn Val Leu Ala Phe
        115                 120                 125

Gly Phe Ala Leu Leu Asp Gly Ala Arg Gly Pro Pro Val Val Phe
    130                 135                 140

Thr Thr Ser Val Arg Ser Tyr Leu Pro Asn Thr Val Thr Glu Thr Leu
145                 150                 155                 160

Arg Gly Ser Gly Ala Trp Gly Leu Leu Leu Arg Arg Val Gly Asp Asp
                165                 170                 175

Val Leu Ala His Leu Leu Thr Arg Cys Ala Leu Tyr Val Leu Val Ala
            180                 185                 190

Pro Ser Cys Ala Tyr Gln Val Cys Gly Pro Pro Leu Tyr Asp Leu Cys
        195                 200                 205

Ala Pro Ala Ala Thr Arg Pro Leu Ala Thr Ser Gly His Arg Pro Gly
    210                 215                 220
```

-continued

Thr Arg Met Asp Leu Arg Pro Thr Arg Gln Ala Arg Asn Ala Gly Ala
225                 230                 235                 240

Arg Arg Arg Arg Gly Ala Gly Gly Ser Ser Pro Pro Leu Ala Lys Arg
            245                 250                 255

Pro Arg His Asp Val Lys Thr Pro Glu Pro Glu Arg Gly Pro Ala Ser
        260                 265                 270

Pro Ser Ser Arg His Pro Pro Gly Arg Ala His Gly Leu Ser Gly Gly
    275                 280                 285

Glu Pro Gly Ala Val Thr Ser Ala Arg Ala Ala Glu Ala Asn Ser
290                 295                 300

Gly Glu Gly Gly Pro Pro Gly Thr Arg Leu Thr Ser Ala Gly Ala Gln
305                 310                 315                 320

Leu Ser Arg Pro Gln Gly Val Pro Leu Ser His Leu Ser His Pro Glu
            325                 330                 335

Thr Lys His Phe Leu Tyr Cys Pro Gly Gly Lys Glu Arg Leu Arg Pro
        340                 345                 350

Ser Phe Leu Leu Ser Ala Leu Arg Pro Ser Leu Thr Gly Ala Arg Thr
    355                 360                 365

Leu Leu Glu Ala Ile Phe Leu Gly Ser Lys Ser Pro Arg Pro Gly Ala
370                 375                 380

Ala Arg Arg Thr Arg Arg Leu Pro Ala Arg Tyr Trp Arg Met Arg Pro
385                 390                 395                 400

Leu Phe Arg Glu Leu Leu Ala Asn His Ala Arg Cys Pro Tyr Asp Ala
            405                 410                 415

Leu Leu Arg Thr His Cys Pro Leu Arg Ala Pro Ala Pro Ala Glu Gly
        420                 425                 430

Ser Ser Arg Gly Val Gly Gly Ala Gly Gly Cys Ala Leu Gly Arg
    435                 440                 445

Pro Pro Gly Ala Pro Gln Glu Gln Thr Asp Ser Thr Arg Leu Val Gln
450                 455                 460

Leu Leu Arg Gln His Ser Ser Pro Trp Gln Val Tyr Ala Phe Leu Arg
465                 470                 475                 480

Ala Cys Leu Cys Arg Leu Val Pro Ala Gly Leu Trp Gly Ser Gly His
            485                 490                 495

Asn Arg Arg Arg Phe Leu Arg Asn Val Lys Lys Phe Val Ser Leu Gly
        500                 505                 510

Lys His Ala Lys Leu Ser Leu Gln Glu Leu Thr Trp Lys Met Arg Val
    515                 520                 525

Gln Asp Cys Ala Trp Leu Arg Gly Ser Pro Gly Ala Arg Cys Val Pro
530                 535                 540

Ala Ala Glu His Arg Arg Arg Glu Glu Val Leu Ala Lys Leu Leu Cys
545                 550                 555                 560

Trp Leu Met Gly Thr Tyr Val Val Glu Leu Leu Lys Ser Phe Phe Tyr
            565                 570                 575

Val Thr Glu Thr Thr Phe Gln Lys Asn Arg Leu Phe Phe Tyr Arg Lys
        580                 585                 590

Arg Ile Trp Ser Gln Leu Gln Ser Ile Gly Ile Arg Gln His Phe Asn
    595                 600                 605

Ser Val His Leu Arg Glu Leu Ser Glu Ala Glu Val Arg Arg His Gln
610                 615                 620

Glu Ala Arg Pro Thr Leu Leu Thr Ser Lys Leu Arg Phe Leu Pro Lys
625                 630                 635                 640

Pro Ser Gly Leu Arg Pro Ile Val Asn Met Asp Tyr Val Val Gly Ala

-continued

```
                645                 650                 655
Arg Thr Phe Arg Arg Asp Lys Lys Val Arg His Leu Thr Ser Gln Val
            660                 665                 670
Lys Asn Leu Phe Ser Val Leu Asn Tyr Glu Arg Ala Arg Arg Pro Ser
            675                 680                 685
Leu Leu Gly Ala Ser Val Leu Gly Met Asp Asp Ile His Arg Val Trp
690                 695                 700
Arg Ser Phe Val Leu Arg Val Arg Ala Gln Asp Pro Ala Pro Gln Leu
705                 710                 715                 720
Tyr Phe Val Lys Val Asp Val Thr Gly Ala Tyr Asp Ala Leu Pro Gln
            725                 730                 735
Asp Lys Leu Val Glu Val Ile Ala Asn Val Ile Arg Pro Gln Glu Asn
            740                 745                 750
Thr Tyr Cys Val Arg His Tyr Ala Val Val Gln Arg Thr Ala Gln Gly
            755                 760                 765
His Val Arg Lys Ser Phe Lys Arg His Val Ser Thr Phe Val Asp Leu
            770                 775                 780
Gln Pro Tyr Met Arg Gln Phe Val Glu His Leu Gln Glu Thr Ser Ser
785                 790                 795                 800
Leu Arg Asp Ala Val Val Ile Glu Gln Ser Ser Ser Leu Asn Glu Thr
            805                 810                 815
Gly His Ser Leu Phe His Leu Phe Leu Arg Leu Val His Asn His Val
            820                 825                 830
Ile Arg Ile Gly Gly Lys Ser Tyr Val Gln Cys Gln Gly Ile Pro Gln
            835                 840                 845
Gly Ser Ile Leu Ser Thr Leu Leu Cys Ser Leu Cys Tyr Gly Asp Met
850                 855                 860
Glu Ser Arg Leu Phe Ser Gly Ile Gln Gln Asp Gly Val Leu Leu Arg
865                 870                 875                 880
Leu Phe Leu Leu Val Thr Pro His Leu Ala Gln Ala Gln Ala Phe Leu
            885                 890                 895
Arg Thr Leu Val Ser Gly Val Pro Glu Tyr Gly Cys Thr Ala Asn Leu
            900                 905                 910
Gln Lys Thr Ala Val Asn Phe Pro Val Asp Thr Gly Ala Pro Gly Ser
            915                 920                 925
Ala Ala Pro Leu Gln Leu Pro Ala His Cys Leu Phe Pro Trp Cys Gly
            930                 935                 940
Leu Leu Leu Asp Thr Arg Thr Leu Glu Val Phe Cys Asp Tyr Ser Ser
945                 950                 955                 960
Tyr Ala Gln Thr Ser Ile Arg Ser Ser Leu Thr Phe Ser Gly Thr
            965                 970                 975
Arg Pro Gly Arg Asn Met Arg Arg Lys Leu Leu Ala Val Met Arg Leu
            980                 985                 990
Lys Cys Cys Ala Val Phe Leu Asp Leu Gln Val Asn Ser Ile His Thr
            995                 1000                1005
Val Tyr Thr Asn Ile Tyr Lys Ile Phe Leu Leu Gln Ala Tyr Arg
            1010                1015                1020
Phe His Ala Cys Val Leu Gln Phe Pro Phe Asn Gln Pro Val Arg
            1025                1030                1035
Lys Asn Pro Ser Phe Phe Leu Arg Val Ile Ala Asp Thr Ala Ser
            1040                1045                1050
Arg Cys Tyr Ser Leu Leu Lys Ala Lys Asn Thr Gly Leu Ser Leu
            1055                1060                1065
```

```
Gly Ala  Lys Gly Ala Ser  Gly Pro Phe Pro Ser  Glu Ala Ala Arg
    1070         1075             1080

Trp Leu  Cys Leu His Ala  Phe Leu Leu Lys Leu  Ala Arg His Ser
    1085         1090             1095

Ser Thr  Tyr Arg Cys Leu  Leu Gly Pro Leu Arg  Ala Ala Lys Ala
    1100         1105             1110

Gln Leu  Arg Arg Gln Leu  Pro Arg Ala Thr Leu  Asp Ala Leu Glu
    1115         1120             1125

Ala Ala  Ala Ser Pro Gly  Leu Pro Ala Asp Phe  Arg Thr Ile Leu
    1130         1135             1140

Asp Lys  Gly Gln Asp Asn  Ser Ala Asp Ile Gln  His Ser Gly Gly
    1145         1150             1155

Arg Ser  Ser Leu Glu Gly  Pro Arg Phe Glu Gly  Lys Pro Ile Pro
    1160         1165             1170

Asn Pro  Leu Leu Gly Leu  Asp Ser Thr Arg Thr  Gly His His His
    1175         1180             1185

His His  His
    1190

<210> SEQ ID NO 3
<211> LENGTH: 3564
<212> TYPE: DNA
<213> ORGANISM: Artificial
<220> FEATURE:
<223> OTHER INFORMATION: pCDT plasmid sequence
<220> FEATURE:
<221> NAME/KEY: CDS
<222> LOCATION: (13)..(3552)

<400> SEQUENCE: 3
aagcttgccg cc atg cag att ttc gtc aaa acc ctc acc ggc aag acc atc       51
              Met Gln Ile Phe Val Lys Thr Leu Thr Gly Lys Thr Ile
                1               5                  10 aca ttg gaa gtg gaa ccc agt gat act atc gaa aat gtt aaa gcc aaa        99
Thr Leu Glu Val Glu Pro Ser Asp Thr Ile Glu Asn Val Lys Ala Lys
 15              20                  25 atc cag gat aag gag ggc att cct cct gac cag cag aga ctt att ttc       147
Ile Gln Asp Lys Glu Gly Ile Pro Pro Asp Gln Gln Arg Leu Ile Phe
 30              35                  40                  45 gca ggc aaa cag ctg gag gac ggc aga aca ttg tct gac tac aac atc       195
Ala Gly Lys Gln Leu Glu Asp Gly Arg Thr Leu Ser Asp Tyr Asn Ile
         50                  55                  60 cag aaa gag agc aca ctt cac ttg gtt ctc cgc ctt cgc gga gga cgg       243
Gln Lys Glu Ser Thr Leu His Leu Val Leu Arg Leu Arg Gly Gly Arg
 65                  70                  75 gcc ctc gtg gct cag tgt ctg gtg tgt gtc cca tgg gga gca cgg cct       291
Ala Leu Val Ala Gln Cys Leu Val Cys Val Pro Trp Gly Ala Arg Pro
         80                  85                  90 cca cca gca gcc ccc tgc ttt aga cag gtc agt tgc ctc aag gag ctc       339
Pro Pro Ala Ala Pro Cys Phe Arg Gln Val Ser Cys Leu Lys Glu Leu
 95                  100                 105 gtg gcc agg gtg gtt cag aga ctc tgc gag cgg ggt gcc cgg aac gtc       387
Val Ala Arg Val Val Gln Arg Leu Cys Glu Arg Gly Ala Arg Asn Val
110                 115                 120                 125 ctc gct ttt gga ttc gca ctg ctg gac ggc gct cgc gga ggc cca ccc       435
Leu Ala Phe Gly Phe Ala Leu Leu Asp Gly Ala Arg Gly Gly Pro Pro
                130                 135                 140 gtg gcc ttt aca acc agc gtg cgg tca tac ctg ccc aac act gtg aca       483
Val Ala Phe Thr Thr Ser Val Arg Ser Tyr Leu Pro Asn Thr Val Thr
```

-continued

```
                    145                 150                 155
gag aca ctg aga ggc tcc ggc gct tgg ggc ctt ctg ttg agg cgc gtt        531
Glu Thr Leu Arg Gly Ser Gly Ala Trp Gly Leu Leu Leu Arg Arg Val
        160                 165                 170 ggc gac gat gtg ttg aca cac ctg ctc gcc agg tgc gca ctt tac ctg        579
Gly Asp Asp Val Leu Thr His Leu Leu Ala Arg Cys Ala Leu Tyr Leu
175                 180                 185 ctg gtg gcc cca agt tgc gcc tac cag gtg tgc gga cct cct ttg tac        627
Leu Val Ala Pro Ser Cys Ala Tyr Gln Val Cys Gly Pro Pro Leu Tyr
190                 195                 200                 205 gac ctc tgt gcc cct gcc tct ttg cca ctg cct gcc cct ggc ctg cct        675
Asp Leu Cys Ala Pro Ala Ser Leu Pro Leu Pro Ala Pro Gly Leu Pro
                210                 215                 220 gga ctt cct ggt ctg cct ggt ctc ggc gct gga gct ggc gcc tcc gca        723
Gly Leu Pro Gly Leu Pro Gly Leu Gly Ala Gly Ala Gly Ala Ser Ala
                225                 230                 235 gat ctc agg cct acc cgc cag gca cag aat agc gga gcc agg cgc cgc        771
Asp Leu Arg Pro Thr Arg Gln Ala Gln Asn Ser Gly Ala Arg Arg Arg
                240                 245                 250 cgg ggt agc cca ggt tct ggc gtc ccc ctg gct aaa aga cca cgg agg        819
Arg Gly Ser Pro Gly Ser Gly Val Pro Leu Ala Lys Arg Pro Arg Arg
255                 260                 265 tca gtt gct tcc gaa ccc gag cgg ggc gca cat cgc tcc ttt ccc aga        867
Ser Val Ala Ser Glu Pro Glu Arg Gly Ala His Arg Ser Phe Pro Arg
270                 275                 280                 285 gcc cag cag cca cct gtg tct gag gct cca gca gtg aca ccc gct gtg        915
Ala Gln Gln Pro Pro Val Ser Glu Ala Pro Ala Val Thr Pro Ala Val
                    290                 295                 300 gcc gcc agc cct gcc gcc tca tgg gaa gga gga ccc cct gga acc agg        963
Ala Ala Ser Pro Ala Ala Ser Trp Glu Gly Gly Pro Pro Gly Thr Arg
                305                 310                 315 ccc act acc ccc gct tgg cac ccc tac cct gga ccc cag ggc gtc cct       1011
Pro Thr Thr Pro Ala Trp His Pro Tyr Pro Gly Pro Gln Gly Val Pro
                320                 325                 330 cat gat cct gct cac cca gaa acc aag cgg ttc ctg tac tgc agc gga       1059
His Asp Pro Ala His Pro Glu Thr Lys Arg Phe Leu Tyr Cys Ser Gly
        335                 340                 345 ggt aga gaa cgc ttg cgc cca agt ttt ctg ctc agc gcc ctg cct cca       1107
Gly Arg Glu Arg Leu Arg Pro Ser Phe Leu Leu Ser Ala Leu Pro Pro
350                 355                 360                 365 act ctt tcc gga gcc cgg aaa ctc gtg gaa acc atc ttt ctc ggt agc       1155
Thr Leu Ser Gly Ala Arg Lys Leu Val Glu Thr Ile Phe Leu Gly Ser
                370                 375                 380 gct cct cag aaa cca gga gcc gct agg cgg atg cgc aga ctg cct gca       1203
Ala Pro Gln Lys Pro Gly Ala Ala Arg Arg Met Arg Arg Leu Pro Ala
                385                 390                 395 cgc tac tgg cgc atg cgc cca ctc ttt cag gag ctg ctg gga aat cat       1251
Arg Tyr Trp Arg Met Arg Pro Leu Phe Gln Glu Leu Leu Gly Asn His
                400                 405                 410 gca agg tgc ccc tat cgg gct ctg ctt cgg act cac tgt cca ctg aga       1299
Ala Arg Cys Pro Tyr Arg Ala Leu Leu Arg Thr His Cys Pro Leu Arg
        415                 420                 425 gct atg gca gca aag gaa gga agt gga aac cag gcc cat aga gga gtc       1347
Ala Met Ala Ala Lys Glu Gly Ser Gly Asn Gln Ala His Arg Gly Val
430                 435                 440                 445 ggt atc tgt cca ctg gag cgc ccc gtt gct gcc ccc cag gaa cag acc       1395
Gly Ile Cys Pro Leu Glu Arg Pro Val Ala Ala Pro Gln Glu Gln Thr
                    450                 455                 460 gat tca acc cgc ctt gtg cag ctc ctg agg cag cac agt agc cca tgg       1443
Asp Ser Thr Arg Leu Val Gln Leu Leu Arg Gln His Ser Ser Pro Trp
```

```
                Asp Ser Thr Arg Leu Val Gln Leu Leu Arg Gln His Ser Ser Pro Trp
                            465                 470                 475 cag gtg tat gct ttt ctt cgc gct tgt ctg tgc cgc ctc gtg ccc gcc         1491
Gln Val Tyr Ala Phe Leu Arg Ala Cys Leu Cys Arg Leu Val Pro Ala
                480                 485                 490 ggt ctg tgg ggc agc ggc cac aac aga aga cgc ttt ttg cgg aat gtg         1539
Gly Leu Trp Gly Ser Gly His Asn Arg Arg Arg Phe Leu Arg Asn Val
    495                 500                 505 aaa aag ttc gtg tcc ctg gga aag cac gct aaa ctg tca ttg cag gag         1587
Lys Lys Phe Val Ser Leu Gly Lys His Ala Lys Leu Ser Leu Gln Glu
510                 515                 520                 525 ctg acc tgg aag atg cgg gtg cag gat tgt gca tgg ctg agg ggc tct         1635
Leu Thr Trp Lys Met Arg Val Gln Asp Cys Ala Trp Leu Arg Gly Ser
                530                 535                 540 ccc gga gcc cgc tgc gtc cca gcc gcc gaa cac aga cgg cgc gag gag         1683
Pro Gly Ala Arg Cys Val Pro Ala Ala Glu His Arg Arg Arg Glu Glu
                545                 550                 555 gtg ctc gca aag ctc ttg tgc tgg ctg atg gga acc tac gtg gtc gaa         1731
Val Leu Ala Lys Leu Leu Cys Trp Leu Met Gly Thr Tyr Val Val Glu
                560                 565                 570 ctg ctg aaa tct ttt ttc tat gtc act gag act aca ttc cag aag aat         1779
Leu Leu Lys Ser Phe Phe Tyr Val Thr Glu Thr Thr Phe Gln Lys Asn
    575                 580                 585 cgc ctg ttc ttt tac cgg aaa agg atc tgg tcc cag ctt cag agc att         1827
Arg Leu Phe Phe Tyr Arg Lys Arg Ile Trp Ser Gln Leu Gln Ser Ile
590                 595                 600                 605 ggc atc cgg cag cat ttt aac tct gtt cac ctg agg gag ctg agc gag         1875
Gly Ile Arg Gln His Phe Asn Ser Val His Leu Arg Glu Leu Ser Glu
                610                 615                 620 gca gaa gtg agg cgc cat cag gag gcc cgc ccc act ctg ctt acc tcc         1923
Ala Glu Val Arg Arg His Gln Glu Ala Arg Pro Thr Leu Leu Thr Ser
                625                 630                 635 aag ctg cgg ttc ctg cct aaa cca tca ggt ctg aga ccc att gtc aac         1971
Lys Leu Arg Phe Leu Pro Lys Pro Ser Gly Leu Arg Pro Ile Val Asn
                640                 645                 650 atg gat tac gtg gtg ggc gcc aga aca ttc aga aga gac aaa aag gtt         2019
Met Asp Tyr Val Val Gly Ala Arg Thr Phe Arg Arg Asp Lys Lys Val
    655                 660                 665 cgg cat ctc acc tca cag gtt aaa aac ctg ttt tct gtt ctg aac tac         2067
Arg His Leu Thr Ser Gln Val Lys Asn Leu Phe Ser Val Leu Asn Tyr
670                 675                 680                 685 gaa agg gcc agg agg cca tca ctg ctg ggt gcc agt gtg ctg gga atg         2115
Glu Arg Ala Arg Arg Pro Ser Leu Leu Gly Ala Ser Val Leu Gly Met
                690                 695                 700 gac gat att cac aga gtc tgg cgg agc ttc gtg ctt cgg gtg aga gct         2163
Asp Asp Ile His Arg Val Trp Arg Ser Phe Val Leu Arg Val Arg Ala
                705                 710                 715 cag gac ccc gcc cca cag ttg tat ttt gtc aag gtc gat gtg act ggt         2211
Gln Asp Pro Ala Pro Gln Leu Tyr Phe Val Lys Val Asp Val Thr Gly
                720                 725                 730 gct tat gac gct ctc cct cag gac aaa ttg gtg gag gtg atc gct aat         2259
Ala Tyr Asp Ala Leu Pro Gln Asp Lys Leu Val Glu Val Ile Ala Asn
    735                 740                 745 gtc atc cgc ccc cag gaa aat aca tac tgc gtg cgg cat tac gct gtg         2307
Val Ile Arg Pro Gln Glu Asn Thr Tyr Cys Val Arg His Tyr Ala Val
750                 755                 760                 765 gtg cag cgc acc gca cag ggc cac gtg agg aaa tcc ttc aag cgg cat         2355
Val Gln Arg Thr Ala Gln Gly His Val Arg Lys Ser Phe Lys Arg His
                770                 775                 780
```

```
gtg tcc acc ttc gtc gac ctc cag cca tat atg cgc cag ttt gtg gag      2403
Val Ser Thr Phe Val Asp Leu Gln Pro Tyr Met Arg Gln Phe Val Glu
            785                 790                 795 cac ctg cag gaa act tca agc ctt agg gat gcc gtt gtt atc gag cag      2451
His Leu Gln Glu Thr Ser Ser Leu Arg Asp Ala Val Val Ile Glu Gln
        800                 805                 810 agt tct agt ctc aac gag acc gga cac agt ctc ttc cac ctc ttt ctg      2499
Ser Ser Ser Leu Asn Glu Thr Gly His Ser Leu Phe His Leu Phe Leu
    815                 820                 825 agg ctc gtg cat aat cat gtc atc cgc att gga gga aaa tct tat gtt      2547
Arg Leu Val His Asn His Val Ile Arg Ile Gly Gly Lys Ser Tyr Val
830                 835                 840                 845 cag tgc cag ggc atc cct cag ggt tct atc ctg tca act ctg ctc tgc      2595
Gln Cys Gln Gly Ile Pro Gln Gly Ser Ile Leu Ser Thr Leu Leu Cys
                850                 855                 860 tcc ttg tgt tac ggc gat atg gaa agt agg ctt ttc tca gga atc cag      2643
Ser Leu Cys Tyr Gly Asp Met Glu Ser Arg Leu Phe Ser Gly Ile Gln
            865                 870                 875 cag gac ggc gtc ctg ctg cgg ctg ttt ctt ctg gtg aca cct cac ctg      2691
Gln Asp Gly Val Leu Leu Arg Leu Phe Leu Leu Val Thr Pro His Leu
        880                 885                 890 gca cag gcc cag gcc ttc ctg cgc aca ctg gtg agc gga gtg cct gag      2739
Ala Gln Ala Gln Ala Phe Leu Arg Thr Leu Val Ser Gly Val Pro Glu
    895                 900                 905 tac ggc tgt acc gcc aac ctg cag aag aca gcc gtg aat ttt cca gtg      2787
Tyr Gly Cys Thr Ala Asn Leu Gln Lys Thr Ala Val Asn Phe Pro Val
910                 915                 920                 925 gac acc ggt gct cca ggc tcc gcc gca cct ctg cag ttg ccc gca cat      2835
Asp Thr Gly Ala Pro Gly Ser Ala Ala Pro Leu Gln Leu Pro Ala His
                930                 935                 940 tgt ctc ttt cct tgg tgt ggc ctg ctc ctc gac acc cgg act ttg gaa      2883
Cys Leu Phe Pro Trp Cys Gly Leu Leu Leu Asp Thr Arg Thr Leu Glu
            945                 950                 955 gtc ttt tgc gat tac tcc agc tat gca cag aca tcc att agg agc agc      2931
Val Phe Cys Asp Tyr Ser Ser Tyr Ala Gln Thr Ser Ile Arg Ser Ser
        960                 965                 970 ctg aca ttc agc cag ggc aca cgg ccc ggc cgc aat atg agg aga aag      2979
Leu Thr Phe Ser Gln Gly Thr Arg Pro Gly Arg Asn Met Arg Arg Lys
    975                 980                 985 ttg ctc gcc gtt atg aga ctc aag tgc tgt gca gtc ttt ctt gat ctg      3027
Leu Leu Ala Val Met Arg Leu Lys Cys Cys Ala Val Phe Leu Asp Leu
990                 995                 1000                1005 cag gtc aat tct att cat acc gtt tac acc aac atc tat aaa att           3072
Gln Val Asn Ser Ile His Thr Val Tyr Thr Asn Ile Tyr Lys Ile
                1010                1015                1020 ttc ctg ctc cag gca tat aga ttt cac gcc tgc gtg ttg cag ttc           3117
Phe Leu Leu Gln Ala Tyr Arg Phe His Ala Cys Val Leu Gln Phe
            1025                1030                1035 cca ttc aat cag ccc gtt cgg aag aac ccc agt ttc ttt ctc agg           3162
Pro Phe Asn Gln Pro Val Arg Lys Asn Pro Ser Phe Phe Leu Arg
        1040                1045                1050 gtt att gct gat acc gcc tcc cgc tgt tac tcc ctg ctt aag gcc           3207
Val Ile Ala Asp Thr Ala Ser Arg Cys Tyr Ser Leu Leu Lys Ala
    1055                1060                1065 aag aac aca gga ctt tca ttg ggt gct aaa ggc gcc agt gga cct           3252
Lys Asn Thr Gly Leu Ser Leu Gly Ala Lys Gly Ala Ser Gly Pro
1070                1075                1080 ttc cct tct gaa gcc gct cgg tgg ctc tgt ttg cac gca ttc ctt           3297
Phe Pro Ser Glu Ala Ala Arg Trp Leu Cys Leu His Ala Phe Leu
                1085                1090                1095
```

```
ctg aag ttg gct aga cac agc tct act tac aga tgc ctt ctg ggc    3342
Leu Lys Leu Ala Arg His Ser Ser Thr Tyr Arg Cys Leu Leu Gly
            1100                1105                1110 ccc ctt aga gct gct aag gct cat ctg tca aga cag ctc cca aga    3387
Pro Leu Arg Ala Ala Lys Ala His Leu Ser Arg Gln Leu Pro Arg
            1115                1120                1125 ggc act ctc gcc gca ctg gag gcc gca gcc gac ccc tcc ctc act    3432
Gly Thr Leu Ala Ala Leu Glu Ala Ala Ala Asp Pro Ser Leu Thr
            1130                1135                1140 gca gat ttt aag act att ctc gat acc gag ctt aag ttg tca gac    3477
Ala Asp Phe Lys Thr Ile Leu Asp Thr Glu Leu Lys Leu Ser Asp
            1145                1150                1155 tac gag gga cgc ctg att cag aat agc ctg aca ggc aaa ccc att    3522
Tyr Glu Gly Arg Leu Ile Gln Asn Ser Leu Thr Gly Lys Pro Ile
            1160                1165                1170 cct aat ccc ctg ttg ggt ttg gat tcc aca tgataatcta ga          3564
Pro Asn Pro Leu Leu Gly Leu Asp Ser Thr
            1175                1180
```

<210> SEQ ID NO 4
<211> LENGTH: 1180
<212> TYPE: PRT
<213> ORGANISM: Artificial
<220> FEATURE:
<223> OTHER INFORMATION: Synthetic Construct

<400> SEQUENCE: 4

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Arg Ala Leu Val
65                  70                  75                  80

Ala Gln Cys Leu Val Cys Val Pro Trp Gly Ala Arg Pro Pro Ala
                85                  90                  95

Ala Pro Cys Phe Arg Gln Val Ser Cys Leu Lys Glu Leu Val Ala Arg
            100                 105                 110

Val Val Gln Arg Leu Cys Glu Arg Gly Ala Arg Asn Val Leu Ala Phe
        115                 120                 125

Gly Phe Ala Leu Leu Asp Gly Ala Arg Gly Gly Pro Pro Val Ala Phe
    130                 135                 140

Thr Thr Ser Val Arg Ser Tyr Leu Pro Asn Thr Val Thr Glu Thr Leu
145                 150                 155                 160

Arg Gly Ser Gly Ala Trp Gly Leu Leu Leu Arg Arg Val Gly Asp Asp
                165                 170                 175

Val Leu Thr His Leu Leu Ala Arg Cys Ala Leu Tyr Leu Leu Val Ala
            180                 185                 190

Pro Ser Cys Ala Tyr Gln Val Cys Gly Pro Leu Tyr Asp Leu Cys
        195                 200                 205

Ala Pro Ala Ser Leu Pro Leu Pro Ala Pro Gly Leu Pro Gly Leu Pro
    210                 215                 220

Gly Leu Pro Gly Leu Gly Ala Gly Ala Gly Ala Ser Ala Asp Leu Arg
225                 230                 235                 240
```

```
Pro Thr Arg Gln Ala Gln Asn Ser Gly Ala Arg Arg Arg Gly Ser
            245                 250                 255

Pro Gly Ser Gly Val Pro Leu Ala Lys Arg Pro Arg Arg Ser Val Ala
            260                 265                 270

Ser Glu Pro Glu Arg Gly Ala His Arg Ser Phe Pro Arg Ala Gln Gln
        275                 280                 285

Pro Pro Val Ser Glu Ala Pro Ala Val Thr Pro Ala Val Ala Ala Ser
290                 295                 300

Pro Ala Ala Ser Trp Glu Gly Gly Pro Pro Gly Thr Arg Pro Thr Thr
305                 310                 315                 320

Pro Ala Trp His Pro Tyr Pro Gly Pro Gln Gly Val Pro His Asp Pro
                325                 330                 335

Ala His Pro Glu Thr Lys Arg Phe Leu Tyr Cys Ser Gly Gly Arg Glu
            340                 345                 350

Arg Leu Arg Pro Ser Phe Leu Leu Ser Ala Leu Pro Pro Thr Leu Ser
        355                 360                 365

Gly Ala Arg Lys Leu Val Glu Thr Ile Phe Leu Gly Ser Ala Pro Gln
370                 375                 380

Lys Pro Gly Ala Ala Arg Arg Met Arg Arg Leu Pro Ala Arg Tyr Trp
385                 390                 395                 400

Arg Met Arg Pro Leu Phe Gln Glu Leu Leu Gly Asn His Ala Arg Cys
                405                 410                 415

Pro Tyr Arg Ala Leu Leu Arg Thr His Cys Pro Leu Arg Ala Met Ala
            420                 425                 430

Ala Lys Glu Gly Ser Gly Asn Gln Ala His Arg Gly Val Gly Ile Cys
        435                 440                 445

Pro Leu Glu Arg Pro Val Ala Ala Pro Gln Gln Thr Asp Ser Thr
450                 455                 460

Arg Leu Val Gln Leu Leu Arg Gln His Ser Ser Pro Trp Gln Val Tyr
465                 470                 475                 480

Ala Phe Leu Arg Ala Cys Leu Cys Arg Leu Val Pro Ala Gly Leu Trp
                485                 490                 495

Gly Ser Gly His Asn Arg Arg Phe Leu Arg Asn Val Lys Lys Phe
            500                 505                 510

Val Ser Leu Gly Lys His Ala Lys Leu Ser Leu Gln Glu Leu Thr Trp
        515                 520                 525

Lys Met Arg Val Gln Asp Cys Ala Trp Leu Arg Gly Ser Pro Gly Ala
530                 535                 540

Arg Cys Val Pro Ala Ala Glu His Arg Arg Glu Glu Val Leu Ala
545                 550                 555                 560

Lys Leu Leu Cys Trp Leu Met Gly Thr Tyr Val Val Glu Leu Leu Lys
                565                 570                 575

Ser Phe Phe Tyr Val Thr Glu Thr Thr Phe Gln Lys Asn Arg Leu Phe
            580                 585                 590

Phe Tyr Arg Lys Arg Ile Trp Ser Gln Leu Gln Ser Ile Gly Ile Arg
        595                 600                 605

Gln His Phe Asn Ser Val His Leu Arg Glu Leu Ser Glu Ala Glu Val
610                 615                 620

Arg Arg His Gln Glu Ala Arg Pro Thr Leu Leu Thr Ser Lys Leu Arg
625                 630                 635                 640

Phe Leu Pro Lys Pro Ser Gly Leu Arg Pro Ile Val Asn Met Asp Tyr
                645                 650                 655
```

```
Val Val Gly Ala Arg Thr Phe Arg Arg Asp Lys Lys Val Arg His Leu
            660                 665                 670

Thr Ser Gln Val Lys Asn Leu Phe Ser Val Leu Asn Tyr Glu Arg Ala
        675                 680                 685

Arg Arg Pro Ser Leu Leu Gly Ala Ser Val Leu Gly Met Asp Asp Ile
    690                 695                 700

His Arg Val Trp Arg Ser Phe Val Leu Arg Val Arg Ala Gln Asp Pro
705                 710                 715                 720

Ala Pro Gln Leu Tyr Phe Val Lys Val Asp Val Thr Gly Ala Tyr Asp
                725                 730                 735

Ala Leu Pro Gln Asp Lys Leu Val Glu Val Ile Ala Asn Val Ile Arg
            740                 745                 750

Pro Gln Glu Asn Thr Tyr Cys Val Arg His Tyr Ala Val Val Gln Arg
        755                 760                 765

Thr Ala Gln Gly His Val Arg Lys Ser Phe Lys Arg His Val Ser Thr
    770                 775                 780

Phe Val Asp Leu Gln Pro Tyr Met Arg Gln Phe Val Glu His Leu Gln
785                 790                 795                 800

Glu Thr Ser Ser Leu Arg Asp Ala Val Val Ile Glu Gln Ser Ser Ser
                805                 810                 815

Leu Asn Glu Thr Gly His Ser Leu Phe His Leu Phe Leu Arg Leu Val
            820                 825                 830

His Asn His Val Ile Arg Ile Gly Gly Lys Ser Tyr Val Gln Cys Gln
        835                 840                 845

Gly Ile Pro Gln Gly Ser Ile Leu Ser Thr Leu Leu Cys Ser Leu Cys
    850                 855                 860

Tyr Gly Asp Met Glu Ser Arg Leu Phe Ser Gly Ile Gln Gln Asp Gly
865                 870                 875                 880

Val Leu Leu Arg Leu Phe Leu Leu Val Thr Pro His Leu Ala Gln Ala
                885                 890                 895

Gln Ala Phe Leu Arg Thr Leu Val Ser Gly Val Pro Glu Tyr Gly Cys
            900                 905                 910

Thr Ala Asn Leu Gln Lys Thr Ala Val Asn Phe Pro Val Asp Thr Gly
        915                 920                 925

Ala Pro Gly Ser Ala Ala Pro Leu Gln Leu Pro Ala His Cys Leu Phe
    930                 935                 940

Pro Trp Cys Gly Leu Leu Leu Asp Thr Arg Thr Leu Glu Val Phe Cys
945                 950                 955                 960

Asp Tyr Ser Ser Tyr Ala Gln Thr Ser Ile Arg Ser Ser Leu Thr Phe
                965                 970                 975

Ser Gln Gly Thr Arg Pro Gly Arg Asn Met Arg Arg Lys Leu Leu Ala
            980                 985                 990

Val Met Arg Leu Lys Cys Cys Ala Val Phe Leu Asp Leu Gln Val Asn
        995                 1000                1005

Ser Ile His Thr Val Tyr Thr Asn Ile Tyr Lys Ile Phe Leu Leu
    1010                1015                1020

Gln Ala Tyr Arg Phe His Ala Cys Val Leu Gln Phe Pro Phe Asn
    1025                1030                1035

Gln Pro Val Arg Lys Asn Pro Ser Phe Phe Leu Arg Val Ile Ala
    1040                1045                1050

Asp Thr Ala Ser Arg Cys Tyr Ser Leu Leu Lys Ala Lys Asn Thr
    1055                1060                1065

Gly Leu Ser Leu Gly Ala Lys Gly Ala Ser Gly Pro Phe Pro Ser
```

-continued

```
                    1070                1075                1080
Glu Ala Ala Arg Trp Leu Cys Leu His Ala Phe Leu Leu Lys Leu
            1085                1090                1095
Ala Arg His Ser Ser Thr Tyr Arg Cys Leu Leu Gly Pro Leu Arg
        1100                1105                1110
Ala Ala Lys Ala His Leu Ser Arg Gln Leu Pro Arg Gly Thr Leu
        1115                1120                1125
Ala Ala Leu Glu Ala Ala Ala Asp Pro Ser Leu Thr Ala Asp Phe
        1130                1135                1140
Lys Thr Ile Leu Asp Thr Glu Leu Lys Leu Ser Asp Tyr Glu Gly
        1145                1150                1155
Arg Leu Ile Gln Asn Ser Leu Thr Gly Lys Pro Ile Pro Asn Pro
        1160                1165                1170
Leu Leu Gly Leu Asp Ser Thr
        1175                1180

<210> SEQ ID NO 5
<211> LENGTH: 1024
<212> TYPE: PRT
<213> ORGANISM: Felis catus

<400> SEQUENCE: 5

Asn Val Leu Ala Phe Gly Phe Ala Leu Leu Asp Gly Ala Arg Gly Gly
1               5                   10                  15
Pro Pro Val Val Phe Thr Thr Ser Val Arg Ser Tyr Leu Pro Asn Thr
            20                  25                  30
Val Thr Glu Thr Leu Arg Gly Ser Gly Ala Trp Gly Leu Leu Arg
        35                  40                  45
Arg Val Gly Asp Asp Val Leu Ala His Leu Leu Thr Arg Cys Ala Leu
    50                  55                  60
Tyr Val Leu Val Ala Pro Ser Cys Ala Tyr Gln Val Cys Gly Pro Pro
65                  70                  75                  80
Leu Tyr Asp Leu Cys Ala Pro Ala Ala Thr Arg Pro Leu Ala Thr Ser
                85                  90                  95
Gly His Arg Pro Gly Thr Arg Met Asp Leu Arg Pro Thr Arg Gln Ala
            100                 105                 110
Arg Asn Ala Gly Ala Arg Arg Arg Gly Ala Gly Gly Ser Ser Pro
        115                 120                 125
Pro Leu Ala Lys Arg Pro Arg His Asp Val Lys Thr Pro Glu Pro Glu
        130                 135                 140
Arg Gly Pro Ala Ser Pro Ser Ser Arg His Pro Pro Gly Arg Ala His
145                 150                 155                 160
Gly Leu Ser Gly Gly Glu Pro Gly Ala Val Thr Ser Ala Arg Ala Ala
                165                 170                 175
Ala Glu Ala Asn Ser Gly Glu Gly Gly Pro Pro Gly Thr Arg Leu Thr
            180                 185                 190
Ser Ala Gly Ala Gln Leu Ser Arg Pro Gln Gly Val Pro Leu Ser His
        195                 200                 205
Leu Ser His Pro Glu Thr Lys His Phe Leu Tyr Cys Pro Gly Gly Lys
        210                 215                 220
Glu Arg Leu Arg Pro Ser Phe Leu Leu Ser Ala Leu Arg Pro Ser Leu
225                 230                 235                 240
Thr Gly Ala Arg Thr Leu Leu Glu Ala Ile Phe Leu Gly Ser Lys Ser
                245                 250                 255
```

```
Pro Arg Pro Gly Ala Ala Arg Arg Thr Arg Arg Leu Pro Ala Arg Tyr
            260                 265                 270

Trp Arg Met Arg Pro Leu Phe Arg Glu Leu Leu Ala Asn His Ala Arg
        275                 280                 285

Cys Pro Tyr Asp Ala Leu Leu Arg Thr His Cys Pro Leu Arg Ala Pro
    290                 295                 300

Ala Pro Ala Glu Gly Ser Ser Arg Gly Val Gly Gly Ala Gly Gly
305                 310                 315                 320

Cys Ala Leu Gly Arg Pro Pro Gly Ala Pro Gln Glu Gln Thr Asp Ser
                325                 330                 335

Thr Arg Leu Val Gln Leu Leu Arg Gln His Ser Ser Pro Trp Gln Val
            340                 345                 350

Tyr Ala Phe Leu Arg Ala Cys Leu Cys Arg Leu Val Pro Ala Gly Leu
        355                 360                 365

Trp Gly Ser Gly His Asn Arg Arg Phe Leu Arg Asn Val Lys Lys
    370                 375                 380

Phe Val Ser Leu Gly Lys His Ala Lys Leu Ser Leu Gln Glu Leu Thr
385                 390                 395                 400

Trp Lys Met Arg Val Gln Asp Cys Ala Trp Leu Arg Gly Ser Pro Gly
                405                 410                 415

Ala Arg Cys Val Pro Ala Ala Glu His Arg Arg Arg Glu Glu Val Leu
            420                 425                 430

Ala Lys Leu Leu Cys Trp Leu Met Gly Thr Tyr Val Glu Leu Leu
        435                 440                 445

Lys Ser Phe Phe Tyr Val Thr Glu Thr Thr Phe Gln Lys Asn Arg Leu
    450                 455                 460

Phe Phe Tyr Arg Lys Arg Ile Trp Ser Gln Leu Gln Ser Ile Gly Ile
465                 470                 475                 480

Arg Gln His Phe Asn Ser Val His Leu Arg Glu Leu Ser Glu Ala Glu
                485                 490                 495

Val Arg Arg His Gln Glu Ala Arg Pro Thr Leu Leu Thr Ser Lys Leu
            500                 505                 510

Arg Phe Leu Pro Lys Pro Ser Gly Leu Arg Pro Ile Val Asn Met Asp
        515                 520                 525

Tyr Val Val Gly Ala Arg Thr Phe Arg Arg Asp Lys Lys Val Arg His
    530                 535                 540

Leu Thr Ser Gln Val Lys Asn Leu Phe Ser Val Leu Asn Tyr Glu Arg
545                 550                 555                 560

Ala Arg Arg Pro Ser Leu Leu Gly Ala Ser Val Leu Gly Met Asp Asp
                565                 570                 575

Ile His Arg Val Trp Arg Ser Phe Val Leu Arg Val Arg Ala Gln Asp
            580                 585                 590

Pro Ala Pro Gln Leu Tyr Phe Val Lys Val Asp Val Thr Gly Ala Tyr
        595                 600                 605

Asp Ala Leu Pro Gln Asp Lys Leu Val Glu Val Ile Ala Asn Val Ile
    610                 615                 620

Arg Pro Gln Glu Asn Thr Tyr Cys Val Arg His Tyr Ala Val Val Gln
625                 630                 635                 640

Arg Thr Ala Gln Gly His Val Arg Lys Ser Phe Lys Arg His Val Ser
                645                 650                 655

Thr Phe Val Asp Leu Gln Pro Tyr Met Arg Gln Phe Val Glu His Leu
            660                 665                 670

Gln Glu Thr Ser Ser Leu Arg Asp Ala Val Val Ile Glu Gln Ser Ser
```

```
                    675                 680                 685

Ser Leu Asn Glu Thr Gly His Ser Leu Phe His Leu Phe Arg Leu
    690                 695                 700

Val His Asn His Val Ile Arg Ile Gly Gly Lys Ser Tyr Val Gln Cys
705                 710                 715                 720

Gln Gly Ile Pro Gln Gly Ser Ile Leu Ser Thr Leu Leu Cys Ser Leu
                725                 730                 735

Cys Tyr Gly Asp Met Glu Ser Arg Leu Phe Ser Gly Ile Gln Gln Asp
                740                 745                 750

Gly Val Leu Leu Arg Leu Val Asp Asp Phe Leu Leu Val Thr Pro His
                755                 760                 765

Leu Ala Gln Ala Gln Ala Phe Leu Arg Thr Leu Val Ser Gly Val Pro
770                 775                 780

Glu Tyr Gly Cys Thr Ala Asn Leu Gln Lys Thr Ala Val Asn Phe Pro
785                 790                 795                 800

Val Asp Thr Gly Ala Pro Gly Ser Ala Ala Pro Leu Gln Leu Pro Ala
                805                 810                 815

His Cys Leu Phe Pro Trp Cys Gly Leu Leu Leu Asp Thr Arg Thr Leu
                820                 825                 830

Glu Val Phe Cys Asp Tyr Ser Ser Tyr Ala Gln Thr Ser Ile Arg Ser
                835                 840                 845

Ser Leu Thr Phe Ser Gln Gly Thr Arg Pro Gly Arg Asn Met Arg Arg
                850                 855                 860

Lys Leu Leu Ala Val Met Arg Leu Lys Cys Cys Ala Val Phe Leu Asp
865                 870                 875                 880

Leu Gln Val Asn Ser Ile His Thr Val Tyr Thr Asn Ile Tyr Lys Ile
                885                 890                 895

Phe Leu Leu Gln Ala Tyr Arg Phe His Ala Cys Val Leu Gln Phe Pro
                900                 905                 910

Phe Asn Gln Pro Val Arg Lys Asn Pro Ser Phe Phe Leu Arg Val Ile
                915                 920                 925

Ala Asp Thr Ala Ser Arg Cys Tyr Ser Leu Leu Lys Ala Lys Asn Thr
                930                 935                 940

Gly Leu Ser Leu Gly Ala Lys Gly Ala Ser Gly Pro Phe Pro Ser Glu
945                 950                 955                 960

Ala Ala Arg Trp Leu Cys Leu His Ala Phe Leu Leu Lys Leu Ala Arg
                965                 970                 975

His Ser Ser Thr Tyr Arg Cys Leu Leu Gly Pro Leu Arg Ala Ala Lys
                980                 985                 990

Ala Gln Leu Arg Arg Gln Leu Pro  Arg Ala Thr Leu Asp  Ala Leu Glu
                995                 1000                1005

Ala Ala  Ala Ser Pro Gly Leu  Pro Ala Asp Phe Arg  Thr Ile Leu
   1010                 1015                1020

Asp

<210> SEQ ID NO 6
<211> LENGTH: 633
<212> TYPE: PRT
<213> ORGANISM: Felis catus

<400> SEQUENCE: 6

Leu Val Gln Leu Leu Arg Gln His Ser Ser Pro Trp Gln Val Tyr Ala
1               5                   10                  15

Phe Leu Arg Ala Cys Leu Cys Arg Leu Val Pro Ala Gly Leu Trp Gly
```

```
                  20                  25                  30
Ser Gly His Asn Arg Arg Phe Leu Arg Asn Val Lys Lys Phe Val
            35                  40                  45
Ser Leu Gly Lys His Ala Lys Leu Ser Leu Gln Glu Leu Thr Trp Lys
    50                  55                  60
Met Arg Val Gln Asp Cys Ala Trp Leu Arg Gly Ser Pro Gly Ala Arg
65                  70                  75                  80
Cys Val Pro Ala Ala Glu His Arg Arg Glu Glu Val Leu Ala Lys
                85                  90                  95
Leu Leu Cys Trp Leu Met Gly Thr Tyr Val Val Glu Leu Leu Lys Ser
            100                 105                 110
Phe Phe Tyr Val Thr Glu Thr Thr Phe Gln Lys Asn Arg Leu Phe Phe
        115                 120                 125
Tyr Arg Lys Arg Ile Trp Ser Gln Leu Gln Ser Ile Gly Ile Arg Gln
        130                 135                 140
His Phe Asn Ser Val His Leu Arg Glu Leu Ser Glu Ala Glu Val Arg
145                 150                 155                 160
Arg His Gln Glu Ala Arg Pro Thr Leu Leu Thr Ser Lys Leu Arg Phe
                165                 170                 175
Leu Pro Lys Pro Ser Gly Leu Arg Pro Ile Val Asn Met Asp Tyr Val
            180                 185                 190
Val Gly Ala Arg Thr Phe Arg Arg Asp Lys Lys Val Arg His Leu Thr
        195                 200                 205
Ser Gln Val Lys Asn Leu Phe Ser Val Leu Asn Tyr Glu Arg Ala Arg
    210                 215                 220
Arg Pro Ser Leu Leu Gly Ala Ser Val Leu Gly Met Asp Asp Ile His
225                 230                 235                 240
Arg Val Trp Arg Ser Phe Val Leu Arg Val Arg Ala Gln Asp Pro Ala
                245                 250                 255
Pro Gln Leu Tyr Phe Val Lys Val Asp Val Thr Gly Ala Tyr Asp Ala
            260                 265                 270
Leu Pro Gln Asp Lys Leu Val Glu Val Ile Ala Asn Val Ile Arg Pro
        275                 280                 285
Gln Glu Asn Thr Tyr Cys Val Arg His Tyr Ala Val Val Gln Arg Thr
    290                 295                 300
Ala Gln Gly His Val Arg Lys Ser Phe Lys Arg His Val Ser Thr Phe
305                 310                 315                 320
Val Asp Leu Gln Pro Tyr Met Arg Gln Phe Val Glu His Leu Gln Glu
                325                 330                 335
Thr Ser Ser Leu Arg Asp Ala Val Val Ile Glu Gln Ser Ser Ser Leu
            340                 345                 350
Asn Glu Thr Gly His Ser Leu Phe His Leu Phe Leu Arg Leu Val His
        355                 360                 365
Asn His Val Ile Arg Ile Gly Gly Lys Ser Tyr Val Gln Cys Gln Gly
    370                 375                 380
Ile Pro Gln Gly Ser Ile Leu Ser Thr Leu Leu Cys Ser Leu Cys Tyr
385                 390                 395                 400
Gly Asp Met Glu Ser Arg Leu Phe Ser Gly Ile Gln Gln Asp Gly Val
                405                 410                 415
Leu Leu Arg Leu Val Asp Asp Phe Leu Leu Val Thr Pro His Leu Ala
            420                 425                 430
Gln Ala Gln Ala Phe Leu Arg Thr Leu Val Ser Gly Val Pro Glu Tyr
        435                 440                 445
```

-continued

```
Gly Cys Thr Ala Asn Leu Gln Lys Thr Ala Val Asn Phe Pro Val Asp
    450                 455                 460
Thr Gly Ala Pro Gly Ser Ala Ala Pro Leu Gln Leu Pro Ala His Cys
465                 470                 475                 480
Leu Phe Pro Trp Cys Gly Leu Leu Asp Thr Arg Thr Leu Glu Val
                485                 490                 495
Phe Cys Asp Tyr Ser Ser Tyr Ala Gln Thr Ser Ile Arg Ser Ser Leu
                500                 505                 510
Thr Phe Ser Gln Gly Thr Arg Pro Gly Arg Asn Met Arg Arg Lys Leu
            515                 520                 525
Leu Ala Val Met Arg Leu Lys Cys Cys Ala Val Phe Leu Asp Leu Gln
530                 535                 540
Val Asn Ser Ile His Thr Val Tyr Thr Asn Ile Tyr Lys Ile Phe Leu
545                 550                 555                 560
Leu Gln Ala Tyr Arg Phe His Ala Cys Val Leu Gln Phe Pro Phe Asn
                565                 570                 575
Gln Pro Val Arg Lys Asn Pro Ser Phe Phe Leu Arg Val Ile Ala Asp
            580                 585                 590
Thr Ala Ser Arg Cys Tyr Ser Leu Leu Lys Ala Lys Asn Thr Gly Leu
            595                 600                 605
Ser Leu Gly Ala Lys Gly Ala Ser Gly Pro Phe Pro Ser Glu Ala Ala
        610                 615                 620
Arg Trp Leu Cys Leu His Ala Phe Leu
625                 630

<210> SEQ ID NO 7
<211> LENGTH: 1021
<212> TYPE: PRT
<213> ORGANISM: Felis catus

<400> SEQUENCE: 7

Asn Val Leu Ala Phe Gly Phe Ala Leu Leu Asp Gly Ala Arg Gly Gly
1               5                   10                  15
Pro Pro Val Val Phe Thr Thr Ser Val Arg Ser Tyr Leu Pro Asn Thr
            20                  25                  30
Val Thr Glu Thr Leu Arg Gly Ser Gly Ala Trp Gly Leu Leu Leu Arg
        35                  40                  45
Arg Val Gly Asp Asp Val Leu Ala His Leu Leu Thr Arg Cys Ala Leu
    50                  55                  60
Tyr Val Leu Val Ala Pro Ser Cys Ala Tyr Gln Val Cys Gly Pro Pro
65                  70                  75                  80
Leu Tyr Asp Leu Cys Ala Pro Ala Ala Thr Arg Pro Leu Ala Thr Ser
                85                  90                  95
Gly His Arg Pro Gly Thr Arg Met Asp Leu Arg Pro Thr Arg Gln Ala
            100                 105                 110
Arg Asn Ala Gly Ala Arg Arg Arg Gly Ala Gly Gly Ser Ser Pro
        115                 120                 125
Pro Leu Ala Lys Arg Pro Arg His Asp Val Lys Thr Pro Glu Pro Glu
    130                 135                 140
Arg Gly Pro Ala Ser Pro Ser Ser Arg His Pro Pro Gly Arg Ala His
145                 150                 155                 160
Gly Leu Ser Gly Gly Glu Pro Gly Ala Val Thr Ser Ala Arg Ala Ala
                165                 170                 175
Ala Glu Ala Asn Ser Gly Glu Gly Gly Pro Pro Gly Thr Arg Leu Thr
```

```
                    180                 185                 190
Ser Ala Gly Ala Gln Leu Ser Arg Pro Gln Gly Val Pro Leu Ser His
            195                 200                 205

Leu Ser His Pro Glu Thr Lys His Phe Leu Tyr Cys Pro Gly Gly Lys
        210                 215                 220

Glu Arg Leu Arg Pro Ser Phe Leu Leu Ser Ala Leu Arg Pro Ser Leu
225                 230                 235                 240

Thr Gly Ala Arg Thr Leu Leu Glu Ala Ile Phe Leu Gly Ser Lys Ser
                245                 250                 255

Pro Arg Pro Gly Ala Ala Arg Arg Thr Arg Arg Leu Pro Ala Arg Tyr
            260                 265                 270

Trp Arg Met Arg Pro Leu Phe Arg Glu Leu Leu Ala Asn His Ala Arg
        275                 280                 285

Cys Pro Tyr Asp Ala Leu Leu Arg Thr His Cys Pro Leu Arg Ala Pro
    290                 295                 300

Ala Pro Ala Glu Gly Ser Ser Arg Gly Val Gly Gly Ala Gly Gly
305                 310                 315                 320

Cys Ala Leu Gly Arg Pro Pro Gly Ala Pro Gln Glu Gln Thr Asp Ser
                325                 330                 335

Thr Arg Leu Val Gln Leu Leu Arg Gln His Ser Ser Pro Trp Gln Val
            340                 345                 350

Tyr Ala Phe Leu Arg Ala Cys Leu Cys Arg Leu Val Pro Ala Gly Leu
        355                 360                 365

Trp Gly Ser Gly His Asn Arg Arg Arg Phe Leu Arg Asn Val Lys Lys
    370                 375                 380

Phe Val Ser Leu Gly Lys His Ala Lys Leu Ser Leu Gln Glu Leu Thr
385                 390                 395                 400

Trp Lys Met Arg Val Gln Asp Cys Ala Trp Leu Arg Gly Ser Pro Gly
                405                 410                 415

Ala Arg Cys Val Pro Ala Ala Glu His Arg Arg Arg Glu Glu Val Leu
            420                 425                 430

Ala Lys Leu Leu Cys Trp Leu Met Gly Thr Tyr Val Val Glu Leu Leu
        435                 440                 445

Lys Ser Phe Phe Tyr Val Thr Glu Thr Thr Phe Gln Lys Asn Arg Leu
    450                 455                 460

Phe Phe Tyr Arg Lys Arg Ile Trp Ser Gln Leu Gln Ser Ile Gly Ile
465                 470                 475                 480

Arg Gln His Phe Asn Ser Val His Leu Arg Glu Leu Ser Glu Ala Glu
                485                 490                 495

Val Arg Arg His Gln Glu Ala Arg Pro Thr Leu Leu Thr Ser Lys Leu
            500                 505                 510

Arg Phe Leu Pro Lys Pro Ser Gly Leu Arg Pro Ile Val Asn Met Asp
        515                 520                 525

Tyr Val Val Gly Ala Arg Thr Phe Arg Arg Asp Lys Lys Val Arg His
    530                 535                 540

Leu Thr Ser Gln Val Lys Asn Leu Phe Ser Val Leu Asn Tyr Glu Arg
545                 550                 555                 560

Ala Arg Arg Pro Ser Leu Leu Gly Ala Ser Val Leu Gly Met Asp Asp
                565                 570                 575

Ile His Arg Val Trp Arg Ser Phe Val Leu Arg Val Arg Ala Gln Asp
            580                 585                 590

Pro Ala Pro Gln Leu Tyr Phe Val Lys Val Asp Val Thr Gly Ala Tyr
        595                 600                 605
```

-continued

Asp Ala Leu Pro Gln Asp Lys Leu Val Glu Val Ile Ala Asn Val Ile
610                 615                 620

Arg Pro Gln Glu Asn Thr Tyr Cys Val Arg His Tyr Ala Val Val Gln
625                 630                 635                 640

Arg Thr Ala Gln Gly His Val Arg Lys Ser Phe Lys Arg His Val Ser
            645                 650                 655

Thr Phe Val Asp Leu Gln Pro Tyr Met Arg Gln Phe Val Glu His Leu
            660                 665                 670

Gln Glu Thr Ser Ser Leu Arg Asp Ala Val Val Ile Glu Gln Ser Ser
            675                 680                 685

Ser Leu Asn Glu Thr Gly His Ser Leu Phe His Leu Phe Leu Arg Leu
690                 695                 700

Val His Asn His Val Ile Arg Ile Gly Gly Lys Ser Tyr Val Gln Cys
705                 710                 715                 720

Gln Gly Ile Pro Gln Gly Ser Ile Leu Ser Thr Leu Leu Cys Ser Leu
            725                 730                 735

Cys Tyr Gly Asp Met Glu Ser Arg Leu Phe Ser Gly Ile Gln Gln Asp
            740                 745                 750

Gly Val Leu Leu Arg Leu Phe Leu Leu Val Thr Pro His Leu Ala Gln
            755                 760                 765

Ala Gln Ala Phe Leu Arg Thr Leu Val Ser Gly Val Pro Glu Tyr Gly
770                 775                 780

Cys Thr Ala Asn Leu Gln Lys Thr Ala Val Asn Phe Pro Val Asp Thr
785                 790                 795                 800

Gly Ala Pro Gly Ser Ala Ala Pro Leu Gln Leu Pro Ala His Cys Leu
            805                 810                 815

Phe Pro Trp Cys Gly Leu Leu Leu Asp Thr Arg Thr Leu Glu Val Phe
            820                 825                 830

Cys Asp Tyr Ser Ser Tyr Ala Gln Thr Ser Ile Arg Ser Ser Leu Thr
            835                 840                 845

Phe Ser Gln Gly Thr Arg Pro Gly Arg Asn Met Arg Arg Lys Leu Leu
850                 855                 860

Ala Val Met Arg Leu Lys Cys Cys Ala Val Phe Leu Asp Leu Gln Val
865                 870                 875                 880

Asn Ser Ile His Thr Val Tyr Thr Asn Ile Tyr Lys Ile Phe Leu Leu
            885                 890                 895

Gln Ala Tyr Arg Phe His Ala Cys Val Leu Gln Phe Pro Phe Asn Gln
            900                 905                 910

Pro Val Arg Lys Asn Pro Ser Phe Leu Arg Val Ile Ala Asp Thr
            915                 920                 925

Ala Ser Arg Cys Tyr Ser Leu Leu Lys Ala Lys Asn Thr Gly Leu Ser
930                 935                 940

Leu Gly Ala Lys Gly Ala Ser Gly Pro Phe Pro Ser Glu Ala Ala Arg
945                 950                 955                 960

Trp Leu Cys Leu His Ala Phe Leu Leu Lys Leu Ala Arg His Ser Ser
            965                 970                 975

Thr Tyr Arg Cys Leu Leu Gly Pro Leu Arg Ala Ala Lys Ala Gln Leu
            980                 985                 990

Arg Arg Gln Leu Pro Arg Ala Thr Leu Asp Ala Leu Glu Ala Ala Ala
            995                 1000                1005

Ser Pro Gly Leu Pro Ala Asp Phe Arg Thr Ile Leu Asp
   1010                1015                1020

<210> SEQ ID NO 8
<211> LENGTH: 630
<212> TYPE: PRT
<213> ORGANISM: Felis catus

<400> SEQUENCE: 8

```
Leu Val Gln Leu Leu Arg Gln His Ser Ser Pro Trp Gln Val Tyr Ala
1               5                   10                  15

Phe Leu Arg Ala Cys Leu Cys Arg Leu Val Pro Ala Gly Leu Trp Gly
            20                  25                  30

Ser Gly His Asn Arg Arg Phe Leu Arg Asn Val Lys Lys Phe Val
        35                  40                  45

Ser Leu Gly Lys His Ala Lys Leu Ser Leu Gln Glu Leu Thr Trp Lys
50                  55                  60

Met Arg Val Gln Asp Cys Ala Trp Leu Arg Gly Ser Pro Gly Ala Arg
65                  70                  75                  80

Cys Val Pro Ala Ala Glu His Arg Arg Glu Glu Val Leu Ala Lys
                85                  90                  95

Leu Leu Cys Trp Leu Met Gly Thr Tyr Val Val Glu Leu Leu Lys Ser
            100                 105                 110

Phe Phe Tyr Val Thr Glu Thr Thr Phe Gln Lys Asn Arg Leu Phe Phe
        115                 120                 125

Tyr Arg Lys Arg Ile Trp Ser Gln Leu Gln Ser Ile Gly Ile Arg Gln
130                 135                 140

His Phe Asn Ser Val His Leu Arg Glu Leu Ser Glu Ala Glu Val Arg
145                 150                 155                 160

Arg His Gln Glu Ala Arg Pro Thr Leu Leu Thr Ser Lys Leu Arg Phe
                165                 170                 175

Leu Pro Lys Pro Ser Gly Leu Arg Pro Ile Val Asn Met Asp Tyr Val
            180                 185                 190

Val Gly Ala Arg Thr Phe Arg Arg Asp Lys Lys Val Arg His Leu Thr
        195                 200                 205

Ser Gln Val Lys Asn Leu Phe Ser Val Leu Asn Tyr Glu Arg Ala Arg
210                 215                 220

Arg Pro Ser Leu Leu Gly Ala Ser Val Leu Gly Met Asp Asp Ile His
225                 230                 235                 240

Arg Val Trp Arg Ser Phe Val Leu Arg Val Arg Ala Gln Asp Pro Ala
                245                 250                 255

Pro Gln Leu Tyr Phe Val Lys Val Asp Val Thr Gly Ala Tyr Asp Ala
            260                 265                 270

Leu Pro Gln Asp Lys Leu Val Glu Val Ile Ala Asn Val Ile Arg Pro
        275                 280                 285

Gln Glu Asn Thr Tyr Cys Val Arg His Tyr Ala Val Val Gln Arg Thr
290                 295                 300

Ala Gln Gly His Val Arg Lys Ser Phe Lys Arg His Val Ser Thr Phe
305                 310                 315                 320

Val Asp Leu Gln Pro Tyr Met Arg Gln Phe Val Glu His Leu Gln Glu
                325                 330                 335

Thr Ser Ser Leu Arg Asp Ala Val Val Ile Glu Gln Ser Ser Ser Leu
            340                 345                 350

Asn Glu Thr Gly His Ser Leu Phe His Leu Phe Leu Arg Leu Val His
        355                 360                 365

Asn His Val Ile Arg Ile Gly Gly Lys Ser Tyr Val Gln Cys Gln Gly
370                 375                 380
```

Ile Pro Gln Gly Ser Ile Leu Ser Thr Leu Leu Cys Ser Leu Cys Tyr
385                 390                 395                 400

Gly Asp Met Glu Ser Arg Leu Phe Ser Gly Ile Gln Gln Asp Gly Val
                405                 410                 415

Leu Leu Arg Leu Phe Leu Leu Val Thr Pro His Leu Ala Gln Ala Gln
            420                 425                 430

Ala Phe Leu Arg Thr Leu Val Ser Gly Val Pro Glu Tyr Gly Cys Thr
        435                 440                 445

Ala Asn Leu Gln Lys Thr Ala Val Asn Phe Pro Val Asp Thr Gly Ala
    450                 455                 460

Pro Gly Ser Ala Ala Pro Leu Gln Leu Pro Ala His Cys Leu Phe Pro
465                 470                 475                 480

Trp Cys Gly Leu Leu Leu Asp Thr Arg Thr Leu Glu Val Phe Cys Asp
                485                 490                 495

Tyr Ser Ser Tyr Ala Gln Thr Ser Ile Arg Ser Ser Leu Thr Phe Ser
            500                 505                 510

Gln Gly Thr Arg Pro Gly Arg Asn Met Arg Arg Lys Leu Leu Ala Val
        515                 520                 525

Met Arg Leu Lys Cys Cys Ala Val Phe Leu Asp Leu Gln Val Asn Ser
    530                 535                 540

Ile His Thr Val Tyr Thr Asn Ile Tyr Lys Ile Phe Leu Leu Gln Ala
545                 550                 555                 560

Tyr Arg Phe His Ala Cys Val Leu Gln Phe Pro Phe Asn Gln Pro Val
                565                 570                 575

Arg Lys Asn Pro Ser Phe Phe Leu Arg Val Ile Ala Asp Thr Ala Ser
            580                 585                 590

Arg Cys Tyr Ser Leu Leu Lys Ala Lys Asn Thr Gly Leu Ser Leu Gly
        595                 600                 605

Ala Lys Gly Ala Ser Gly Pro Phe Pro Ser Glu Ala Ala Arg Trp Leu
    610                 615                 620

Cys Leu His Ala Phe Leu
625                 630

<210> SEQ ID NO 9
<211> LENGTH: 1123
<212> TYPE: PRT
<213> ORGANISM: Canis familiaris

<400> SEQUENCE: 9

Met Pro Arg Ala Pro Arg Cys Arg Ala Val Arg Ala Leu Leu Arg Gly
1               5                   10                  15

Arg Tyr Arg Glu Val Leu Pro Leu Ala Thr Phe Leu Arg Arg Leu Gly
                20                  25                  30

Pro Pro Gly Arg Leu Leu Val Arg Arg Gly Asp Pro Ala Ala Phe Arg
            35                  40                  45

Ala Leu Val Ala Gln Cys Leu Val Cys Val Pro Trp Gly Ala Arg Pro
        50                  55                  60

Pro Pro Ala Ala Pro Cys Phe Arg Gln Val Ser Cys Leu Lys Glu Leu
65                  70                  75                  80

Val Ala Arg Val Val Gln Arg Leu Cys Glu Arg Gly Ala Arg Asn Val
                85                  90                  95

Leu Ala Phe Gly Phe Ala Leu Leu Asp Gly Ala Arg Gly Gly Pro Pro
            100                 105                 110

Val Ala Phe Thr Thr Ser Val Arg Ser Tyr Leu Pro Asn Thr Val Thr

-continued

```
            115                 120                 125
Glu Thr Leu Arg Gly Ser Gly Ala Trp Gly Leu Leu Arg Arg Val
        130                 135                 140

Gly Asp Asp Val Leu Thr His Leu Leu Ala Arg Cys Ala Leu Tyr Leu
145                 150                 155                 160

Leu Val Ala Pro Ser Cys Ala Tyr Gln Val Cys Gly Pro Pro Leu Tyr
                165                 170                 175

Asp Leu Cys Ala Pro Ala Ser Leu Pro Leu Pro Ala Pro Gly Leu Pro
                180                 185                 190

Gly Leu Pro Gly Leu Pro Gly Leu Gly Ala Gly Ala Gly Ala Ser Ala
            195                 200                 205

Asp Leu Arg Pro Thr Arg Gln Ala Gln Asn Ser Gly Ala Arg Arg Arg
        210                 215                 220

Arg Gly Ser Pro Gly Ser Gly Val Pro Leu Ala Lys Arg Pro Arg Arg
225                 230                 235                 240

Ser Val Ala Ser Glu Pro Glu Arg Gly Ala His Arg Ser Phe Pro Arg
                245                 250                 255

Ala Gln Gln Pro Pro Val Ser Glu Ala Pro Ala Val Thr Pro Ala Val
                260                 265                 270

Ala Ala Ser Pro Ala Ala Ser Trp Glu Gly Pro Pro Gly Thr Arg
            275                 280                 285

Pro Thr Thr Pro Ala Trp His Pro Tyr Pro Gly Pro Gln Gly Val Pro
        290                 295                 300

His Asp Pro Ala His Pro Glu Thr Lys Arg Phe Leu Tyr Cys Ser Gly
305                 310                 315                 320

Gly Arg Glu Arg Leu Arg Pro Ser Phe Leu Leu Ser Ala Leu Pro Pro
                325                 330                 335

Thr Leu Ser Gly Ala Arg Lys Leu Val Glu Thr Ile Phe Leu Gly Ser
            340                 345                 350

Ala Pro Gln Lys Pro Gly Ala Ala Arg Arg Met Arg Arg Leu Pro Ala
        355                 360                 365

Arg Tyr Trp Arg Met Arg Pro Leu Phe Gln Glu Leu Leu Gly Asn His
        370                 375                 380

Ala Arg Cys Pro Tyr Arg Ala Leu Leu Arg Thr His Cys Pro Leu Arg
385                 390                 395                 400

Ala Met Ala Ala Lys Glu Gly Ser Gly Asn Gln Ala His Arg Gly Val
                405                 410                 415

Gly Ile Cys Pro Leu Glu Arg Pro Val Ala Ala Pro Gln Glu Gln Thr
                420                 425                 430

Asp Ser Thr Arg Leu Val Gln Leu Leu Arg Gln His Ser Ser Pro Trp
        435                 440                 445

Gln Val Tyr Ala Phe Leu Arg Ala Cys Leu Cys Trp Leu Val Pro Thr
        450                 455                 460

Gly Leu Trp Gly Ser Arg His Asn Gln Arg Arg Phe Leu Arg Asn Val
465                 470                 475                 480

Lys Lys Phe Ile Ser Leu Gly Lys His Ala Lys Leu Ser Leu Gln Glu
                485                 490                 495

Leu Thr Trp Lys Met Lys Val Arg Asp Cys Thr Trp Leu His Gly Asn
            500                 505                 510

Pro Gly Ala Cys Cys Val Pro Ala Ala Glu His Arg Arg Glu Glu
        515                 520                 525

Ile Leu Ala Arg Phe Leu Val Leu Val Asp Gly His Ile Tyr Val Val
        530                 535                 540
```

```
Lys Leu Leu Arg Ser Phe Phe Tyr Val Thr Glu Thr Thr Phe Gln Lys
545                 550                 555                 560

Asn Arg Leu Phe Phe Tyr Arg Lys Ser Val Trp Ser Gln Leu Gln Ser
                565                 570                 575

Ile Gly Ile Arg Gln Leu Phe Asn Ser Val His Leu Arg Glu Leu Ser
            580                 585                 590

Glu Ala Glu Val Arg Arg His Arg Glu Ala Arg Pro Ala Leu Leu Thr
        595                 600                 605

Ser Arg Leu Arg Phe Leu Pro Lys Pro Ser Gly Leu Arg Pro Ile Val
    610                 615                 620

Asn Met Asp Tyr Ile Met Gly Ala Arg Thr Phe His Arg Asp Lys Lys
625                 630                 635                 640

Val Gln His Leu Thr Ser Gln Leu Lys Thr Leu Phe Ser Val Leu Asn
                645                 650                 655

Tyr Glu Arg Ala Arg Arg Pro Ser Leu Leu Gly Ala Ser Met Leu Gly
            660                 665                 670

Met Asp Asp Ile His Arg Ala Trp Arg Thr Phe Val Leu Arg Ile Arg
        675                 680                 685

Ala Gln Asn Pro Ala Pro Gln Leu Tyr Phe Val Lys Val Asp Val Thr
    690                 695                 700

Gly Ala Tyr Asp Ala Leu Pro Gln Asp Arg Leu Val Glu Val Ile Ala
705                 710                 715                 720

Asn Val Ile Arg Pro Gln Glu Ser Thr Tyr Cys Val Arg His Tyr Ala
                725                 730                 735

Val Val Gln Arg Thr Ala Arg Gly His Val Arg Lys Ala Phe Lys Arg
            740                 745                 750

His Val Ser Thr Phe Ala Asp Leu Gln Pro Tyr Met Arg Gln Phe Val
        755                 760                 765

Glu Arg Leu Gln Glu Thr Ser Leu Leu Arg Asp Ala Val Val Ile Glu
    770                 775                 780

Gln Ser Ser Ser Leu Asn Glu Ala Gly Ser Ser Leu Phe His Leu Phe
785                 790                 795                 800

Leu Arg Leu Val His Asn His Val Val Arg Ile Gly Gly Lys Ser Tyr
                805                 810                 815

Ile Gln Cys Gln Gly Val Pro Gln Gly Ser Ile Leu Ser Thr Leu Leu
            820                 825                 830

Cys Ser Leu Cys Tyr Gly Asp Met Glu Arg Arg Leu Phe Pro Gly Ile
        835                 840                 845

Glu Gln Asp Gly Val Leu Leu Arg Leu Val Asp Asp Phe Leu Leu Val
    850                 855                 860

Thr Pro His Leu Thr Gln Ala Gln Ala Phe Leu Arg Thr Leu Val Lys
865                 870                 875                 880

Gly Val Pro Glu Tyr Gly Cys Arg Ala Asn Leu Gln Lys Thr Ala Val
                885                 890                 895

Asn Phe Pro Val Glu Asp Gly Ala Leu Gly Ser Ala Ala Pro Leu Gln
            900                 905                 910

Leu Pro Ala His Cys Leu Phe Pro Trp Cys Gly Leu Leu Leu Asp Thr
        915                 920                 925

Arg Thr Leu Glu Val Ser Cys Asp Tyr Ser Ser Tyr Ala His Thr Ser
    930                 935                 940

Ile Arg Ala Ser Leu Thr Phe Ser Gln Gly Ala Lys Pro Gly Arg Asn
945                 950                 955                 960
```

```
Met Arg Arg Lys Leu Leu Ala Val Leu Arg Leu Lys Cys Cys Ala Leu
            965                 970                 975

Phe Leu Asp Leu Gln Val Asn Gly Ile His Thr Val Tyr Met Asn Val
            980                 985                 990

Tyr Lys Ile Phe Leu Leu Gln Ala Tyr Arg Phe His Ala Cys Val Leu
        995                1000                1005

Gln Leu Pro Phe Asn Gln Pro Val Arg Lys Asn Pro Ser Phe Phe
       1010                1015                1020

Leu Arg Val Ile Ala Asp Thr Ala Ser Cys Cys Tyr Ser Leu Leu
       1025                1030                1035

Lys Ala Arg Asn Ala Gly Leu Ser Leu Gly Ala Lys Gly Ala Ser
       1040                1045                1050

Gly Leu Phe Pro Ser Glu Ala Ala Arg Trp Leu Cys Leu His Ala
       1055                1060                1065

Phe Leu Leu Lys Leu Ala His His Ser Gly Thr Tyr Arg Cys Leu
       1070                1075                1080

Leu Gly Ala Leu Gln Ala Ala Lys Ala His Leu Ser Arg Gln Leu
       1085                1090                1095

Pro Arg Gly Thr Leu Ala Ala Leu Glu Ala Ala Ala Asp Pro Ser
       1100                1105                1110

Leu Thr Ala Asp Phe Lys Thr Ile Leu Asp
       1115                1120

<210> SEQ ID NO 10
<211> LENGTH: 9
<212> TYPE: PRT
<213> ORGANISM: Artificial
<220> FEATURE:
<223> OTHER INFORMATION: H2-restricted peptide

<400> SEQUENCE: 10

Arg Pro Ile Val Asn Met Asp Tyr Ile
1               5

<210> SEQ ID NO 11
<211> LENGTH: 9
<212> TYPE: PRT
<213> ORGANISM: Artificial
<220> FEATURE:
<223> OTHER INFORMATION: H2 restricted peptide

<400> SEQUENCE: 11

Arg Gln Leu Phe Asn Ser Val His Leu
1               5

<210> SEQ ID NO 12
<211> LENGTH: 9
<212> TYPE: PRT
<213> ORGANISM: Artificial
<220> FEATURE:
<223> OTHER INFORMATION: H2 restricted peptide

<400> SEQUENCE: 12

Thr Val Tyr Met Asn Val Tyr Lys Ile
1               5

<210> SEQ ID NO 13
<211> LENGTH: 15
<212> TYPE: PRT
<213> ORGANISM: Artificial
<220> FEATURE:
<223> OTHER INFORMATION: H2 restricted peptide
```

```
<400> SEQUENCE: 13

Cys Leu Leu Gly Pro Leu Arg Ala Ala Lys Ala His Leu Ser Arg
1               5                   10                  15

<210> SEQ ID NO 14
<211> LENGTH: 15
<212> TYPE: PRT
<213> ORGANISM: Artificial
<220> FEATURE:
<223> OTHER INFORMATION: H2 restricted peptide

<400> SEQUENCE: 14

Arg Cys Leu Leu Gly Pro Leu Arg Ala Ala Lys Ala His Leu Ser
1               5                   10                  15

<210> SEQ ID NO 15
<211> LENGTH: 15
<212> TYPE: PRT
<213> ORGANISM: Artificial
<220> FEATURE:
<223> OTHER INFORMATION: H2 restricted peptide

<400> SEQUENCE: 15

Tyr Ser Ser Tyr Ala Gln Thr Ser Ile Arg Ser Ser Leu Thr Phe
1               5                   10                  15

<210> SEQ ID NO 16
<211> LENGTH: 15
<212> TYPE: PRT
<213> ORGANISM: Artificial
<220> FEATURE:
<223> OTHER INFORMATION: H2 restricted peptide

<400> SEQUENCE: 16

Gly Pro Leu Arg Ala Ala Lys Ala His Leu Ser Arg Gln Leu Pro
1               5                   10                  15
```

The invention claimed is:

1. A nucleic acid molecule comprising:
   (i) a sequence encoding a full-length cat telomerase reverse transcriptase (TERT), wherein the cat TERT does not contain amino acids VDD within the TERT catalytic site as compared to SEQ ID NO: 5 and does not contain a nucleolar localization signal sequence, or
   (ii) a sequence encoding an antigenic fragment of cat TERT, wherein said sequence consists of at least 80% of the cat TERT sequence of (i).

2. An immunogenic composition comprising a nucleic acid molecule that comprises:
   (a) the nucleic acid molecule of claim 1, and
   (b) a carrier and/or excipient.

3. The composition of claim 2, wherein the nucleic acid molecule further encodes a non-cat TERT antigenic fragment.

4. The composition of claim 3, wherein the non-cat TERT antigenic fragment originates from a dog TERT sequence.

5. The composition of claim 2, wherein the nucleic acid molecule is a DNA molecule.

6. The composition of claim 2, wherein the nucleic acid molecule comprises the sequence encoding SEQ ID NO: 7.

7. A method for triggering an immune response in a cat, against cells that overexpress telomerase, which method comprises administering to the cat an effective amount of the immunogenic composition of claim 2.

8. The method of claim 7, wherein the cells that overexpress telomerase are dysplasia cells, tumor cells, or cells infected by an oncovirus.

9. The composition of claim 2, wherein the nucleic acid molecule further encodes ubiquitin.

10. The nucleic acid molecule of claim 1, which further encodes a non-cat TERT antigenic fragment.

11. The nucleic acid molecule of claim 1, wherein the nucleic acid molecule encodes the protein sequence of SEQ ID NO: 7.

12. The nucleic acid molecule of claim 1, wherein the nucleic acid molecule further encodes ubiquitin.

13. The nucleic acid molecule of claim 1, wherein the nucleic acid molecule is a DNA plasmid.

14. A method for triggering an immune response in a cat, against cells that overexpress telomerase, which method comprises administering to the cat an effective amount of the nucleic acid molecule of claim 1.

15. The method of claim 14, wherein the cells that overexpress telomerase are dysplasia cells, tumor cells, or cells infected by an oncovirus.

16. The method of claim 14, wherein the nucleic acid molecule further encodes ubiquitin.

* * * * *